(12) United States Patent
Robinson et al.

(10) Patent No.: US 12,370,249 B2
(45) Date of Patent: Jul. 29, 2025

(54) REPLICATION-DEFICIENT MODIFIED VACCINIA ANKARA (MVA) EXPRESSING MARBURG VIRUS GLYCOPROTEIN (GP) AND MATRIX PROTEIN (VP40)

(71) Applicant: GeoVax, Inc., Smyrna, GA (US)

(72) Inventors: Harriet Robinson, Palo Alto, CA (US); Arban Domi, Atlanta, GA (US); Michael Hellerstein, Atlanta, GA (US)

(73) Assignee: GeoVax, Inc., Smyrna, GA (US)

( * ) Notice: Subject to any disclaimer, the term of this patent is extended or adjusted under 35 U.S.C. 154(b) by 0 days.

(21) Appl. No.: 18/394,555

(22) Filed: Dec. 22, 2023

(65) Prior Publication Data

US 2024/0156940 A1 May 16, 2024

Related U.S. Application Data

(63) Continuation of application No. 17/584,231, filed on Jan. 25, 2022, now Pat. No. 11,896,657, which is a
(Continued)

(51) Int. Cl.
*A61K 39/12* (2006.01)
*C12N 15/86* (2006.01)
(Continued)

(52) U.S. Cl.
CPC .............. *A61K 39/12* (2013.01); *C12N 15/86* (2013.01); *C12N 15/863* (2013.01);
(Continued)

(58) Field of Classification Search
CPC ...... A61K 39/12; C12N 15/86; C12N 15/863; C12N 2710/24141; C12N 2710/24143;
(Continued)

(56) References Cited

U.S. PATENT DOCUMENTS

| 6,440,422 B1 | 8/2002 | Sutter et al. |
| 2003/0215794 A1 | 11/2003 | Kawaoka et al. |

(Continued)

FOREIGN PATENT DOCUMENTS

| WO | WO 2004/048582 A1 | 6/2004 |
| WO | WO 2015/066715 A1 | 5/2015 |

(Continued)

OTHER PUBLICATIONS

Falzarano, D., et al., 2011, Progress in filovirus vaccine development: evaluating the potential for clinical use, Exp. Rev. Vaccines 10(1):63-77.*

(Continued)

*Primary Examiner* — Jeffrey S Parkin
(74) *Attorney, Agent, or Firm* — Knowles Intellectual Property Strategies, LLC

(57) ABSTRACT

The compositions and methods are described for generating an immune response to a hemorrhagic fever virus such as ebolavirus, *Marburgvirus*, or arenavirus. The compositions and methods described herein relate to a modified vaccinia Ankara (MVA) vector encoding one or more viral antigens for generating a protective immune response to a member of genus *Ebolavirus* (such as a member of species *Zaire ebolavirus*), a member of genus *Marburgvirus* (such as a member of species *Marburg marburgvirus*), or a member of genus *Arenavirus* (such as a member of species *Lassa virus*) in the subject to which the vector is administered. The compositions and methods of the present invention are useful both prophylactically and therapeutically and may be used to prevent and/or treat an infection caused by ebolavirus, *Marburgvirus*, or arenavirus.

22 Claims, 14 Drawing Sheets

Specification includes a Sequence Listing.

Related U.S. Application Data continuation of application No. 15/543,139, filed as application No. PCT/US2016/013021 on Jan. 12, 2016, now Pat. No. 11,701,418.

(60) Provisional application No. 62/215,536, filed on Sep. 8, 2015, provisional application No. 62/213,819, filed on Sep. 3, 2015, provisional application No. 62/102,425, filed on Jan. 12, 2015.

(51) Int. Cl.
   *C12N 15/863* (2006.01)
   *A61K 39/00* (2006.01)

(52) U.S. Cl.
   CPC .............. *A61K 2039/5256* (2013.01); *A61K 2039/5258* (2013.01); *C12N 2710/24141* (2013.01); *C12N 2710/24143* (2013.01); *C12N 2760/10034* (2013.01); *C12N 2760/14134* (2013.01); *C12N 2760/14234* (2013.01)

(58) Field of Classification Search
   CPC ........... C12N 2760/10034; C12N 2760/14134; C12N 2760/14234
   See application file for complete search history.

(56) References Cited

U.S. PATENT DOCUMENTS

| | | |
|---|---|---|
| 2006/0088909 A1 | 4/2006 | Compans et al. |
| 2006/0099225 A1 | 5/2006 | Bavari et al. |
| 2006/0153874 A1 | 7/2006 | Howley |
| 2006/0159706 A1 | 7/2006 | Panicali et al. |
| 2006/0188961 A1 | 8/2006 | Howley et al. |
| 2006/0216702 A1 | 9/2006 | Compans et al. |
| 2008/0193483 A1 | 8/2008 | Moss et al. |
| 2010/0047277 A1 | 2/2010 | Compans et al. |
| 2010/0143402 A1 | 6/2010 | Moss et al. |
| 2010/0196419 A1 | 8/2010 | Compans et al. |
| 2010/0330190 A1 | 12/2010 | Compans et al. |
| 2011/0104199 A1 | 5/2011 | Moss et al. |
| 2011/0262483 A1 | 10/2011 | Haynes et al. |
| 2012/0052082 A1 | 3/2012 | Compans et al. |
| 2012/0219576 A1 | 8/2012 | Branco et al. |
| 2012/0251502 A1 | 10/2012 | Towner et al. |
| 2012/0263750 A1 | 10/2012 | Moss et al. |
| 2012/0289760 A1 | 11/2012 | Hill et al. |
| 2013/0078276 A1 | 3/2013 | Robinson et al. |
| 2013/0101618 A1 | 4/2013 | Sullivan et al. |
| 2014/0255441 A1 | 9/2014 | Compans et al. |
| 2014/0322265 A1 | 10/2014 | Chaplin et al. |
| 2016/0318985 A1 | 11/2016 | Wang et al. |
| 2020/0171141 A1 | 6/2020 | Guirakhoo et al. |

FOREIGN PATENT DOCUMENTS

| | | |
|---|---|---|
| WO | WO 2015/175340 A1 | 11/2015 |
| WO | WO 2016/034678 A2 | 3/2016 |

OTHER PUBLICATIONS

Marzi, A., and H. Feldman, 2014, Ebola virus vaccines: an overview of current approaches, Exp. Rev. Vaccines 13(4):521-531, published online Feb. 27, 2014.*

Raynolds, P., and A. Marzi, 2017, Ebola and Marburg virus vaccines, Virus Genes 53:501-515.*

Meyer, M., et al., Jan. 2019, Can Ebola Virus Vaccines Have Universal Immune Correlates of protection? Trends Microbiol. 27(1):8-16.*

Adu-Gyamfi, E. et al. The Ebola Virus Matrix Protein Penetrates into the Plasma Membrane. J Biol Chem. 288(8): 5779-5789, Feb. 22, 2013.

Baize, S. et al. Lassa virus infection of human dendritic cells and macrophages is productive but fails to activate cells. Journal of Immunology. 172(5):2861-2869, 2004.

Biedenkopf, N. et al. Phosphorylation of Ebola Virus VP30 Influences the Composition of the Viral Nucleocapsid Complex. J Biol Chem. 288(16):11165-11174, 2013.

Cao, W. et al. Identification of dystrolycan as a receptor for lymphocytic choriomeningitis virus and lassa fever virus. Science. 282(5396):2079-2081, 1998.

Carroll, S.A. et al. Molecular evolution of viruses of the family Filoviridae based on 97 whole-genome sequences. J Virol. 87(5):2608-2616, 2013.

Cornu, T.I. et al. Ring Finger Z protein of lymphocytic choriomeningitis virus (LCMV inhibits transcription and RNA replication of an LCMV S-segment minigenome. Journal of Virology. 75(19):9415-9426, 2001.

Djavani, M. et al. Completion of a lassa fever virus sequence and identification of a ring finger open reading frame at the L RNA 5' end. Virology. 235(2):414-418, 1997.

Domi, A. et al. A Single Dose of Modified Vaccina Ankara expressing Ebola Virus-Like Particles Protects Nonhuman Primates from Lethal Ebola Virus Challenge. Scientific Reports. 8(864):1-9, 2018.

European Supplementary Search Report from EP 16737722.5, issued May 16, 2018.

Falzarano, D. et al. Progress in filovirus vaccine development: evaluation potential for clinical use. Exp Rev Vaccines. 10(1):63-77, 2011.

GenBank Accession AFV312002, glycoprotein [Marburg Marburgvirus], Protein—NCBI; 3 pages; 2013.

Hashiguchi, T. et al. Structural Basis for Marburg Virus Neutralization by a Cross-Reactive Human Antibody. Cell. 160(5):904-912, Feb. 26, 2015.

International Search Report from PCT/US2016/013021, dated Mar. 21, 2016.

Kuhn, J.H. et al. Filovirus Ref Seq Entries: Evaluation and Selection of Filovirus Type Variants, Type Sequences, and Names. Viruses. 6(9):3663-3682, 2014.

Kyei, N.N.A. et al. Imported Lassa fever: a report of 2 cases in Ghana. BMC Infectious Diseases. 15(217), 2015.

Lashley, F.R. & Durham, J. Emerging Infectious Diseases: Trends and Issues. Emerg Infect Dis. 9(12):1660, 2002.

Lee, J.E. & Saphire, E.O. Ebolavirus glycoprotein structure and mechanism of entry. Future Virol. 4(6):621-635, 2009.

Mahanty, S. et al. Cutting edge: Impairment of dendritic cells and adaptive immunity by Ebola and Lassa viruses. Journal of Immunology. 170(6):2797-2801, 2003.

Malherbe, D.C. et al. A single immunization with a modified vaccinia Ankara vectored vaccine producing Sudan virus-like particles protects from lethal infection. NPJ Vaccines. 7(1):83, Jul. 25, 2022.

Malherbe, D.C. et al. Modified vaccinia Ankara vaccine expressing Marburg virus-like particles protects guinea pigs from lethal Marburg virus infection. NPJ Vaccines. 78, 2020.

Manuel, E.R. et al. Intergenic region 3 of modified vaccinia ankara is a functional site for insert gene expression and allows for potent antigen-specific immune responses. Virology. 403(2):155-162, Aug. 1, 2010.
Marzi, A. & Feldmann, H. Ebola virus vaccines: an overview of current approaches. Expert Rev Vaccines. 13(4):521-531, 2014.
Mehedi, M. et al. A New Ebola Virus Nonstructural Glycoprotein Expressed through RNA Editing. J. Virol. 85(11):5406-5414, 2011.
Meyer, M. et al. Can Ebola virus vaccines have universal immune correlates of protection? Trends Microbiol. 27(1):8-16, Jan. 2019.
Mittler, E. et al. The Cytoplasmic Domain of Marburg Virus GP Modulates Early Steps of Viral Infection. Journal of Virology. 85(16):8188-8196, Aug. 2011.
Moss, B. et al. Reflections on the early development of poxvirus vectors. Vaccine. 31(39):4220-4222, Sep. 6, 2014.
Nanbo, A. et al. The spatio-temporal distribution dynamics of Ebola virus proteins and RNA in infected cells. Scientific Reports. 3:1206, 2013.

(56) References Cited

OTHER PUBLICATIONS

Orubu, T. et al. Expression and cellular immunogenicity of a transgenic antigen driven by endogenous poxviral early promoters at their authentic loci in MVA. PLOS One. 7(6):e40167, 2012.
Radoshitzky, S.R. et al. Ebolavirus Δ-Peptide Immunoadhesins Inhibit Marburgvirus and Ebolavirus Cell Entry. J Virol. 85(17):8502-8513, Sep. 2011.
Reynolds, P. & Marzi, A. Ebola and Marburg virus vaccines. Virus Genes. 53:501-515, 2017.
Salvato, M. et al. A Single Dose of Modified Vaccinia Ankara Expressing Lassa Virus-like Particles Protects Mice from Lethal Intra-cerebral Virus Challenge. Pathogens. 8:133, 2019.
Sanchez, A. et al. The virion glycoproteins of Ebola viruses are encoded in two reading frames and are expressed through transcriptional editing. PNAS. 93(8):3602-3607, 1996.
Swenson, D.L. et al. Generation of Marburg virus-like particles by co-expression of glycoprotein and matrix protein. FEMS Immunol. Med. Microbiol. 40:27:31, 2004.
Urata, S. & Yasuda, J. Cis- and cell-type-dependent trans-requirements for Lassa virus-like particle production. J Gen Virol. 96(7):1626-1635, 2015.
Wang, Z. et al. Modified H5 promoter improves stability of insert genes while maintaining immunogenicity during extended passage of genetically engineered MVA vaccines. Vaccine. 28(6):1547-1557, Feb. 10, 2010.
Ye, L. et al. Ebola Virus-like particles produced in inspect cells exhibit dendritic cell stimulating activity and induce neutralizing antibodies. Virology. 351:260-270, Aug. 1, 2006.
U.S. Pat. No. 11,701,418, U.S. Appl. No. 15/543,139, Robinson et al., filed Jul. 18, 2023.
U.S. Pat. No. 11,896,657, U.S. Appl. No. 17/584,231, Robinson et al., filed Feb. 13, 2024.
Geddes, Linda, "Everything you need to know about candidate vaccines and treatments for Marburg disease" VaccineWorks, Oct. 2024—available at https://www.gavi.org/vaccineswork/everything-you-need-know-about-candidate-vaccines-and-treatments-marburgdisease#:~:text=At%20least%2028%20vaccine%20candidates%20against%20Marburg,efficacy%2C%20and%20availability%20for%20deployment%20in%20trials. accessed on Feb. 20, 2025.
Glaze, Elizabeth R., et al., "A comparison of the pathogenesis of Marburg virus disease in humans and nonhuman Primates and evaluation of the suitability of these animal models for predicting clinical efficacy under the 'Animal Rule'" Comparative medicine 65.3 (2015): 241-259, Jun. 2015.
Hensley, Lisa E. et al., "Pathogenesis of Marburg hemorrhagic fever in cynomolgus macaques" The Journal of infectious diseases 204. suppl_3, S1021-S1031, 2011.
Presentation: Mary J. Hauser, Ph.D. "Designing and Evaluation of Vaccines against Hemorrhagic Fevers using the MVA-VLP Platform" 2021 World Vaccine & Immunotherapy Congress in San Diego, CA, Dec. 2, 2021.
WHO Technical Advisory Group-candidate vaccine prioritization, Summary of the evaluations and recommendations on the four Marburg vaccines that are candidates for inclusion in the planned "A phase 1/2/3 study to evaluate the safety, tolerability, immunogenicity, and efficacy of vaccine candidates against Marburg disease in healthy individuals at risk of Marburg disease" World Health Organization, Oct. 20, 2024.
Wong, Gary et al., "Immune parameters correlate with protection against ebola virus infection in rodents and nonhuman primates" Science translational medicine 4.158 (2012): 158ra146-158ra146, Oct. 31, 2012.

* cited by examiner

Guinea pigs

Hamsters

```
                          SEQUENCE LISTING

Sequence total quantity: 17
SEQ ID NO: 1              moltype = DNA  length = 2030
FEATURE                   Location/Qualifiers
source                    1..2030
                          mol_type = genomic DNA
                          organism = Ebola virus
SEQUENCE: 1
atgggtgtta caggaatatt gcagttacct cgtgatcgat tcaagaggac atcattcttt   60
ctttgggtaa ttatcctttt ccaaagaaca ttttccatcc cgcttggagt tatccacaat  120
agtacattac aggttagtga tgtcgacaaa ctagtttgtc gtgacaaact gtcatccaca  180
aatcaattga gatcagttgg actgaatctc gaggggaatg gagtggcaac tgacgtgcca  240
tctgtgacta aaagatgggg cttcaggtcc ggtgtcccac caaaggtggt caattatgaa  300
gctggtgaat gggctgaaaa ctgctacaat cttgaaatca aaaaacctga cgggagtgag  360
tgtctaccag cagcgccaga cgggattcgg ggcttccccc ggtgccggta tgtgcacaaa  420
gtatcaggaa cgggaccatg tgccggagac tttgccttcc acaaagaggg tgctttcttc  480
ctgtatgatc gacttgcttc cacagttatc taccgaggaa cgactttcgc tgaaggtgtc  540
gttgcatttc tgatactgcc ccaagctaag aaggacttct tcagctcaca cccccttgaga 600
gagccggtca atgcaacgga ggacccgtcg agtggctatt attctaccac aattagatat  660
caggctaccg gttttggaac taatgagaca gagtacttgt tcgaggttga caatttgacc  720
tacgtccaac ttgaatcaag attcacacca cagtttctgc tccagctgaa tgagacaata  780
tatgcaagtg ggaagaggag caacaccacg ggaaaactaa tttggaaggt caccccgaa   840
attgatacaa caatcgggga gtgggccttc tgggaaacta aaaaaacctc actagaaaaa  900
ttcgcagtga agagttgtct ttcacagctg tatcaaacg acccaaaaac atcagtggtc  960
agagtccggc gcgaacttct tccgacccag agaccaacga acaaatgaa gaccacaaaa 1020
tcatggcttc agaaaattcc tctgcaatgg ttcaagtgca cagtcaagga aggaaagctg 1080
cagtgtcgca tctgacaacc cttgccacaa tctccacgag tcctcaacct cccacaacca 1140
aaacaggtcc ggacaacagc acccataata cacccgtgta taaacttgac atctctgagg 1200
caactcaagt tggacaacat caccgtagag cagacaacga cagcacgcc tccgacactc 1260
cccccgccac gaccgcagcc ggaccccttaa aagcagagaa caccaacacg agtaagagcg 1320
ctgactccct ggacctcgcc accacgacaa gcccccaaaa ctacagcgag actgctggca 1380
acaacaacac tcatccaccaa gataccggag aagagagtgc cagcagcggg aagctaggct 1440
taattaccaa tactattgct ggagtagcag gactgatcac aggcgggaga aggactcgaa 1500
gagaagtaat tgtcaatgct caacccaaat gcaaccccaa tttacattac tggactactc 1560
aggatgaagg tgctgcaatc ggattggcct ggataccata tttcgggcca gcagccgaag 1620
gaatttacac agaggggcta atgcacaacc aagatggttt aatctgtggg ttgaggcagc 1680
tggccaacga aacgactcaa gctctccaac tgttcctgag agccacaact gagctgcgaa 1740
cctttttcaat cctcaaccgt aaggcaattg acttcctgct gcagcgatgg ggtggcacat 1800
gccacatttt gggaccggac tgctgtatcg aaccacatga ttggaccaag aacataacag 1860
acaaaattga tcagattatt catgattttg ttgataaaac ccttccggac caggggggaca 1920
atgacaattg gtggacagga tggagacaat ggataccggc aggtattgga gttacaggtg 1980
ttataattgc agttatcgct ttattctgta tatgcaaatt tgtctttag                2030

SEQ ID NO: 2              moltype = DNA  length = 2031
FEATURE                   Location/Qualifiers
misc_feature              880
                          note = Addition of A nucleotide
source                    1..2031
                          mol_type = other DNA
                          organism = Ebola virus
SEQUENCE: 2
atgggtgtta caggaatatt gcagttacct cgtgatcgat tcaagaggac atcattcttt   60
ctttgggtaa ttatcctttt ccaaagaaca ttttccatcc cgcttggagt tatccacaat  120
agtacattac aggttagtga tgtcgacaaa ctagtttgtc gtgacaaact gtcatccaca  180
aatcaattga gatcagttgg actgaatctc gaggggaatg gagtggcaac tgacgtgcca  240
tctgtgacta aaagatgggg cttcaggtcc ggtgtcccac caaaggtggt caattatgaa  300
gctggtgaat gggctgaaaa ctgctacaat cttgaaatca aaaaacctga cgggagtgag  360
tgtctaccag cagcgccaga cgggattcgg ggcttccccc ggtgccggta tgtgcacaaa  420
gtatcaggaa cgggaccatg tgccggagac tttgccttcc acaaagaggg tgctttcttc  480
ctgtatgatc gacttgcttc cacagttatc taccgaggaa cgactttcgc tgaaggtgtc  540
gttgcatttc tgatactgcc ccaagctaag aaggacttct tcagctcaca cccccttgaga 600
gagccggtca atgcaacgga ggacccgtcg agtggctatt attctaccac aattagatat  660
caggctaccg gttttggaac taatgagaca gagtacttgt tcgaggttga caatttgacc  720
tacgtccaac ttgaatcaag attcacacca cagtttctgc tccagctgaa tgagacaata  780
tatgcaagtg ggaagaggag caacaccacg ggaaaactaa tttggaaggt caccccgaa   840
attgatacaa caatcgggga gtgggccttc tgggaaacta aaaaaaacct cactagaaaa  900
attcgcagtg aagagttgtc tttcacagct gtatcaaacg acccaaaaa catcagtggt   960
cagagtccgg cgcgaacttc ttccgaccca gagaccaaca acaaatga agaccacaaa  1020
atcatggctt cagaaaattc ctctgcaatg gttcaagtgc acagtcaagg aaggaaagct 1080
```

```
gcagtgtcgc atctgacaac ccttgccaca atctccacga gtcctcaacc tcccacaacc  1140
aaaacaggtc cggacaacag cacccataat acaccegtgt ataaacttga catctctgag  1200
gcaactcaag ttggacaaca tcaccgtaga gcagacaacg acagcacagc ctccgacact  1260
cccccegeca cgaccgcagc cggaccctta aaagcagaga acaccaacac gagtaagage  1320
gctgactccc tggacctcgc caccacgaca agccccaaa actacagcga gactgctggc  1380
aacaacaaca ctcatcacca agataccgga gaagagagtg ccagcagcgg gaagctaggc  1440
ttaattacca atactattgc tggagtagca ggactgatca caggcgggag aaggactcga  1500
agagaagtaa ttgtcaatgc tcaacccaaa tgcaacccca atttacatta ctggactact  1560
caggatgaag gtgctgcaat cggattggcc tggataccat atttcgggcc agcagccgaa  1620
ggaatttaca cagagggct aatgcacaac caagatggtt taatctgtgg gttgaggcag  1680
ctggccaacg aaacgactca agctctccaa ctgttcctga gagccacaac tgagctgcga  1740
accttttcaa tcctcaaccg taaggcaatt gacttcctgc tgcagcgatg gggtggcaca  1800
tgccacattt tgggaccgga ctgctgtatc gaaccacatg attggaccaa gaacataaca  1860
gacaaaattg atcagattat tcatgatttt gttgataaaa cccttccgga ccagggggac  1920
aatgacaatt ggtggacagg atggagacaa tggataccgg caggtattgg agttacaggt  1980
gttataattg cagttatcgc tttattctgt atatgcaaat ttgtcttttta g          2031

SEQ ID NO: 3           moltype = AA   length = 676
FEATURE                Location/Qualifiers
source                 1..676
                       mol_type = protein
                       organism = Ebola virus
SEQUENCE: 3
MGVTGILQLP RDRFKRTSFF LWVIILFQRT FSIPLGVIHN STLQVSDVDK LVCRDKLSST   60
NQLRSVGLNL EGNGVATDVP SVTKRWGFRS GVPPKVVNYE AGEWAENCYN LEIKKPDGSE  120
CLPAAPDGIR GFPRCRYVHK VSGTGPCAGD FAFHKEGAFF LYDRLASTVI YRGTTFAEGV  180
VAFLILPQAK KDFFSSHPLR EPVNATEDPS SGYYSTTIRY QATGFGTNET EYLFEVDNLT  240
YVQLESRFTP QFLLQLNETI YASGKRSNTT GKLIWKVNPE IDTTIGEWAF WETKKNLTRK  300
IRSEELSFTA VSNGPKNISG QSPARTSSDP ETNTTNEDHK IMASENSSAM VQVHSQGRKA  360
AVSHLTTLAT ISTSPQPPTT KTGPDNSTHN TPVYKLDISE ATQVGQHHRR ADNDSTASDT  420
PPATTAAGPL KAENTNTSKS ADSLDLATTT SPQNYSETAG NNNTHHQDTG EESASSGKLG  480
LITNTIAGVA GLITGRRTR REVIVNAQPK CNPNLHYWTT QDEGAAIGLA WIPYFGPAAE  540
GIYTEGLMHN QDGLICGLRQ LANETTQALQ LFLRATTELR TFSILNRKAI DFLLQRWGGT  600
CHILGPDCCI EPHDWTKNIT DKIDQIIHDF VDKTLPDQGD NDNWWTGWRQ WIPAGIGVTG  660
VIIAVIALFC ICKFVF                                                   676

SEQ ID NO: 4           moltype = DNA   length = 2031
FEATURE                Location/Qualifiers
source                 1..2031
                       mol_type = other DNA
                       organism = Ebola virus
SEQUENCE: 4
atgggagtaa ctggaattct acaactacca agagatagat tcaaaagaac atctttttt   60
ctatgggtta taattctatt tcaaagaaca ttttctattc cattgggagt aattcataat  120
tctacattgc aagtatctga tgtagataaa ctagtatgta gagataaatt gtctagtaca  180
aatcaactaa gatctgtagg attgaatcta gaaggaaatg gtgtagcgac agatgttcca  240
tctgtaacaa aaagatgggg ttttagatct ggtgtaccac caaaagtagt aaattatgaa  300
gcgggagaat gggcgaaaaa ttgttataat ctagaaatta aaaaaccaga tggatctgaa  360
tgtctaccag cggcgccaga tggaattaga ggatttccaa gatgtagata tgttcataaa  420
gtatctggaa caggaccatg tgcgggagat tttgcgtttc ataagaagg agcatttttt  480
ctatatgata gactagcgtc tacagtaata tatagaggaa caacatttgc ggaaggtgta  540
gtagcttttc taattctacc acaagcgaaa aaagattttt ttagttctca tccactaaga  600
gaaccagtaa atgcgacaga agatccttct tctggatatt attctactac aattagatat  660
caagcgacag gatttggaac aaatgaaaca gaatatctat ttgaagttga taatctaaca  720
tatgtacaac tagaaagtag attcacacca caatttctat tgcaattgaa tgaaacaata  780
tatgcgtctg gaaaaagatc taatacaact ggaaaactaa tttggaaagt aaatccagaa  840
attgatacaa caattggaga atgggctttt tgggaaacaa aaaaaaattt gacaagaaaa  900
attagatctg aagaattgtc ttttacagcg gtatctaatg gaccaaaaaa tatttctgga  960
caatctccag cgagaacttc ttctgatcca gaaacaaata ctacaaatga agatcacaaa 1020
attatggcgt ctgaaaattc ttctgctatg gtacaagtac attctcaagg aagaaaagcg 1080
gcggtatctc atctaacaac actagcgact atttctacat ctccacaacc accaacaaca 1140
aaaactggac cagataatag tacacataat actccagttt ataaactaga tatttctgaa 1200
gcgacacaag ttggacaaca tcatagaaga gcggataatg attctacagc gtctgataca 1260
ccaccagcta caacagctgc tggaccattg aaagcgaaaa aacaaatac ttctaaatct 1320
gcggattctc tagatttggc gacaacaact tctcctcaaa attattctga aacagcggga 1380
aataataata ctcatcatca agatactgga gaagaatctg cgtctagtgg aaaattggga 1440
ctaattacaa atacaattgc gggtgtagcg ggattgatta ctggtggaag aagaactaga 1500
agagaagtaa tagttaatgc gcaacctaaa tgtaatccaa atctacatta ttggacaact 1560
caagatgaag gtgctgcgat tggactagct tggattccat attttggacc tgccgcggaa 1620
ggaatatata ctgaaggact aatgcataat caagatggac taatttgtgg actaagacaa 1680
ctagcgaatg aaactacaca agcgctacaa ctattttga gagcgacaac agaactaaga 1740
acttttagta ttcaaatag aaaagcgatt gatttttgc tacaaagatg gggaggaaca 1800
tgtcatattc taggaccaga ttgttgtatt gaaccacatg attggacaaa aaatattaca 1860
gacaaaattg atcaaattat tcatgatttt gttgataaaa cactaccaga tcaaggagat 1920
aatgataatt ggtggacagg atggagacaa tggattccag cgggaattgg agtaacaggt 1980
gtaattattg cggttattgc gctattttgt atatgtaaat ttgtttttta a          2031

SEQ ID NO: 5           moltype = DNA   length = 2031
FEATURE                Location/Qualifiers
```

-continued

```
source              1..2031
                    mol_type = other DNA
                    organism = Ebola virus
SEQUENCE: 5
atgggagtaa ctggaattct acaactacca agagatagat tcaaaagaac atctttcttt   60
ctatgggtta taattctatt tcaaagaaca ttttctattc cattgggagt aattcataat  120
tctacattgc aagtatctga tgtagataaa ctagtatgta gagataaatt gtctagtaca  180
aatcaactaa gatctgtagg attgaatcta aaggaaatg tgtagcgac agatgttcca    240
tctgtaacaa agagatgggg ttttagatct ggtgtaccac caaaagtagt aaattatgaa  300
gcgggagaat gggcggaaaa ttgttataat ctagaaatta agaaaccaga tggatctgaa  360
tgtctaccag cggcgccaga tggaattaga ggatttccaa gatgtagata tgttcataaa  420
gtatctggaa caggaccatg tgcgggagat tttgcgtttc ataaagaagg agcattcttt  480
ctatatgata gactagcgtc tacagtaata tatagaggaa caacatttgc ggaaggtgta  540
gtagcttttc taattctacc acaagcgaag aaagatttct ttagttctca tccactaaga  600
gaaccagtaa atgcgacaga agatccttct tctggatatt attctactac aattagatat  660
caagcgacag gatttggaac aaatgaaaca gaatatctat ttgaagttga taatctaaca  720
tatgtacaac tagaaagtag attcacacca caatttctat tgcaattgaa tgaaacaata  780
tatgcgtctg gaaagagatc taatacaact ggaaaactaa tttggaaagt aaatccagaa  840
attgatacaa caattggaga atgggctttc tgggaaacaa agaagaattt gacaagaaag  900
attagatctg aagaattgtc ttttacagcg gtatctaatg gaccaaagaa tatttctgga  960
caatctccag cgagaacttc ttctgatcca gaaacaaata ctacaaatga agatcacaaa 1020
attatggcgt ctgaaaattc ttctgctatg gtacaagtac attctcaagg aagaaaagcg 1080
gcggtatctc atctaacaac actagcgact atttctacat ctccacaacc accaacaaca 1140
aagactggac cagataatag tacacataat actccagttt ataaactaga tatttctgaa 1200
gcgacacaag ttgacaaca tcatagaaga gcggataatg attctacagc gtctgataca 1260
ccaccagcta caacagctgc tggaccattg aaagcggaaa atacaaatac ttctaaatct 1320
gcggattctc tagatttggc gacaacaact tctcctcaaa attattctga aacagcggga 1380
aataataata ctcatcatca agatactgga gaagaatctg cgtctagtgg aaaattggga 1440
ctaattacaa atacaattgc gggtgtagcg ggattgatta ctggtggaag aagaactaga 1500
agagaagtaa tagttaatgc gcaacctaaa tgtaatccaa atctacatta ttggacaact 1560
caagatgaag gtgctgcgat tggactagct tggattccat attttggacc tgcggcggaa 1620
ggaatatata ctgaaggact aatgcataat caagatggac taatttgtgg actaagacaa 1680
ctagcgaatg aaactacaca agcgctacaa ctattcttga gagcgacaac agaactaaga 1740
acttttagta ttctaaatag aaaagcgatt gatttcttgc tacaaagatg gggaggaaca 1800
tgtcatattc taggaccaga ttgttgtatt gaaccacatg attggacaaa gaatattaca 1860
gacaaaattg atcaaattat tcatgatttt gttgataaaa cactaccaga tcaaggagat 1920
aatgataatt ggtggacagg atggagacaa tggattccag cgggaattgg agtaacaggt 1980
gtaattattg cggttattgc gctatttgt atatgtaaat ttgtttttta a           2031

SEQ ID NO: 6          moltype = DNA   length = 2041
FEATURE             Location/Qualifiers
source              1..2041
                    mol_type = other DNA
                    organism = Ebola virus
SEQUENCE: 6
atgggagtaa ctggaattct acaactacca agagatagat tcaaaagaac atctttcttt   60
ctatgggtta taattctatt tcaaagaaca ttttctattc cattgggagt aattcataat  120
tctacattgc aagtatctga tgtagataaa ctagtatgta gagataaatt gtctagtaca  180
aatcaactaa gatctgtagg attgaatcta aaggaaatg tgtagcgac agatgttcca    240
tctgtaacaa agagatgggg ttttagatct ggtgtaccac caaaagtagt aaattatgaa  300
gcgggagaat gggcggaaaa ttgttataat ctagaaatta agaaaccaga tggatctgaa  360
tgtctaccag cggcgccaga tggaattaga ggatttccaa gatgtagata tgttcataaa  420
gtatctggaa caggaccatg tgcgggagat tttgcgtttc ataaagaagg agcattcttt  480
ctatatgata gactagcgtc tacagtaata tatagaggaa caacatttgc ggaaggtgta  540
gtagcttttc taattctacc acaagcgaag aaagatttct ttagttctca tccactaaga  600
gaaccagtaa atgcgacaga agatccttct tctggatatt attctactac aattagatat  660
caagcgacag gatttggaac aaatgaaaca gaatatctat ttgaagttga taatctaaca  720
tatgtacaac tagaaagtag attcacacca caatttctat tgcaattgaa tgaaacaata  780
tatgcgtctg gaaagagatc taatacaact ggaaaactaa tttggaaagt aaatccagaa  840
attgatacaa caattggaga atgggctttc tgggaaacaa agaagaattt gacaagaaag  900
attagatctg aagaattgtc ttttacagcg gtatctaatg gaccaaagaa tatttctgga  960
caatctccag cgagaacttc ttctgatcca gaaacaaata ctacaaatga agatcacaaa 1020
attatggcgt ctgaaaattc ttctgctatg gtacaagtac attctcaagg aagaaaagcg 1080
gcggtatctc atctaacaac actagcgact atttctacat ctccacaacc accaacaaca 1140
aagactggac cagataatag tacacataat actccagttt ataaactaga tatttctgaa 1200
gcgacacaag ttgacaaca tcatagaaga gcggataatg attctacagc gtctgataca 1260
ccaccagcta caacagctgc tggaccattg aaagcggaaa atacaaatac ttctaaatct 1320
gcggattctc tagatttggc gacaacaact tctcctcaaa attattctga aacagcggga 1380
aataataata ctcatcatca agatactgga gaagaatctg cgtctagtgg aaaattggga 1440
ctaattacaa atacaattgc gggtgtagcg ggattgatta ctggtggaag aagaactaga 1500
agagaagtaa tagttaatgc gcaacctaaa tgtaatccaa atctacatta ttggacaact 1560
caagatgaag gtgctgcgat tggactagct tggattccat attttggacc tgcggcggaa 1620
ggaatatata ctgaaggact aatgcataat caagatggac taatttgtgg actaagacaa 1680
ctagcgaatg aaactacaca agcgctacaa ctattcttga gagcgacaac agaactaaga 1740
acttttagta ttctaaatag aaaagcgatt gatttcttgc tacaaagatg gggaggaaca 1800
tgtcatattc taggaccaga ttgttgtatt gaaccacatg attggacaaa gaatattaca 1860
gacaaaattg atcaaattat tcatgatttt gttgataaaa cactaccaga tcaaggagat 1920
aatgataatt ggtggacagg atggagacaa tggattccag cgggaattgg agtaacaggt 1980
gtaattattg cggttattgc gctatttgt atatgtaaat ttgtttttta ataatttta   2040
``` t                                                                        2041

SEQ ID NO: 7          moltype = DNA   length = 981
FEATURE               Location/Qualifiers
source                1..981
                      mol_type = genomic DNA
                      organism = Ebola virus
SEQUENCE: 7
atgaggcggg ttatattgcc tactgctcct cctgaatata tggaggccat atacccctgcc   60
aggtcaaatt caacaattgc taggggtggc aacagcaata caggcttcct gacaccggag  120
tcagtcaatg gagacactcc atcgaatcca ctcaggccaa ttgctgatga caccatcgac  180
catgccagcc acacaccagg cagtgtgtca tcagcattca tcctcgaagc tatggtgaat  240
gtcatatcgg gccccaaagt gctaatgaag caaattccaa tttggcttcc tctaggtgtc  300
gctgatcaaa agacctacag ctttgactca actacggccg ccatcatgct tgcttcatat  360
actatcaccc atttcggcaa ggcaaccaat ccgcttgtca gagtcaatcg gctgggtcct  420
ggaatcccgg atcaccccct caggctcctg cgaattggaa accaggcttt cctccaggag  480
ttcgttcttc caccagtcca actacccag tatttcacct tgatttgac agcactcaaa  540
ctgatcactc aaccactgcc tgctgcaaca tggaccgatg acactccaac tggatcaaat  600
ggagcgttgc gtccaggaat ttcatttcat ccaaaacttc gccccattct tttacccaac  660
aaaagtggga agaaggggaa cagtgccgat ctaacatctc cggagaaaat ccaagcaata  720
atgacttcac tccaggactt taagatcgtt ccaattgatc aaccaaaaa tatcatgggt  780
atcgaagtgc cagaaactct ggtccacaag ctgaccggta agaaggtgct ttccaaaaat  840
ggacaaccaa tcatccctgt tcttttgcca aagtacattg ggttggaccc ggtggctcca  900
ggagacctca ccatggtaat cacacaggat tgtgacacgt gtcattctcc tgcaagtctt  960
ccagctgtgg ttgagaagta a                                            981

SEQ ID NO: 8          moltype = DNA   length = 981
FEATURE               Location/Qualifiers
source                1..981
                      mol_type = other DNA
                      organism = Ebola virus
SEQUENCE: 8
atgagaagag taattctacc aacagcgcca ccagaatata tggaagcgat atatccagcg   60
agatctaatt ctacaattgc gagaggtgga aattctaata ctggatttct aacaccagaa  120
tctgtaaatg gagatacacc atctaatcca ctaagaccaa ttgcggatga tacaatagat  180
catgcgagtc atactccagg atctgtatct tctgctttta ttctagaagc tatggttaat  240
gtaatttctg gaccaaaagt actaatgaaa caaattccaa tttggctacc attgggagta  300
gcggatcaaa agacatattc ttttgattct actacagcgg cgattatgct agcgtcttat  360
acaattacac attttggaaa agcgacaaat ccactagtta gagtaaatag actaggacct  420
ggaatacccag atcatccatt gagactacta agaattggaa atcaagcttt tctacaagaa  480
tttgttctac caccagtaca actaccacaa tactttacat ttgatctaac agcgctaaaa  540
ctaattcac aaccattgcc agcggcgaca tggacagatg atacaccaac aggatctaat  600
ggtgctctaa gacctggtat ttcttttcat ccaaaactaa gacctattct attgccaaat  660
aaatctggaa agaaggaaa ttctgcggat ctaacatctc cagaaaagat tcaagcgatt  720
atgacatctc tacaagactt caaaattgta ccaattgatc aacaaagaa tattatggga  780
attgaagtac cagaaacact agttcataaa ctaactggaa agaaagtaac atctaaaaat  840
ggacaaccta ttattccagt attgctacct aaatatattg gactagatcc agtagcgcct  900
ggagatctaa caatggttat tacacaagat tgtgatactt gtcattctcc agcgagtttg  960
cctgcggtag tagaaaaata a                                            981

SEQ ID NO: 9          moltype = DNA   length = 991
FEATURE               Location/Qualifiers
source                1..991
                      mol_type = other DNA
                      organism = Ebola virus
SEQUENCE: 9
atgagaagag taattctacc aacagcgcca ccagaatata tggaagcgat atatccagcg   60
agatctaatt ctacaattgc gagaggtgga aattctaata ctggatttct aacaccagaa  120
tctgtaaatg gagatacacc atctaatcca ctaagaccaa ttgcggatga tacaatagat  180
catgcgagtc atactccagg atctgtatct tctgctttta ttctagaagc tatggttaat  240
gtaatttctg gaccaaaagt actaatgaaa caaattccaa tttggctacc attgggagta  300
gcggatcaaa agacatattc ttttgattct actacagcgg cgattatgct agcgtcttat  360
acaattacac attttggaaa agcgacaaat ccactagtta gagtaaatag actaggacct  420
ggaatacccag atcatccatt gagactacta agaattggaa atcaagcttt tctacaagaa  480
tttgttctac caccagtaca actaccacaa tactttacat ttgatctaac agcgctaaaa  540
ctaattcac aaccattgcc agcggcgaca tggacagatg atacaccaac aggatctaat  600
ggtgctctaa gacctggtat ttcttttcat ccaaaactaa gacctattct attgccaaat  660
aaatctggaa agaaggaaa ttctgcggat ctaacatctc cagaaaagat tcaagcgatt  720
atgacatctc tacaagactt caaaattgta ccaattgatc aacaaagaa tattatggga  780
attgaagtac cagaaacact agttcataaa ctaactggaa agaaagtaac atctaaaaat  840
ggacaaccta ttattccagt attgctacct aaatatattg gactagatcc agtagcgcct  900
ggagatctaa caatggttat tacacaagat tgtgatactt gtcattctcc agcgagtttg  960
cctgcggtag tagaaaaata ataattttta t                                 991

SEQ ID NO: 10         moltype = DNA   length = 5883
FEATURE               Location/Qualifiers
source                1..5883
                      mol_type = other DNA
                      organism = Ebola virus

```
SEQUENCE: 10
gaattcggag tatacgaacc gggaaagaga agatggttaa aaataaagcg agactatttg    60
aacgagggtt ccatggcaga ttctgccgat ttagtagtac taggtgctta ctatggtaaa   120
ggagcaaagg gtggtatcat ggcagtcttt ctaatgggtt gttacgacga tgaatccggt   180
aaatggaaga cggttaccaa gtgttcagga cacgatgata atacgttaag ggagttgcaa   240
gaccaattaa agatgattaa aattaacaag gatcccaaaa aaattccaga gtggttagta   300
gttaataaaa tctatattcc cgattttgta gtagaggatc caaaacaatc tcagatatgg   360
gaaatttcag gagcagagtt tacatcttcc aagtcccata ccgcaaatgg aatatccatt   420
agatttccta gatttactag gataagagag gataaaacgt ggaaagaatc tactcatcta   480
aacgatttag taaacttgac taaatcttaa tttttatggc gcgcctttca ttttgttttt   540
ttctatgcta taaatggtga gcaagggcga ggagctgttc accggggtgg tgcccatcct   600
ggtcgagctg gacggcgacg taaacggcca caagttcagc gtgtccggcg agggcgaggg   660
cgatgccacc tacggcaagc tgaccctgaa gttcatctgc accaccggca agctgccgt   720
gccctggccc accctcgtga ccaccctgac ctacggcgtg cagtgcttca gccgctaccc   780
cgaccacatg aagcagcacg acttcttcaa gtccgccatg cccgaaggct acgtccagga   840
gcgcaccatc ttcttcaagg acgacggcaa ctacaagacc cgcgccgagg tgaagttcga   900
gggcgacacc ctggtgaacc gcatcgagct gaagggcatc gacttcaagg aggacggcaa   960
catcctgggg cacaagctgg agtacaacta caacagccac aacgtctata tcatggccga  1020
caagcagaag aacggcatca aggtgaactt caagatccgc cacaacatcg aggacggcag  1080
cgtgcagctc gccgaccact accagcagaa caccccccatc ggcgacggcc ccgtgctgct  1140
gcccgacaac cactacctga gcacccagtc cgccctgagc aaagacccca cgagaagcg  1200
cgatcacatg gtcctgctgg agttcgtgac cgccgccggg atcactctcg gcatgcacga  1260
gctgtacaag taagagctcc ccgattttgt agtagaggat ccaaaacaat ctcagatatg  1320
ggaaatttca ggagcagagt ttacatcttc caagtcccat accgcaaatg gaatatccat  1380
tagatttcct agatttacta ggataagaga ggataaaacg tggaaagaat ctactcatct  1440
aaacgattta gtaaacttga taaatcttaa ttttttatcc cgaggccgct ggtacccaac  1500
ctaaaaattg aaaataaata caaggttctt gagggttgt gttaaattga agcgagaaa  1560
taatcataaa taagcccggg atgagaagag taattctacc aacagcgcca ccagaatata  1620
tggaagcgat atatccagcg agatctaatt ctacaattgc gagaggtgga aattctaata  1680
ctggatttct aacaccagaa tctgtaaatg gagatacacc atctaatcca ctaagaccaa  1740
ttgcggatga tacaatagat catgcgagtc atactccagg atctgtatct tctgctttta  1800
ttctagaagc tatggttaat gtaatttctg gaccaaaagt actaatgaaa caaattccaa  1860
tttggctacc attgggagta gcggatcaaa agacatattc ttttgattct actacagcgg  1920
cgattatgct agcgtcttat acaattacac attttgaaaa agcgacaaat ccactagtta  1980
gagtaaatag actaggacct ggaataccag atcatccatt gagactacta agaattggaa  2040
atcaagcttt tctacaagaa tttgttctac caccagtaca actaccacaa tactttacat  2100
ttgatctaac agcgctaaaa ctaattacac aaccattgcc agcggcgaca tggacagatg  2160
atacaccaac aggatctaat ggtgctctaa gacctggtat ttcttttcat ccaaaactaa  2220
gacctattct attgccaaat aaatctgaaa agaaagaaa ttctgcggat ctaacatctc  2280
cagaaaagat tcaagcgatt atgacatctc tacaagactt caaaattgta ccaattgatc  2340
caacaaagaa tattatggga attgaagtac cagaaacact agttcataaa ctaactggaa  2400
agaaagtaac atctaaaaat ggacaaccta ttattccagt attgctacct aaatatattg  2460
gactagatcc agtagcgcct ggagatctaa caatggttat tacacaagat tgtgatactt  2520
gtcattctcc agcgagtttg cctgcgctag tagaaaaata ataattttta tgtcgacctg  2580
cagctaatgt attagttaaa tattaaaact taccacgtaa aacttaaaat ttaaaatgat  2640
atttcattga cagatagatc acacattatg aactttcaag gacttgtgtt aactgacaat  2700
tgcaaaaatc aatgggtcgt tggaccatta ataggaaaag gtggatttgg tagtatttat  2760
actactaatg acaataatta tgtagtaaaa atagagccca aagctaacgg atcattattt  2820
accgaacagg cattttatac tagagtactt aaaccatccg ttatcgaaga atggaaaaaa  2880
tctcacaata taaagcacgt aggtcttatc acgtgcaagg catttggtct atacaaatcc  2940
attaatgtgg aatatcgatt cttggtatt aatagattag tgcagatct agatgcggtg  3000
atcagagcca ataataatag attaccaaaa aggtcggtga tgttgatcgg aatcgaaatc  3060
ttaaatacca tacaattat gcacgagcaa ggatattctc acggagatat taaagcgagt  3120
aatatagtct tggatcaaat agataagaat aaattatatc tagtggatta cggattggtt  3180
tctaaattca tgtccaagctt gtctccctat agtgagtcgt attagagctt ggcgtaatca  3240
tggtcatagc tgtttcctgt gtgaaattgt tatccgctca caattccaca caacatacga  3300
gccgaagca taagtgtaa agcctggggt gcctaatgag tgagctaact cacattaatt  3360
gcgttgcgct cactgcccgc tttcgagtcg gaaacctgt cgtgccagct gcattaatga  3420
atcggccaac gcgcggggag aggcggtttg cgtattgggc gctcttccgc ttcctcgctc  3480
actgactcgc tgcgctcgt cgttcggctg cggcgagcgg tatcagctca ctcaaaggcg  3540
gtaatacggt tatccacaga atcagggat aacgcaggaa agaacatgtg agcaaaaggc  3600
cagcaaaagg ccaggaaccg taaaaaggcc gcgttgctgg cgttttcga taggctccgc  3660
ccccctgacg agcatcacaa aaatcgacgc tcaagtcaga ggtggcgaaa cccgacagga  3720
ctataaagat accaggcgtt tccccctgga agctccctcg tgttccgacc  3780
ctgccgctta ccggatacct gtccgccttt ctcccttcgg gaagcgtggc gctttctcat  3840
agctcacgct gtaggtatct cagttcggtg taggtcgttc gctccaagct gggctgtgtg  3900
cacgaacccc ccgttcagcc cgaccgctgc gccttatccg gtaactatcg tcttgagtcc  3960
aacccggtaa gacacgactt atcgccactg gcagcagcca ctggtaacag gattagcaga  4020
gcgaggtatg taggcggtgc tacagagttc ttgaagtggt ggcctaacta cggctacact  4080
agaaggacag tatttggtat ctgcgctctg ctgaagccag ttaccttcgg aaaaagagtt  4140
ggtagctctt gatccggcaa acaaaccacc gctggtagcg gtggtttttt tgtttgcaag  4200
cagcagatta cgcgcagaaa aaaaggatct caagaagatc ctttgatctt ttctacgggg  4260
tctgacgctc agtggaacga aaactcacgt taagggattt tggtcatgag attatcaaaa  4320
aggatcttca cctagatcct tttaaattaa aaatgaagtt ttaaatcaat ctaaagtata  4380
tatgagtaaa cttggtctga cagttaccaa tgcttaatca gtgaggcacc tatctcagcg  4440
atctgtctat ttcgttcatc catagttgcc tgactccccg tcgtgtagat aactacgata  4500
cgggagggct taccatctgg ccccagtgct gcaatgatac cgcgagaccc acgctcaccg  4560
gctccagatt tatcagcaat aaaccagcca gccgaaggg ccgagcgcag aagtggtcct  4620
gcaactttat ccgcctccat ccagtctatt aattgttgcc gggaagctag agtaagtagt  4680
```

```
tcgccagtta atagtttgcg caacgttgtt ggcattgcta caggcatcgt ggtgtcacgc 4740
tcgtcgtttg gtatggcttc attcagctcc ggttcccaac gatcaaggcg agttacatga 4800
tcccccatgt tgtgcaaaaa agcggttagc tccttcggtc ctccgatcgt tgtcagaagt 4860
aagttggccg cagtgttatc actcatggtt atggcagcac tgcataattc tcttactgtc 4920
atgccatccg taagatgctt ttctgtgact ggtgagtact caaccaagtc attctgagaa 4980
tagtgtatgc ggcgaccgag ttgctcttgc ccggcgtcaa tacgggataa taccgcgcca 5040
catagcagaa ctttaaaagt gctcatcatt ggaaaacgtt cttcggggcg aaaactctca 5100
aggatcttac cgctgttgag atccagttcg atgtaaccca ctcgtgcacc caactgatct 5160
tcagcatctt ttactttcac cagcgtttct gggtgagcaa aaacaggaag gcaaaatgcc 5220
gcaaaaaagg gaataagggc gacacggaaa tgttgaatac tcatactctt ccttttcaa 5280
tattattgaa gcatttatca gggttattgt ctcatgagcg gatacatatt tgaatgtatt 5340
tagaaaaata aacaaatagg ggttccgcgc acatttcccc gaaaagtgcc acctgacgtc 5400
taagaaacca ttattatcat gacattaacc tataaaaata ggcgtatcac gaggcccttt 5460
cgtctcgcgc gtttcggtga tgacggtgaa aacctctgac acatgcagct cccggagacg 5520
gtcacagctt gtctgtaagc ggatgccggg agcagacaag cccgtcaggg cgcgtcagcg 5580
ggtgttggcg ggtgtcgggg ctggcttaac tatgcggcat cagagcagat tgtactgaga 5640
gtgcaccata tgcggtgtga ataccgcac agatgcgtaa ggagaaaata ccgcatcagg 5700
cgccattcgc cattcaggct gcgcaactgt tgggaagggc gatcggtgcg ggcctcttcg 5760
ctattacgcc agctggcgaa agggggatgt gctgcaaggc gattaagttg ggtaacgcca 5820
gggttttccc agtcacgacg ttgtaaaacg acggccagtg aattggattt aggtgacact 5880
ata                                                                 5883

SEQ ID NO: 11           moltype = DNA   length = 7074
FEATURE                 Location/Qualifiers
source                  1..7074
                        mol_type = other DNA
                        organism = Ebola virus
SEQUENCE: 11
gaattccctg ggacatacgt atatttctat gatctgtctt atatgaagtc tatacagcga 60
atagattcag aatttctaca taattatata ttgtacgcta ataagtttaa tctaacactc 120
cccgaagatt tgtttataat ccctacaaat ttggatattc tatggcgtac aaaggaatat 180
atagactcgt tcgatattag tacagaaaca tggaataaat tattatccaa ttattatatg 240
aagatgatag agtatgctaa actttatgta ctaagtccta ttctcgctga ggagttggat 300
aattttgaga ggacgggaga attaactagt attgtacaag aagccatttt atctctaaat 360
ttacgaatta agatttttaaa ttttaaacat aaagatgatg atacgtatat cactttttgt 420
aaaatattat tcggtgtcta taacggaaca aacgctacta tatattatca tagacctcta 480
acgggatata tgaatatgat ttcagatact atatttgttc ctgtagataa taactaaggc 540
gcgcctttca ttttgttttt ttctatgcta taaatggtga gcaagggcga ggagctgttc 600
accggggtgg tgcccatcct ggtcgagctg gacggcgacg taaacggcca caagttcagc 660
gtgtccggcg agggcgaggg cgatgccacc tacggcaagc tgaccctgaa gttcatctgc 720
accaccggca agctgcccgt gccctggccc accctcgtga ccaccctgac ctacggcgtg 780
cagtgcttca gccgctaccc cgaccacatg aagcagcacg acttcttcaa gtccgccatg 840
cccgaaggct acgtccagga gcgcaccatc ttcttcaagg acgacggcaa ctacaagacc 900
cgcgccgagg tgaagttcga gggcgacacc ctggtgaacc gcatcgagct gaagggcatc 960
gacttcaagg aggacggcaa catcctgggg cacaagctgg agtacaacta caacagccac 1020
aacgtctata tcatggccga caagcagaag aacggcatca aggtgaactt caagatccgc 1080
cacaacatcg aggacggcag cgtgcagctc gccgaccact accagcagaa cacccccatc 1140
ggcgacggcc ccgtgctgct gcccgacaac cactacctga gcacccagtc cgccctgagc 1200
aaagacccca acgagaagcg cgatcacatg gtcctgctgg agttcgtgac cgccgccggg 1260
atcactctcg gcatgcacga gctgtacaag taagagctcg aggacgggag aattaactag 1320
tattgtacaa gaagccattt tatctctaaa tttacgaatt aagattttaa attttaaaca 1380
taaagatgat gatacgtata tacttttttg taaaatatta ttcggtgtct ataacgaaac 1440
aaacgctact atatattatc atagacctct aacgggatat atgaatatga tttcagatac 1500
tatatttgtt cctgtagata taactaact cgaggccgct ggtacccaac ctaaaaattg 1560
aaaataaata caaaggttct tgagggttgt gttaaattga aagcgagaaa taatcataaa 1620
taagcccggg atgggagtaa ctggaattct acaactacca agagatagat tcaaagaac 1680
atctttcttt ctatgggtta taattctatt tcaaagaaca ttttctattc cattgggagt 1740
aattcataat tctacattgc aagtatctga tgtagataaa ctagtatgta gagatataatt 1800
gtctagtaca aatcaactaa gatctgtagg attgaatcta gaaggaaatg gtgtagcgac 1860
agatgttcca tctgtaacaa agagatgggg ttttagatct ggtgtaccac caaaagtagt 1920
aaattatgaa gcgggagaat gggcggaaaa ttgttataat ctagaaatta gaaaccaga 1980
tggatctgaa tgtctaccag cggcgccaga tggaattaga ggatttccaa gatgtagata 2040
tgttcataaa gtatctggaa caggaccatg tgcgggagat tttgcgtttc ataagaagg 2100
agcattcttt ctatatgata gactagcgtc tacagtaata tatagaggaa caacatttgc 2160
ggaaggtgta gtagcttttc taattctacc acaagcgaag aaagattct ttagttctca 2220
tccactaaga gaaccagtaa atgcgacaga agatccttct tctggatatt attctactac 2280
aattagatat caagcgacag gatttggaac aaatgaaaca gaatatctat ttgaagttga 2340
taatctaaca tatgtacaac tagaaagtag attcacacca caatttctat gcaattgaa 2400
tgaaacaata tatgcgtctg gaaagatctc taatacaact ggaaaactaa tttggaaagt 2460
aaatccagaa attgatacaa caattggaga atgggctttc tgggaaacaa agaagaattt 2520
gacaagaaag attagatctg aagaattgtc ttttacagcg gtatcaatg gaccaaagaa 2580
tatttctgga caatctccag cgagaacttc ttctgatcca gaaacaaata ctacaaatga 2640
agatcacaaa attatgggcgt ctgaaaattc ttctgctatg gtacaagtac attctcaagg 2700
aagaaaagcg gcgtatctc atctaacaac actagcgtc attctacat ctccacaacc 2760
accaacaaca aagactggac cagataatag tacacataat actccagttt ataaactaga 2820
tatttctgaa gcgacacaag ttggacaaca tcatagaaga gcggataatg attctacagc 2880
gtctgataca ccaccagcta caacagctgc tggaccattg aaagcggaaa atacaaatac 2940
ttctaaatct gcggattctc tagattggc gacaacaact tctcctcaaa attattctga 3000
aacagcggga ataataataa ctcatcatca agatactgga gaagaatctg cgtctagtgg 3060
```

```
aaaattggga ctaattacaa atacaattgc gggtgtagcg ggattgatta ctggtggaag  3120
aagaactaga agagaagtaa tagttaatgc gcaacctaaa tgtaatccaa atctacatta  3180
ttggacaact caagatgaag gtgctgcgat tggactagct tggattccat attttggacc  3240
tgcggcggaa ggaatatata ctgaaggact aatgcataat caagatggac taatttgtgg  3300
actaagacaa ctagcgaatg aaactacaca agcgctacac ctattcttga gagcgacaac  3360
agaactaaga acttttagta ttctaaatag aaaagcgatt gatttcttgc tacaaagatg  3420
gggaggaaca tgtcatattc taggaccaga ttgttgtatt gaaccacatg attggacaaa  3480
gaatattaca gacaaaattg atcaaattat tcatgatttt gttgataaaa cactaccaga  3540
tcaaggagat aatgataatt ggtggacaga atggagacaa tggattccag cgggaattgg  3600
agtaacaggt gtaattattg cggttattgc gctattttgt atatgtaaat ttgttttta  3660
ataatttta tgtcgacctg cagtcaaact ctaatgacca catctttttt tagagatgaa  3720
aaatttccca catctccttt tgtagacacg actaaacatt ttgcagaaaa aagtttatta  3780
gtgttagat aatcgtatac ttcatcagtg tagatagtaa atgtgaacag ataaaaggta  3840
ttcttgctca atagattggt aaattccata gaatatatta atcctttctt cttgagatcc  3900
cacatcattt caaccagaga cgttttatcc aatgatttac ctcgtactat accacataca  3960
aaactagatt ttgcagtgac gtcgtatctg gtattcctac caaacaaaat tttacttta  4020
gttcttttag aaaattctaa ggtagaatct ctatttgcca atatgtcatc tatggaatta  4080
ccactagcaa aaaatgatag aaatatat tgatacatcg cagctggttt tgatctacta  4140
tactttaaaa acgaatcaga ttccataatt gcctgtatat catcagctga aaaactatgt  4200
tttacacgta ttccttcggc atttcttttt aatgatatat cttgtttaga caatgataaa  4260
gttatcatgt ccatgagaga cgcgtctccg tatcgtataa atatttcatt agatgttaga  4320
cgcttcatta ggggtatact tctataaggt ttcttaatca gtccatcatt ggttgcgtca  4380
agaacaagct tgtctcccta tagtgagtcg tattagagct tggcgtaatc atggtcatag  4440
ctgtttcctg tgtgaaattg ttatccgctc acaattccac acaacatacg agccggaagc  4500
ataaagtgta aagcctgggg tgcctaatga gtgagctaac tcacattaat tgcgttgcgc  4560
tcactgcccg ctttcgagtc gggaaaacct gtcgtgccag tgcattaatg aatcgccaa  4620
cgcgcgggga gaggcggttt gcgtattggg cgctcttccg cttcctcgct cactgactcg  4680
ctgcgctcgg tcgttcggct gcggcgagcg gtatcagctc actcaaaggc ggtaatacgg  4740
ttatccacag aatcagggga taacgcagga agaacatgt gagcaaaagg ccagcaaaag  4800
gccaggaacc gtaaaaaggc cgcgttgctg gcgtttttcc ataggctccg ccccctgac  4860
gagcatcaca aaaatcgacg ctcaagtcag aggtggcgaa acccgacagg actataaaga  4920
taccaggcgt ttccccctgg aagctccctc gtgcgctctc ctgttccgac cctgccgctt  4980
accggatacc tgtccgcctt tctccttcg ggaagcgtgg cgctttctca tagctcacgc  5040
tgtaggtatc tcagttcggt gtaggtcgtt cgctccaagc tgggctgtgt gcacgaaccc  5100
cccgttcagc ccgaccgctg cgccttatcc ggtaactatc gtcttgagtc caacccggta  5160
agacacgact tatcgccact ggcagcagcc actggtaaca ggattagcag agcgaggtat  5220
gtaggcggtg ctacagagtt cttgaagtgg tggcctaact acggctacac tagaaggaca  5280
gtatttggta tctgcgctct gctgaagcca gttaccttcg gaaaaagagt tggtagctct  5340
tgatccggca aacaaaccac cgctggtagc ggtggttttt ttgtttgcaa gcagcagatt  5400
acgcgcagaa aaaaaggatc tcaagaagat cctttgatct tttctacggg gtctgacgct  5460
cagtggaacg aaaactcacg ttaagggatt ttggtcatga gattatcaaa aaggatcttc  5520
acctagatcc ttttaaatta aaaatgaagt tttaaatcaa tctaaagtat atatgagtaa  5580
acttggtctg acagttacca atgcttaatc agtgaggcac ctatctcagc gatctgtcta  5640
tttcgttcat ccatagttgc ctgactcccc gtcgtgtaga taactacgat acgggagggc  5700
ttaccatctg gccccagtgc tgcaatgata ccgcgagacc cacgctcacc ggctccagat  5760
ttatcagcaa taaaccagcc agccggaagg gccgagcgca gaagtggtcc tgcaacttta  5820
tccgcctcca tccagtctat taattgttgc cgggaagcta gagtaagtag ttcgccagtt  5880
aatagtttgc gcaacgttgt tggcattgct acaggcatcg tggtgtcacg ctcgtcgttt  5940
ggtatggctt cattcagctc cggttcccaa cgatcaaggc gagttacatg atcccccatg  6000
ttgtgcaaaa aagcggttag ctccttcggt cctccgatcg ttgtcagaag taagttggcc  6060
gcagtgttat cactcatggt tatggcagca ctgcataatt ctcttactgt catgccatcc  6120
gtaagatgct tttctgtgac tggtgagtac tcaaccaagt cattctgaga atagtgtatg  6180
cggcgaccga gttgctcttg cccggcgtca tacgggata taccgcgcc acatagcaga  6240
actttaaaag tgctcatcat tggaaaacgt tcttcgggc gaaactctc aaggatctta  6300
ccgctgttga tccagttc gatgtaaccc actcgtgcac ccaactgatc ttcagcatct  6360
tttactttca ccagcgtttc tgggtgagca aaaacaggaa ggcaaaatgc cgcaaaaaag  6420
ggaataaggg cgacacggaa atgttgaata ctcatactct tcctttttca atattattga  6480
agcatttatc agggttattg tctcatgagc ggatacatat ttgaatgtat ttagaaaaat  6540
aaacaaatag gggttccgcg cacatttccc cgaaaagtgc cacctgacgt ctaagaaacc  6600
attattatca tgacattaac ctataaaaat aggcgtatca cgaggccctt tcgtctcgcg  6660
cgtttcggtg atgacggtga aaacctctga cacatgcagc tcccggagac ggtcacagct  6720
tgtctgtaag cggatgccgg gagcagacaa gcccgtcagg gcgcgtcagc gggtgttggc  6780
gggtgtcggg gctggcttaa ctatgcggca tcagagcaga ttgtactgag agtgcaccat  6840
atgcggtgtg aaataccgca cagatgcgta aggagaaaat accgcatcag gcgccattcg  6900
ccattcaggc tgcgcaactg ttgggaaggg cgatcggtgc gggcctcttc gctattacgc  6960
cagctggcga aagggggatg tgctgcaagg cgattaagtt gggtaacgcc agggttttcc  7020
cagtcacgac gttgtaaaac gacggccagt gaattggatt taggtgacac tata        7074

SEQ ID NO: 12        moltype = DNA   length = 5876
FEATURE              Location/Qualifiers
source               1..5876
                     mol_type = other DNA
                     organism = Ebola virus
SEQUENCE: 12
gaattcggag tatacgaacc gggaaagaga agatggttaa aaataaagcg agactatttg   60
aacgagggtt ccatggcaga ttctgccgat ttagtagtac taggtgctta ctatggtaaa  120
ggagcaaagg gtggtatcat ggcagtcttt ctaatgggtt gttacgacga tgaatccggt  180
aaatggaaga cggttaccaa gtgttcagga cacgatgata atacgttaag ggagttgcaa  240
gaccaattaa agatgattaa aattaacaag gatcccaaaa aaattccaga gtggttagta  300
```

```
gttaataaaa tctatattcc cgattttgta gtagaggatc caaaacaatc tcagatatgg    360
gaaatttcag gagcagagtt tacatcttcc aagtcccata ccgcaaatgg aatatccatt    420
agatttccta gatttactag gataagagag gataaaacgt ggaaagaatc tactcatcta    480
aacgatttag taaacttgac taaatcttaa tttttatggc gcgcctttca ttttgttttt    540
ttctatgcta taaatggtga gcaagggcga ggagctgttc accggggtgg tgcccatcct    600
ggtcgagctg gacggcgacg taaacggcca caagttcagc gtgtccggcg agggcgaggg    660
cgatgccacc tacggcaagc tgaccctgaa gttcatctgc accaccggca agctgcccgt    720
gcccctggcc cccctcgtga ccaccctgac ctacggcgtg cagtgcttca gccgctaccc    780
cgaccacatg aagcagcacg acttcttcaa gtccgccatg cccgaaggct acgtccagga    840
gcgcaccatc ttcttcaagg acgacggcaa ctacaagacc cgcgccgagg tgaagttcga    900
gggcgacacc ctggtgaacc gcatcgagct gaagggcatc gacttcaagg aggacggcaa    960
catcctgggg cacaagctgg agtacaacta caacagccac aacgtctata tcatggccga   1020
caagcagaag aacggcatca aggtgaactt caagatccgc cacaacatcg aggacggcag   1080
cgtgcagctc gccgaccact accagcagaa caccccatc ggcgacggcc ccgtgctgct   1140
gcccgacaac cactacctga gcacccagtc cgccctgagc aaagacccca cgagaagcg   1200
cgatcacatg gtcctgctgg agttcgtgac cgccgcgggg atcactctcg gcatgcacga   1260
gctgtacaag taagagctcc ccgatttgt agtagaggat ccaaaacaat ctcagatatg   1320
ggaaatttca ggagcagagt ttacatcttc caagtcccat accgcaaatg gaatatccat   1380
tagatttcct agatttacta ggataagaga ggataaaacg tggaaagaat ctactcatct   1440
aaacgattta gtaaacttga ctaaatctta atttttatct cgaggccgct ggtacccaac   1500
ctaaaaattg aaaataaata caaggttct tgagggttgt gttaaattga aagcgagaaa   1560
taatcataaa taagcccggg atgaaaagag taacagtacc aacagcgcca ccagcgtatg   1620
cggatatagg atatccaatg tctatgctac ctattaaatc ttctagagcg gtatctggaa   1680
ttcaacaaaa gcaagaagta ctacctggaa tggatacacc atctaattct atgagaccag   1740
tagcggatga taatattgat catacttctc atactccaaa tggtgtagcg tctgctttta   1800
ttctagaagc gacagtaaat gtaatttctg gaccaaaagt actaatgaac caaattccaa   1860
tttggctacc actaggaatt gcggatcaaa agacatattc ttttgattct acaacagcgg   1920
cgattatgct agcgtcttat acaattacac attttggaaa agcgataat ccactagtta   1980
gagtaaaatag actaggacaa ggaataccag atcatccact aagactacta agaatgggaa   2040
atcaagcttt tctacaagaa tttgttctac caccagtaca actaccacaa tactttacat   2100
ttgatctaac agcgctaaaa ctagtaacac aaccactacc agcggcgaca tggacagatg   2160
aaactccatc taatctaagt ggtgctctaa gaccaggact atcttttcat ccaaaactaa   2220
gacctgtact actaccagga aagactgaa agaaaggaca tgtatctgat ttgacagcgc   2280
cagacaaaat tcaaacaata gtaaatctaa tgcaagactt caaaattgta ccaattgatc   2340
cagcgaaatc tattattgga attgaagtac cagaactact agttcataaa ttgactggaa   2400
agaaaatgtc tcaaaagaat ggacaaccta ttattccagt actattgcct aaatatattg   2460
gtctagatcc tattctcct ggagatcaa caatggttat tacaccagat tatgatgatt   2520
gtcattctcc agcgtcttgt tcttatctat ctgaaaagta ataagtcgac ctgcagctaa   2580
tgtattagtt aaatattaaa acttaccacg taaaacttaa aattttaaat gatatttcat   2640
tgacagatag atcacacatt atgaactttc aaggacttgt gttaactgac aattgcaaaa   2700
atcaatgggt cgttggacca ttaataggaa aaggtggatt tggtagtatt tatactacta   2760
atgacaataa ttatgtagta aaaatagagc ccaaagctaa cggatcatta tttaccgaac   2820
aggcatttta tactagagta cttaaaccat ccgttatcga agaatggaaa aaatctcaca   2880
atataaagca cgtaggtctt atcacgtgca aggcatttgg tctatacaaa tccattaatg   2940
tggaatatcg attcttggta attaatagat taggtcaga tctagatgcg gtgatcagag   3000
ccaataataa tagattacca aaaaggtcgg tgatgttgat cggaatcgaa atcttaaata   3060
ccatacaatt tatgcacgag caaggatatt ctcacggaga tattaaagcg agtaatatag   3120
tcttggatca aatagataag aataaattat atctcagtgga ttacggattg gtttctaaat   3180
tcatgtcaag cttgtctccc tatagtgagt cgtattagag cttggcgtaa tcatggtcat   3240
agctgttttc tgtgtgaaat tgttatccgc tcacaattcc acacaacata cgagccggaa   3300
gcataaagtg taaagcctgg ggtgcctaat gagtgagcta actcacatta attgcgttgc   3360
gctcactgcc cgctttcgag tcggaaacc tgtcgtgcca gctgcattaa tgaatcggcc   3420
aacgcgcggg gagaggcggt ttgcgtattg ggcgctcttc cgcttcctcg ctcactgact   3480
cgctgcgctc ggtcgttcgg ctgcggcgag cggtatcagc tcactcaaag gcggtaatac   3540
ggttatccac agaatcaggg gataacgcag gaaagaacat gtgagcaaaa ggccagcaaa   3600
aggccaggaa ccgtaaaaag gccgcgttgc tggcgttttt cgataggctc cgcccccctg   3660
acgagcatca caaaaatcga cgctcaagtc agaggtggcg aaacccgaca ggactataaa   3720
gataccaggc gtttccccct ggaagctccc tcgtgcgctc tcctgttccg accctgccgc   3780
ttaccggata cctgtccgcc tttctccctt cgggaagcgt ggcgctttct catgctcac   3840
gctgtaggta tctcagttcg gtgtaggtcg ttcgctccaa gctgggctgt gtgcacgaac   3900
cccccgttca gcccgaccgc tgcgccttat ccggtaacta tcgtcttgag tccaacccgg   3960
taagacacga cttatcgcca ctggcagcag ccactggtaa caggattagc agagcgaggt   4020
atgtaggcgg tgctacagag ttcttgaagt ggtggcctaa ctacggctac actagaagga   4080
cagtatttgg tatctgcgct ctgctgaagc cagttacctt cggaaaaaga gttggtagct   4140
cttgatccgg caaacaaacc accgctggta gcggtggttt ttttgtttgc aagcagcaga   4200
ttacgcgcag aaaaaaagga tctcaagaag atcctttgat cttttctacg ggtctgacg   4260
ctcagtggaa cgaaaactca cgttaaggga ttttggtcat gagattatca aaaaggatct   4320
tcacctagat ccttttaaat taaaaatgaa gttttaaatc aatctaaagt atatatgagt   4380
aaacttggtc tgacagttac caatgcttaa tcagtgaggc acctatctca gcgatctgtc   4440
tatttcgttc atccatagtt gcctgactcc ccgtcgtgta gataactacg atacgggagg   4500
gcttaccatc tggccccagt gctgcaatga taccgcgaga cccacgctca ccggctccag   4560
atttatcagc aataaaccag ccagccgaa gggccgagcg cagaagtggt cctgcaactt   4620
tatccgcctc catccagtct attaattgtt gccgggaagc tagagtaagt agttcgccag   4680
ttaatagttt gcgcaacgtt gttgccattg ctacaggcat cgtggtgtca cgctcgtcgt   4740
ttggtatggc ttcattcagc tccggttccc aacgatcaag gcgagttaca tgatccccca   4800
tgttgtgcaa aaaagcggtt agctccttcg gtcctccgat cgttgtcaga agtaagttgg   4860
ccgcagtgtt atcactcatg gttatggcag cactgcataa ttctcttact gtcatgccat   4920
ccgtaagatg cttttctgtg actggtgagt actcaaccaa gtcattctga gaatagtgta   4980
tgcggcgacc gagttgctct tgcccggcgt caatacggga taataccgcg ccacatagca   5040
```

```
gaactttaaa agtgctcatc attggaaaac gttcttcggg gcgaaaactc tcaaggatct   5100
taccgctgtt gagatccagt tcgatgtaac ccactcgtgc acccaactga tcttcagcat   5160
cttttacttt caccagcgtt tctgggtgag caaaaacagg aaggcaaaat gccgcaaaaa   5220
agggaataag ggcgacacgg aaatgttgaa tactcatact cttcctttt caatattatt    5280
gaagcatttt tcagggttat tgtctcatga gcggatacat ttgaatgt atttagaaaa     5340
ataaacaaat aggggttccg cgcacatttc cccgaaaagt gccacctgac gtctaagaaa   5400
ccattattat catgacatta acctataaaa ataggcgtat cacgaggccc tttcgtctcg   5460
cgcgtttcgg tgatgacggt gaaaacctct gacacatgca gctcccggag acggtcacag   5520
cttgtctgta agcggatgcc gggagcagac aagcccgtca gggcgcgtca gcgggtgttg   5580
gcgggtgtcg gggctggctt aactatgcgg catcagagca gattgtactg agagtgcacc   5640
atatgcggtg tgaaataccg cacagatgcg taaggagaaa ataccgcatc aggcgccatt   5700
cgccattcag gctgcgcaac tgttgggaag ggcgatcgt gcgggcctct tcgctattac    5760
gccagctggc gaaaggggga tgtgctgcaa ggcgattaag ttgggtaacg ccagggtttt   5820
cccagtcacg acgttgtaaa acgacggcca gtgaattgga tttaggtgac actata       5876
```

SEQ ID NO: 13         moltype = DNA   length = 7067
FEATURE               Location/Qualifiers
source                1..7067
                        mol_type = other DNA
                        organism = Ebola virus
SEQUENCE: 13

```
gaattccctg ggacatacgt atatttctat gatctgtctt atatgaagtc tatacagcga    60
atagattcag aatttctaca taattatata ttgtacgcta ataagtttaa tctaacactc   120
cccgaagatt tgtttataat ccctacaaat ttggatattc tatggcgtac aaaggaatat   180
atagactcgt tcgatattag tacagaaaca tggaataaat tattatccaa ttattatatg   240
aagatgatag agtatgctaa actttatgta ctaagtccta ttctcgctga ggagttggat   300
aattttgaga ggacgggaga attaactagt attgtacaag aagccatttt atctctaaat   360
ttacgaatta agattttaaa ttttaaacat aaagatgatg atacgtatat acacttttgt   420
aaaatattat tcggtgtcta taacggaaca aacgctacta tatattatca tagacctcta   480
acgggatata tgaatatgat ttcagatact atatttgttc ctgtagataa taactaaggc   540
gcgcctttca ttttgttttt ttctatgcta taaatggtga gcaagggcga ggagctgttc   600
accggggtgg tgcccatcct ggtcgagctg gacggcgacg taaacggcca caagttcagc   660
gtgtccggcg agggcgaggg cgatgccacc tacggcaagc tgaccctgaa gttcatctgc   720
accaccggca agctgcccgt gccctggccc accctcgtga ccaccctgac ctacggcgtg   780
cagtgcttca gccgctaccc cgaccacatg aagcagcacg acttcttcaa gtccgccatg   840
cccgaaggct acgtccagga gcgcaccatc ttcttcaagg acgacggcaa ctacaagacc   900
cgcgccgagg tgaagttcga gggcgacacc ctggtgaacc gcatcgagct gaagggcatc   960
gacttcaagg aggacggcaa catcctgggg cacaagctgg agtacaactt caacagccac  1020
aacgtctata tcatggccga caagcagaag aacggcatca aggtgaactt caagatccgt  1080
cacaacatcg aggacggcag cgtgcagctc gccgaccact accagcagaa cacccccatc  1140
ggcgacggcc ccgtgctgct gcccgacaac cactacctga gcacccagtc cgccctgagc  1200
aaagacccca acgagaagcg cgatcacatg gtcctgctgg agttcgtgac cgccgccggg  1260
atcactctcg gcatgcacga gctgtacaag taagagctcg aggacgggga aattaactag  1320
tattgtacaa gaagccattt tatctctaaa tttacgaatt aagattttaa attttaaaca  1380
taaagatgat gatacgtata tacacttttg taaaatatta ttcggtgtct ataacggaac  1440
aaacgctact atatattatc atagacctct aacgggatat atgaatatga tttcagatac  1500
tatatttgtt cctgtagata ataactaact cgaggccgct ggtacccaac ctaaaaattg  1560
aaaataaata caaaggttct tgagggttgt gttaaattga aagcgagaaa taatcataaa  1620
taagcccggg atgggaggac tatctctact acaactacca agataagt ttagaaaatc    1680
ttctttcttt gtttgggtta taattctatt tcaaaggcg ttctctatgc cattgggagt   1740
agtaacaaat tctacactag aagtaacaga aattgatcaa ctagtatgta aagatcatct  1800
agcgtctaca gatcaattga aatctgttgg attgaatcta gaaggatctg tgtatctac   1860
agatattcca tctgcgacaa agagatgggg ttttagaagt ggtgtaccac caaaagtagt  1920
atcttatgaa gcgggagaat gggcggaaaa ttgttataat ctagaaatta gaaaccaga   1980
tggatctgaa tgtttgccac caccaccaga tggtgttgaa ggatttccaa gatgtagata  2040
tgttcataaa gcgcaaggaa caggaccatg tcctggagat tatgcgtttc ataagatgga  2100
tgcattcttt ctatatgata gattggcgtc tactgtaata tatagaggtg taaattttgc  2160
ggaaggtgta attgcttttc taattctagc gaaacctaaa gaaacatttc tacaatctcc  2220
accaattaga gaagcggtta attatacaga aaatacttca tcttattatg cgacatctta  2280
tctagaatat gaaattgaaa attttggagc gcaacattct acaacttgt tcaaaattga   2340
taataatact tttgttagac tagatagacc acatacacca caattttgt ttcaattgaa   2400
tgatacaatt catctacatc aacaactatc taatacaact ggaagattga tttgacact   2460
agatgcgaat attaatgcgg atattggaga atgggctttc tgggaaaata gaagaatctg  2520
atctgaacaa ctaagaggag aagaattgtc ttttgaagcg ctatctctaa atgaaactga  2580
agatgatgat gcggcgtcta gtagaattac aaaaggaaga atttctgata gagcgacaag  2640
acaatattct gatctagtac caaagaatcc acctggaatg gttccattgc atattccaga  2700
aggagaaaca acactaccat ctcaaaattc tactgaagga agaagagtat ctgtaaatac  2760
tcaagaaaca attacagaaa cagcggcgac aattattgga acaaatggaa atcatatgca  2820
aatttctact attggaatta gaccatcttc ttctcaaatt ccatcttcta gtcaacaac   2880
agcgccatct ccagaagcgc aaacaccaac aacacataca agtggaccat ctgtaatggc  2940
gacagaagaa cctacaacac caccaggatc ttctccaggt ccaactacag aagcgccaac  3000
tctaactaca ccagaaaata ttacaacagc tgtaaagaca gtactaccac aagaatctac  3060
ttctaatgga ctaattacat ctacagtaac tggaattcta ggatctctag gactaagaaa  3120
gagatctaga agacaaacaa tacaaaagc gactgtaaaa tgtacattca  3180
ttggacagcg caagaacaac ataatgcggc gggaattgct tggattccat attttggacc  3240
aggtgctgaa ggaatatata ctgaaggtct aatgcataat caaaatgcgc tagtatgtgg  3300
actaagacaa ctagcgaatg aaacaactca agcgctacaa ctatttctaa gagcgactac  3360
agaactaaga acatatacaa ttctaaatag aaaagcgtat gatttcttgt tgagaagatg  3420
gggaggaaca tgtagaatat tgggaccaga ttgttgtatt gaaccacatg attggacaaa  3480
```

```
gaatattact gacaaaatta atcaaattat tcatgacttt attgataatc cactaccaaa 3540
tcaagataat gatgataatt ggtgacagg atggagacaa tggattccag cgggaatagg 3600
aattactgga attattattg cgattatagc gctactatgt gtatgtaaac tactatgtta 3660
ataagtcgac ctgcagtcaa actctaatga ccacatcttt ttttagagat gaaaaatttt 3720
ccacatctcc ttttgtagac acgactaaac attttgcaga aaaaagttta ttagtgttta 3780
gataatcgta tacttcatca gtgtagatag taaatgtgaa cagataaaag gtattcttgc 3840
tcaatagatt ggtaaattcc atagaatata ttaatccttt cttcttgaga tcccacatca 3900
tttcaaccag agacgtttta tccaatgatt tacctcgtac tataccacat acaaaactag 3960
attttgcagt gacgtcgtat ctggtattcc taccaaacaa aatttactt ttagttcttt 4020
tagaaaattc taaggtagaa tctctatttg ccaatatgtc atctatgaa ttaccactag 4080
caaaaaatga tagaaatata tattgataca tcgcagctgg ttttgatcta ctatacttta 4140
aaaacgaatc agattccata attgcctgta tatcatcagc tgaaaaacta tgttttacac 4200
gtattccttc ggcatttctt tttaatgata tcttgttt agacaatgat aaagttatca 4260
tgtccatgag agacgcgtct ccgtatcgta taaatatttc attagatgtt agacgcttca 4320
ttaggggtat acttctataa ggtttcttaa tcagtccatc attggttgcg tcaagaacaa 4380
gcttgtctcc ctatagtgag tcgtattaga gcttggcgta atcatggtca tagctgtttc 4440
ctgtgtgaaa ttgttatccg ctcacaattc cacacaacat acgagccgga agcataaagt 4500
gtaaagcctg gggtgcctaa tgagtgagct aactcacatt aattgcgttg cgctcactgc 4560
ccgctttcga gtcgggaaac ctgtcgtgcc agctgcatta atgaatcggc caacgcgcgg 4620
ggagaggcgg tttgcgtatt gggcgctctt ccgcttcctc gctcactgac tcgctgcgct 4680
cggtcgttcg gctgcggcga gcggtatcag ctcactcaaa ggcggtaata cggttatcca 4740
cagaatcagg ggataacgca ggaaagaaca tgtgagcaaa aggccagcaa aaggccagga 4800
accgtaaaaa ggccgcgttg ctggcgtttt tcgataggct ccgccccct gacgagcatc 4860
acaaaaatcg acgctcaagt cagaggtggc gaaacccgac aggactataa agataccagg 4920
cgtttccccc tggaagctcc ctcgtgcgct ctcctgttcc gaccctgccg cttaccggat 4980
acctgtccgc ctttctccct tcgggaagcg tggcgctttc tcatagctca cgctgtaggt 5040
atctcagttc ggtgtaggtc gttcgctcca agctgggctg tgtgcacgaa ccccccgttc 5100
agcccgaccg ctgcgcctta tccggtaact atcgtcttga gtccaacccg gtaagacacg 5160
acttatcgcc actggcagca gccactggta acaggattag cagagcgagg tatgtaggcg 5220
gtgctacaga gttcttgaag tggtggccta actacggcta cactagaagg acagtatttg 5280
gtatctgcgc tctgctgaag ccagttacct tcggaaaaag agttggtagc tcttgatccg 5340
gcaaacaaac caccgctggt agcggtggtt tttttgtttg caagcagcag attacgcgca 5400
gaaaaaaagg atctcaagaa gatcctttga tcttttctac ggggtctgac gctcagtgga 5460
acgaaaactc acgttaaggg attttggtca tgagattatc aaaaaggatc ttcacctaga 5520
tccttttaaa ttaaaaatga agttttaaat caatctaaag tatatatgag taaacttggt 5580
ctgacagtta ccaatgctta atcagtgagg cacctatctc agcgatctgt ctatttcgtt 5640
catccatagt tgcctgactc cccgtcgtgt agataactac gatacgggag ggcttaccat 5700
ctggccccag tgctgcaatg ataccgcgag acccacgctc accggctcca gatttatcag 5760
caataaacca gccagccgga agggccgagc gcagaagtgg tcctgcaact ttatccgcct 5820
ccatccagtc tattaattgt tgccgggaag ctagagtaag tagttcgcca gttaatagtt 5880
tgcgcaacgt tgttggcatt gctacaggca tcgtggtgtc acgctcgtcg tttggtatgg 5940
cttcattcag ctccggttcc caacgatcaa ggcgagttac atgatccccc atgttgtgca 6000
aaaaagcggt tagctccttc ggtcctccga tcgttgtcag aagtaagttg gccgcagtgt 6060
tatcactcat ggttatggca gcactgcata attctcttac tgtcatgcca tccgtaagat 6120
gcttttctgt gactggtgag tactcaacca agtcattctg agaatagtgt atgcggcgac 6180
cgagttgctc ttgcccggcg tcaatacggg ataataccgc gccacatagc agaactttaa 6240
aagtgctcat cattggaaaa cgttcttcgg ggcgaaaact ctcaaggatc ttaccgctgt 6300
tgagatccag ttcgatgtaa cccactcgtg cacccaactg atcttcagca tcttttactt 6360
tcaccagcgt ttctgggtga gcaaaaacag gaaggcaaaa tgccgcaaaa aagggaataa 6420
gggcgacacg gaaatgttga atactcatac tcttcctttt tcaatattat tgaagcattt 6480
atcagggtta ttgtctcatg agcggataca tatttgaatg tatttagaaa aataaacaaa 6540
taggggttcc gcgcacattt ccccgaaaag tgccacctga cgtctaagaa accattatta 6600
tcatgacatt aacctataaa aataggcgta tcacgaggcc ctttcgtctc gcgcgtttcg 6660
gtgatgacgg tgaaaacctc tgacacatgc agctcccgga gacggtcaca gcttgtctgt 6720
aagcggatgc cgggagcaga caagcccgtc agggcgcgtc agcgggtgtt ggcgggtgtc 6780
ggggctggct taactatgcg gcatcagagc agattgtact gagagtgcac catatgcggt 6840
gtgaaatacc gcacagatgc gtaaggagaa aataccgcat caggcgccat tcgccattca 6900
ggctgcgcaa ctgttgggaa gggcgatcgg tgcgggcctc ttcgctatta cgccagctgg 6960
cgaaaggggg atgtgctgca aggcgattaa gttgggtaac gccagggttt cccagtcac 7020
gacgttgtaa aacgacggcc agtgaattgg atttaggtga cactata 7067
```

SEQ ID NO: 14        moltype = DNA   length = 5807
FEATURE             Location/Qualifiers
source              1..5807
                     mol_type = other DNA
                     organism = Marburg virus
SEQUENCE: 14

```
gaattcggag tatacgaacc gggaaagaga agatggttaa aaataaagcg agactatttg 60
aacgagggtt ccatggcaga ttctgccgat ttagtagtac taggtgctta ctatggtaaa 120
ggagcaaagg gtggtatcat ggcagtcttt ctaatgggtt gttacgacga tgaatccggt 180
aaatggaaga cggttaccaa gtgttcagga cacgatgata tacgttaag ggagttgcaa 240
gaccaattaa agatgattaa aattaacaag gatcccaaaa aaattccaga gtggttagta 300
gttaataaaa tctatattcc cgattttgta gtagaggatc caaacaatc tcagatatgg 360
gaaatttcag gagcagagtt tacatcttcc aagtcccata ccgcaaatgg aatatccatt 420
agatttccta gatttactag gataagagag gataaaacgt ggaaagaatc tactcatcta 480
aacgatttag taaactgac taaatcttaa ttttatggc gcgcctttca ttttgttttt 540
ttctatgcta taaatggtga gcaagggcga ggagctgttc accggggtgg tgcccatcct 600
ggtcgagctg gacggcgacg taaacggcca caagttcagc gtgtccggcg agggcgaggg 660
cgatgccacc tacggcaagc tgaccctgaa gttcatctgc accaccggca agctgcccgt 720
```

```
gccctggccc accctcgtga ccaccctgac ctacggcgtg cagtgcttca gccgctaccc  780
cgaccacatg aagcagcacg acttcttcaa gtccgccatg cccgaaggct acgtccagga  840
gcgcaccatc ttcttcaagg acgacggcaa ctacaagacc cgcgccgagg tgaagttcga  900
gggcgacacc ctggtgaacc gcatcgagct gaagggcatc gacttcaagg aggacggcaa  960
catcctgggg cacaagctgg agtacaacta caacagccac aacgtctata tcatggccga 1020
caagcagaag aacggcatca aggtgaactt caagatccgc cacaacatcg aggacggcag 1080
cgtgcagctc gccgaccact accagcagaa caccccatc ggcgacggcc ccgtgctgct 1140
gcccgacaac cactacctga gcacccagtc cgccctgagc aaagacccca cgagaagcg 1200
cgatcacatg gtcctgctgg agttcgtgac cgccgccggg atcactctcg gcatgcacga 1260
gctgtacaag taagagctcc ccgattttgt agtagaggat ccaaaacaat ctcagatatg 1320
ggaaatttca ggagcagagt ttacatcttc caagtccat accgcaaatg gaatatccat 1380
tagatttcct agatttacta ggataagaga ggataaaacg tggaaagaat ctactcatct 1440
aaacgattta gtaaacttga ctaaatctta atttttatct cgaggccgct ggtacccaac 1500
ctaaaaattg aaaataaata caaaggttct tgagggttgt gttaaattga aagcgagaaa 1560
taatcataaa taagcccggg atggcgtcta gttctaatta taatacttat atgcaatatc 1620
taaatccacc accatatgcg gatcatggtg ctaatcaact aattccagcg gatcaactat 1680
ctaatcaaca tggaattaca ccaaattatg ttggagatct aaatctagat gatcagttta 1740
aaggaaatgt ttgtcatgcg tttacactag aagcgattat tgatatttct gcgtataatg 1800
aaagaacagt aaaaggtgta ccagcttggc taccactagg aattatgtct aattttgaat 1860
atccactagc gcatacagta gcggcgctat tgacaggatc ttatacaatt acacagttta 1920
cacataatgg acaaaagttt gttagagtaa atagactagg aactgaaata ccagcgcatc 1980
cactaagaat gctaagagaa ggaaatcaag cttttattca aaatatggtt attccaagaa 2040
atttctctac aaatcagttt acttataatc taactaatct agtactatct gtacaaaagc 2100
taccagatga tgcttggaga ccatctaaag ataaactaat tggaaataca atgcatccag 2160
cgatttctat tcatccaaat ctaccaccaa tagtactacc aactgtaaag aaacaagcgt 2220
atagacaaca taagaatcca aataatgaac cactattggc gatttctgga attctacatc 2280
aactaagagt agaaaaggta ccagaaaaga catctttgtt tagaatttct ctaccagcgg 2340
atatgttttc tgtaaaagaa ggaatgatga agaaaagagg agaatcttct ccagtagtat 2400
attttcaagc gccagaaaat tttccattga atggtttaa taatagacaa gtagtactag 2460
cgtatgcgaa tccaacacta tctgcgtat aataagtcga cctgcagcta atgtattagt 2520
taaatattaa aacttaccac gtaaaactta aaatttaaaa tgatatttca ttgacagata 2580
gatcacacat tatgaacttt caaggacttg tgttaactga caattgcaaa atcaatgggg 2640
tcgttggacc attaatagga aaaggtggat ttggtagtat ttatactact aatgacaata 2700
attatgtagt aaaaatagag cccaaagcta acggatcatt atttaccgaa caggcatttt 2760
atactagagt acttaaacca tccgttatcg aagaatggaa aaaatctcac aatataaagc 2820
acgtaggtct tatcacgtgc aaggcatttg gtctatacaa atccattaat gtggaatatc 2880
gattcttggt aattaataga ttaggtgcag atctagatgc ggtgatcaga gccaataata 2940
atagattacc aaaaggtcg gtgatgttga tcggaatcga aatcttaaat accatacaat 3000
ttatgcacga gcaaggatat tctcacggag atatttaagc gagtaatata gtcttggatc 3060
aaatagataa gaataaatta tatctagtgg attacggatt ggtttctaaa ttcatgtcaa 3120
gcttgtctcc ctatagtgag tcgtattaga gcttggcgta atcatggtca tagctgtttc 3180
ctgtgtgaaa ttgttatccg ctcacaattc cacacaacat acgagccgga agcataaagt 3240
gtaaagcctg gggtgcctaa tgagtgagct aactcacatt aattgcgttg cgctcactgc 3300
ccgctttcga gtcgggaaac ctgtcgtgcc agctgcatta atgaatcggc caacgcgcgg 3360
ggagaggcgg tttgcgtatt gggcgctctt ccgcttcctc gctcactgac tcgctgcgct 3420
cggtcgttcg gctgcggcga gcggtatcag ctcactcaaa ggcggtaata cggttatcca 3480
cagaatcagg ggataacgca ggaaagaaca tgtgagcaaa aggccagcaa aaggccagga 3540
accgtaaaaa ggccgcgttg ctggcgtttt tcgataggct ccgcccccct gacgagcatc 3600
acaaaaatcg acgctcaagt cagaggtggc gaaacccgac aggactataa agataccagg 3660
cgtttccccc tggaagctcc ctcgtgcgct ctcctgttcc gaccctgccg cttaccggat 3720
acctgtccgc ctttctccct tcgggaagcg tggcgctttc tcatagctca cgctgtaggt 3780
atctcagttc ggtgtaggtc gttcgctcca agctgggctg tgtgcacgaa ccccccgttc 3840
agcccgaccg ctgcgcctta tccggtaact atcgtcttga gtccaacccg gtaagacacg 3900
acttatcgcc actggcagca gccactggta acaggattag cagagcgagg tatgtaggcg 3960
gtgctacaga gttcttgaag tggtggccta actacggcta cactagaagg acagtatttg 4020
gtatctgcgc tctgctgaag ccagttacct tcggaaaaag agttggtagc tcttgatccg 4080
gcaaacaaac caccgctggt agcggtggtt tttttgtttg caagcagcag attacgcgca 4140
gaaaaaaagg atctcaagaa gatcctttga tcttttctac ggggtctgac gctcagtgga 4200
acgaaaactc acgttaaggg attttggtca tgagattatc aaaaaggatc ttcacctaga 4260
tccttttaaa ttaaaaatga agttttaaat caatctaaag tatatatgag taaacttggt 4320
ctgacagtta ccaatgctta atcagtgagg cacctatctc agcgatctgt ctatttcgtt 4380
catccatagt tgcctgactc cccgtcgtgt agataactac gatacgggag gcttaccatc 4440
tggccccag tgctgcaatg ataccgcgag acccacgctc accggctcca gatttatcag 4500
caataaacca gccagccgga agggccgagc cagaagtgg tcctgcaact ttatccgcct 4560
ccatccagtc tattaattgt tgccgggaag ctagagtaag tagttcgcca gttaatagtt 4620
tgcgcaacgt tgttggcatt gctacaggca tcgtggtgtc acgctcgtcg tttggtatgg 4680
cttcattcag ctccggttcc caacgatcaa ggcgagttac atgatccccc atgttgtgca 4740
aaaaagcggt tagctccttc ggtcctccga tcgttgtcag aagtaagttg gccgcagtgt 4800
tatcactcat ggttatggca gcactgcata attctcttac tgtcatgcca tccgtaagat 4860
gcttttctgt gactggtgag tactcaacca agtcattctg agaatagtgt atgcggcgac 4920
cgagttgctc ttgcccggcg tcaatacggg ataaatccgc gccacatagc agaactttaa 4980
aagtgctcat cattggaaaa cgttcttcgg ggcgaaaact ctcaaggatc ttaccgctgt 5040
tgagatccag ttcgatgtaa cccactcgtg cacccaactg atcttcagca tcttttactt 5100
tcaccagcgt ttctgggtga gcaaaaacag gaaggcaaaa tgccgcaaaa aagggaataa 5160
gggcgacacg gaaatgttga atactctac tcttcctttt tcaatattat tgaagcatt 5220
atcagggtta ttgtctcatg agcggataca tatttgaatg tatttagaaa aataaacaaa 5280
tagggggttcc gcgcacattt ccccgaaaag tgccacctga cgtctaagaa accattatta 5340
tcatgacatt aacctataaa aataggcgta tcacgaggcc ctttcgtctc gcgcgtttcg 5400
gtgatgacgg tgaaaacctc tgacacatgc agctcccgga cggtcaca gcttgtctgt 5460
```

-continued

```
aagcggatgc cgggagcaga caagcccgtc agggcgcgtc agcgggtgtt ggcgggtgtc   5520
ggggctggct taactatgcg gcatcagagc agattgtact gagagtgcac catatgcggt   5580
gtgaaatacc gcacagatgc gtaaggagaa aataccgcat caggcgccat tcgccattca   5640
ggctgcgcaa ctgttgggaa gggcgatcgg tgcgggcctc ttcgctatta cgccagctgg   5700
cgaaagggg  atgtgctgca aggcgattaa gttgggtaac gccagggttt tcccagtcac   5760
gacgttgtaa aacgacggcc agtgaattgg atttaggtga cactata              5807
```

```
SEQ ID NO: 15           moltype = DNA  length = 7082
FEATURE                 Location/Qualifiers
source                  1..7082
                        mol_type = other DNA
                        organism = Marburg virus
SEQUENCE: 15
gaattccctg ggacatacgt atatttctat gatctgtctt atatgaagtc tatacagcga   60
atagattcag aatttctaca taattatata ttgtacgcta ataagtttaa tctaacactc   120
cccgaagatt tgtttataat ccctacaaat ttggatattc tatggcgtac aaaggaatat   180
atagactcgt tcgatattag tacagaaaca tggaataaat tattatccaa ttattatatg   240
aagatgatag agtatgctaa acttttatgta ctaagtccta ttctcgctga ggagttggat   300
aattttgaga ggacgggaga attaactagt attgtacaag aagccatttt atctctaaat   360
ttacgaatta agattttaaa ttttaaacat aaagatgatg atacgtatat acacttttgt   420
aaaatattat tcggtgtcta taacggaaca aacgctacta tatattatca tagacctcta   480
acgggatata tgaatatgat ttcagatact atatttgttc ctgtagataa taactaaggc   540
gcgcctttca ttttgttttt ttctatgcta taaatggtga gcaagggcga ggagctgttc   600
accggggtgg tgcccatcct ggtcgagctg gacggcgacg taaacggcca caagttcagc   660
gtgtccggcg agggcgaggg cgatgccacc tacggcaagc tgaccctgaa gttcatctgc   720
accaccggca agctgcccgt gccctggccc accctcgtga ccaccctgta ctacggcgtg   780
cagtgcttca gccgctaccc cgaccacatg aagcagcacg acttcttcaa gtccgccatg   840
cccgaaggct acgtccagga gcgcaccatc ttcttcaagg acgacggcaa ctacaagacc   900
cgcgccgagg tgaagttcga gggcgacacc ctggtgaacc gcatcgagct gaagggcatc   960
gacttcaagg aggacggcaa catcctgggg cacaagctgg agtacaacta caacagccac   1020
aacgtctata tcatggccga caagcagaag aacggcatca aggtgaactt caagatccgc   1080
cacaacatcg aggacggcag cgtgcagctc gccgaccact accagcagaa cacccccatc   1140
ggcgacggcc ccgtgctgct gcccgacaac cactacctga gcacccagtc cgccctgagc   1200
aaagaccccca acgagaagcg cgatcacatg gtcctgctgg agttcgtgac cgccgccggg   1260
atcactctcg gcatgacga  gctgtacaag taagagctcg aggacgggag aattaactag   1320
tattgtacaa gaagccattt tatctctaaa tttacgaatt aagattttaa attttaaaca   1380
taaagatgat gatacgtata tacactttg  taaaatatta ttcggtgtct ataacggaac   1440
aaacgctact atatattatc atagacctct aacgggatat atgaatatga tttcagatat   1500
tatatttgtt cctgtagata ataactaact cgaggccgct ggtaccccaac ctaaaaattg   1560
aaaataaata caaaggttct tgaggggttgt gttaaattga aagcgagaaa taatcataaa   1620
taagcccggg atgtggacaa catgtttctt catttctcta attctaattc aaggaattaa   1680
aacactacca attctagaaa ttgcgtctaa tgatcaacca caaatgtag  attctgtatg   1740
ttctggaaca ctacaaaaga ctgaagatgt acatttgatg ggttttacac tatctggaca   1800
aaaggtagcg gattctccac tagaagcgtc taaaagatgg gcgtttagaa caggtgtacc   1860
accaaagaat gttgaatata cagaaggaga agaagcgaaa acttgttata atatttctgt   1920
aacagatcca tctggaaaat ctctactact agatccacca actaatgtta gagattatcc   1980
aaaatgtaaa acaattcatc atattcaagg acaaaatcc  catgcgcaag gaattgcgct   2040
acatctatgg ggagcattct ttctatatga tagaatagcg tctacaacaa tgtatagagg   2100
aaaagttttc actgaaggaa atattgcggc tatgatagta aataagacag ttcacaaaat   2160
gatatttctc tagacaaggac aaggatatag acatatgaat ctaacatcta caaatataata   2220
ttggacatct tctaatggaa cacaaacaaa tgatacagga tgttttgaca cattgcagaa   2280
atataatagt acaaagaatc aaacatgtgc gccatctaaa actccaccac acctccaac    2340
agcgcatcca gaaattaaac ctacatctac accaacagat gcgacaagat tgaatacaac   2400
aaatccaaat tctgatgatg aagatctaac aacatctgga tctggaagtg agaacaaga    2460
accatataca acaagtgatg cggttacaaa gcaaggacta tcttctacaa tgccaccaac   2520
actatctcca caacctggaa ctccacaaca aggtgaaat  aatacaaatc attctcaaga   2580
tgcggcgaca gaactagata atactaatac aactgcgcaa ccaccaatgc catctcataa   2640
tactacaact atttctacta taatactttc taaacataat ctatctacat tgctctgaacc   2700
acctcaaaat actactaatc taattactca atctatggcg actgaaaatg aaaagacttc   2760
tgcgcctcca aagacaactc taccaccaac tgaatctcca acaacagaga agagtacaaa   2820
taatacaaaa tctccaacta caatggaacc taatacaact aatggacact ttacatctcc   2880
atcttctact cctaattcta caacacaaca tttgatatac tttagaagaa agagatctat   2940
tttgtggaga gaaggagata tgtttccatt tctagatgga ttgattaatg cgccaattga   3000
tttgatcca  gtaccaaata caaagacaat tttcgatgaa tcttcttctt ctggtgcttc   3060
tgcggaagaa gatcaacatg cgtctagtaa tattagtcta acattgtctt atctacctca   3120
tacttctgaa aatactgcgt atagtggaga aaatgagaat gattgtgatg cggaactaag   3180
aatttggagt gtacaagaag atgatctagc ggcgggattg tcttggatc  ctttcttcgg   3240
acctggaatt gaaggactat atacagcggg attgattaag aatcagaata atctagtatg   3300
tagactaaga agattggcga atcaaacagc gaaatctcta gaactactac taagagtaac   3360
aactgaagaa agaacattct ctttgattaa tagacatgcg attgattttc tattgacaag   3420
atgggggagga acatgtaaag tactaggacc agattgttgt attggaatag aagatctatc   3480
tagaaatatt tcagaacaaa ttgatcaaat taagaaagat gaacaaaagg aaggaactgg   3540
atgggaacta ggtggaaaat ggtggacatc tgattgggga gtactaacaa atctaggaat   3600
tctactattg ctatctattg cggttactaat tgcgtttgct tgtatatgta gaattttcac   3660
aaagtatatt ggataatag  tcgacctgca gtcaaactct aatgaccaca tcttttttta   3720
gagatgaaaa attttccaca tctccttttg tagacacgac taaacatttt gcagaaaaaa   3780
gtttattagt gtttagataa tcgtatactt catcagtgta gatagtaaat gtgaacagat   3840
aaaggtatt  cttgctcaat agattggtaa attccataga atatattaat cctttcttct   3900
tgagatccca catcatttca accagagacg ttttatccaa tgatttacct cgtactatac   3960
```

```
cacatacaaa actagatttt gcagtgacgt cgtatctggt attcctacca acaaaatttt    4020
tactttagt  tcttttagaa aattctaagg tagaatctct atttgccaat atgtcatcta    4080
tggaattacc actagcaaaa aatgatagaa atatatattg atacatcgca gctggttttg    4140
atctactata ctttaaaaac gaatcagatt ccataattgc ctgtatatca tcagctgaaa    4200
aactatgttt tacacgtatt ccttcggcat ttcttttaa tgatatatct tgtttagaca     4260
atgataaagt tatcatgtcc atgagagacg cgtctccgta tcgtataaat atttcattag    4320
atgttagacg cttcattagg ggtatacttc tataagtttt cttaatcagt ccatcattgg    4380
ttgcgtcaag aacaagcttg tctccctata gtgagtcgta ttagagcttg gcgtaatcat    4440
ggtcatagct gtttcctgtg tgaaattgtt atccgctcac aattccacac aacatacgga    4500
ccggaagcat aaagtgtaaa gcctggggtg cctaatgagt gagctaactc acattaattg    4560
cgttgcgctc actgcccgct ttcgagtcgg gaaacctgtc gtgccagctg cattaatgaa    4620
tcggccaacg cgcggggaga gcggtttgc  gtattgggcg ctcttccgct tcctcgctca    4680
ctgactcgct gcgctcggtc gttcggctgc ggcgagcgg  atcagctcac tcaaaggcgg    4740
taatacggtt atccacagaa tcaggggata acgcaggaaa gaacatgtga gcaaaaggcc    4800
agcaaaaggc caggaaccgt aaaaaggccg cgttgctggc gtttttcgat aggctccgcc    4860
cccctgacga gcatcacaaa aatcgacgct caagtcagag gtggcgaaac ccgacaggac    4920
tataaagata ccaggcgttt cccctggaa  gctcccgcgt gcgctctcct gttccgaccc    4980
tgccgcttac cggatacctg tccgcctttc tcccttcggg aagcgtggcg ctttctcata    5040
gctcacgctg taggtatctc agttcggtgt aggtcgttcg ctccaagctg ggctgtgtgc    5100
acgaaccccc cgttcagccc gaccgctgcg ccttatccgg taactatcgt cttgagtcca    5160
acccggtaag acacgactta tcgccactgg cagcagccac tggtaacagg attagcagag    5220
cgaggtatgt aggcggtgct acagagttct tgaagtggtg gcctaactac ggctacacta    5280
gaaggacagt atttggtatc tgcgctctgc tgaagccagt taccttcgga aaaagagttg    5340
gtagctcttg atccggcaaa caaaccaccg ctggtagcgg tggtttttt  gtttgcaagc    5400
agcagattac gcgcagaaaa aaaggatctc aagaagatcc tttgatcttt tctacggggt    5460
ctgacgctca gtggaacgaa aactcacgtt aagggatttt ggtcatgaga ttatcaaaaa    5520
ggatcttcac ctagatcctt ttaaattaaa aatgaagttt taaatcaatc taaagtatat    5580
atgagtaaac ttggtctgac agttaccaat gcttaatcag tgaggcacct atctcagcga    5640
tctgtctatt tcgttcatcc atagttgcct gactccccgt cgtgtagata actacgatac    5700
gggagggctt accatctggc cccagtgctg caatgatacc gcgagaccca cgctcaccgg    5760
ctccagattt atcagcaata accagccagc ccggaagggc cgagcgcaga gtggtcctgc    5820
caactttatc cgcctccatc cagtctatta attgttgccg ggaagctaga gtaagtagtt    5880
cgccagttaa tagtttgcgc aacgttgttg cattgctac  aggcatcgtg gtgtcacgct    5940
cgtcgtttgg tatggcttca ttcagctccg gttcccaacg atcaaggcga gttacatgat    6000
cccccatgtt gtgcaaaaaa gcggttagct ccttcggtcc tccgatcgtt gtcagaagta    6060
agttggccgc agtgttatca ctcatggtta tggcagcact gcataattct cttactgtca    6120
tgccatccgt aagatgcttt tctgtgactg gtgagtactc aaccaagtca ttctgagaat    6180
agtgtatgcg gcgaccgagt tgctcttgcc cggcgtcaat acgggataat accgcgccac    6240
atagcagaac tttaaaagtg ctcatcattg gaaaacgttc ttcggggcga aaactctcaa    6300
ggatcttacc gctgttgaga tccagttcga tgtaacccac tcgtgcaccc aactgatctt    6360
cagcatcttt tactttcacc agcgtttctg ggtgagcaaa aacaggaagg caaaatgccg    6420
caaaaaaggg aataagggcg acacggaaat gttgaatact catactcttc ctttttcaat    6480
attattgaag catttatcag ggttattgtc tcatgagcgg atacatattt gaatgtattt    6540
agaaaaataa acaaataggg gttccgcgca catttcccg  aaaagtgcca cctgacgtct    6600
aagaaaccat tattatcatg acattaacct ataaaaatag gcgtatcacg aggccctttc    6660
gtctcgcgcg tttcggtgat gacggtgaaa acctctgaca catgcagctc ccggagacgg    6720
tcacagcttg tctgtaagcg gatgccggga gcagacaagc ccgtcagggc gcgtcagcgg    6780
gtgttggcgg gtgtcgggc  tggcttaact atgcggcatc agagcagatt gtactgagag    6840
tgcaccatat gcggtgtgaa ataccgcaca gatgcgtaag gagaaaatac cgcatcaggc    6900
gccattcgcc attcaggctg cgcaactgtt gggaagggcg atcggtgcgg gcctcttcgc    6960
tattacgcca gctggcgaaa ggggatgtg  ctgcaaggcg attaagttgg gtaacgccag    7020
ggttttccca gtcacgacgt tgtaaaacga cggccagtga attggattta ggtgacacta    7080
ta                                                                   7082

SEQ ID NO: 16          moltype = DNA  length = 1479
FEATURE                Location/Qualifiers
source                 1..1479
                       mol_type = other DNA
                       organism = Lassa virus
SEQUENCE: 16
atgggacaaa tagtaacatt cttccaagaa gtaccacatg taattgaaga agtaatgaat      60
attgtactaa ttgcgctatc tgtactagcg gtattgaaag gattgtataa tttcgcgaca     120
tgtggactag taggactagt tacatttcta ctactatgtg gaagatcttg tacaacttct     180
ttgtataaag gagtatatga actacaaaca ctagaattga atgtgaaac  tcaaaattga     240
acaatgcctc tatcatgtac aaagaataat tctcatcatt atattatggt tggaaatgaa     300
acaggactag aactaacact aacaaatact tctattatta atcataaatt ctgtaatcta     360
tctgatgcgc ataagaagaa tctatatgat catgcgctaa tgtctattat ttctacattt     420
catctatcta ttccaaactt taatcaatat gaagctatgt cttgtgactt taatggtgga     480
aagatttctg tacaatataa tctaagtcat tcttatgcgg tagatgcggc gaatcattgt     540
ggaacagtag cgaatggtgt actacaaact ttcatgagaa tggcgtgggg aggatcttat     600
attgcgctag attctggaag aggaaattgg gattgtatta tgcatctta  tcaatatcta     660
attattcaga atacaacatg ggaagatcat tgtcaattct ctagaccatc tccaatagga     720
tatctaggac tactatctca agaacaaga  gatatatata ttagtagaag attgctagga     780
acttcacat  ggacactatc tgattctgaa ggaaaggata cacctggagg atattgtcta     840
acaagatgga tgctaattga agcggaattg aaatgttttg gaaatactgc ggtagcgaaa     900
tgtaatgaaa agcatgatga agaatttgtg gatatgctaa gactatttga ctttaataaa     960
caagcgattc aaagattgaa agcggaagcg caaatgagta ttcaattgat aaataaagcg    1020
gttaatgctt tgattaatga tcaactaatt atgaagaatc atctaagaga tattatggga    1080
attccatatt gtaattatag taaatattgg tatctaaatc atacaacaac tggaagaaca    1140
```

-continued

```
tctctaccaa aatgttggct agtatctaat ggatcttatc taaatgaaac acatttctct 1200
gatgatattg aacaacaagc ggataatatg attacagaaa tgctacaaaa ggaatatatg 1260
gaaagacaag gaaagacacc actaggattg gtagatctat ttgttttctc tacatctttc 1320
tatctaatta gtatatttct acatctagta aagattccaa cacatagaca tatagtagga 1380
aaatcttgtc caaaaccaca tagattgaat catatgggaa tatgttcttg tggattgtat 1440
aaacaaccag gtgtaccagt taaatggaaa agataataa                         1479

SEQ ID NO: 17          moltype = DNA  length = 303
FEATURE                Location/Qualifiers
source                 1..303
                       mol_type = other DNA
                       organism = Lassa virus
SEQUENCE: 17
atgggaaata aacaagcgaa agcgccagaa tctaaagatt ctccaagagc gagtctaatt  60
ccagatgcga cacatctagg accacaattt tgtaaatctt gttggtttga aaataaagga  120
ctagtagaat gtaataatca ttatctatgt ctaaattgtc taacactact actatctgta  180
tctaatagat gtccaatatg caaaatgcca ctaccaacaa aactaagacc atctgctgct  240
ccaacagcgc caccaacagg tgctgctgat tctattagac caccaccata ttctccataa  300
taa                                                                303
```

REPLICATION-DEFICIENT MODIFIED VACCINIA ANKARA (MVA) EXPRESSING MARBURG VIRUS GLYCOPROTEIN (GP) AND MATRIX PROTEIN (VP40)

CROSS REFERENCE TO RELATED APPLICATIONS

This application is a continuation of U.S. patent application Ser. No. 17/584,231, filed Jan. 25, 2022, which is a continuation of U.S. patent application Ser. No. 15/543,139, filed May 17, 2018, which is a national stage application under 35 U.S.C. § 371 of International Application No. PCT/US2016/013021, filed Jan. 12, 2016, which claims the benefit of and priority to U.S. provisional patent application U.S. 62/102,425 filed Jan. 12, 2015, U.S. provisional patent application U.S. 62/213,819 filed Sep. 3, 2015, and U.S. provisional patent application U.S. 62/215,536 filed Sep. 8, 2015. The entirety of each of these applications is hereby incorporated by reference herein for all purposes.

FIELD OF THE INVENTION

The present invention is directed to compositions, including vaccine compositions, for generating an immune response to a hemorrhagic fever virus, as well as methods of manufacture and methods of use thereof. Hemorrhagic fever viruses include filoviruses (members of family Filoviridae), such as members of genera *Ebolavirus* and *Marburgvirus*; and arenaviruses (members of family Arenaviridae) such as members of genus *Arenavirus*. More specifically, the compositions and methods described herein relate to a modified vaccinia Ankara (MVA) vector encoding one or more viral antigens for generating a protective immune response in the subject to which the vector is inhibited to a member of genus *Ebolavirus* (such as a member of species *Zaire ebolavirus*), a member of genus *Marburgvirus* (such as a member of species *Marburg marburgvirus*), or a member of genus *Arenavirus* (such as a member of species *Lassa virus*). The compositions and methods of the present invention are useful both prophylactically and therapeutically.

INCORPORATION BY REFERENCE

The contents of the xml file named "19101-015US3_ST26_2023-10-19" which was created on Oct. 19, 2023, and is 68.8 KB in size, are hereby incorporated by reference in their entirety.

BACKGROUND OF THE INVENTION

The Filoviridae family is composed of three genera, *Ebolavirus, Marburgvirus*, and Cuevavirus. Genera *Ebolavirus* and *Marburgvirus* include highly pathogenic and virulent viruses causing rapidly fatal hemorrhagic fever in humans and non-human primates. Genus *Marburgvirus* has only one known species (*Marburg marburgvirus*), whereas genus *Ebolavirus* is more variable and has five known species.

The five distinct species of genus *Ebolavirus* include *Zaire ebolavirus*, Sudan ebolavirus, Taï Forest ebolavirus, Bundibugyo ebolavirus, and Reston ebolavirus. (Carroll et al., J. Virol., 87(5):2608-2616 (2013). Four of these species (*Zaire ebolavirus*, Sudan ebolavirus, Taï Forest ebolavirus, and Bundibugyo ebolavirus), cause fatal disease in humans.

Known viruses belonging to species *Zaire ebolavirus* are commonly referred to as Ebola viruses. Ebola virus is abbreviated as EBOV. Known viruses belonging to species Sudan ebolavirus are commonly referred to as Sudan viruses. Sudan virus is abbreviated as SUDV. Known viruses belonging to species Taï Forest ebolavirus are commonly referred to as Tai Forest viruses. Tai Forest virus is abbreviated as TAFV. Known viruses belonging to species Bundibugyo ebolavirus are commonly referred to as Bundibugyo viruses. Bundibugyo virus is abbreviated as BDBV. Known viruses belonging to species *Marburg marburgvirus* include Marburg virus (MARV) and Ravn virus (RAVV). (Kuhn et al., Viruses, 6:3663-3682 [2014]) Various forms of filovirus nomenclature and abbreviation have been used in the past. Other known abbreviations for members of this group include ZEBOV for Ebola virus, SEBOV for Sudan virus, CIEBOV for Taï Forest virus, BEBOV for Bundibugyo virus, and REBOV for Reston virus.

In this application, the terms "ebolavirus" or "*Ebolavirus*" (single word, not italicized) will be used to refer to any member of genus *Ebolavirus*, while the terms "marburgvirus" or "*Marburgvirus*" will be used to refer to any member of genus *Marburgvirus*.

The genetic organization of filoviruses is similar, each containing seven genes in a linear, single-stranded, negative-sense RNA genome. Among the viral proteins expressed from the ebolavirus genome, the envelope glycoprotein exists in three alternative forms: a 50-70 kilodalton (kDa) secreted protein encoded by the viral genome (sGP), a 130 kDa transmembrane glycoprotein (GP), and a small secreted glycoprotein (ssGP), which is a smaller (approximately 50 kDa) version of the secreted glycoprotein. Transcripts for the full-length glycoprotein and ssGP are generated by RNA editing. The functions of sGP and ssGP are unknown, while the transmembrane protein mediates viral entry. (Mehedi, M. et al., J. Virol. 85:5406-5414 (2011); Peters, C. J. et al., Filoviridae: Marburg and Ebola Viruses. in Fields Virology. (eds., Fields, B. N., Knipe, D. M. & Howley, P. M.) 1161-1176 (Philadelphia, Lippincott-Raven, 1996); Sanchez, A. et al., PNAS (USA) 93:3602-3607 (1996). Other gene products include the nucleoprotein (NP), matrix proteins VP24 and VP40, the transcription factor VP30, the polymerase cofactor VP35, and the viral polymerase L (Biedenkopf, N. et al., J. Biol. Chem. 288:11165-11174 (2013); Nanbo, A. et al., Scientific Reports 3, doi: 10.1038/srep01206 (2013); reviewed in Peters, C. J. et al., Filovirdae: Marburg and Ebola Viruses. in Fields Virology. (eds., Fields, B. N., Knipe, D. M. & Howley, P. M.) 1161-1176 (Philadelphia, Lippincott-Raven, 1996)). Proteins expressed by marburgviruses are very similar, but marburgvirus does not express sGP or ssGP (Radoshitzsky, S. R. et al.; J. Virol. 85:8502-8513 (2011)).

Although spontaneous variation of their RNA sequence does occur in nature, there appears to be less nucleotide polymorphism within ebolavirus subtypes than among other RNA viruses (Sanchez, A. et al., PNAS (USA) 93:3602-3607 (1996)).

Since Ebola virus was discovered in 1976, more than 20 outbreaks have occurred (source: cdc.gov). The development of countermeasures against filoviruses have largely focused on SUDV and EBOV, the two species that have historically been responsible for nearly all ebolavirus outbreaks. To date, however, no approved vaccine or therapeutic product is available for Filovirus infections. As such, medical professionals have no means to prevent infection other than the traditional methods of isolation and sanitation, and no means to treat infected patients.

Arenaviridae comprises a family of viruses whose members are generally associated with rodent-transmitted diseases in humans. Arenaviruses are divided into two groups: the New World or Tacaribe complex and the Old World or LCM/Lassa complex. *Arenavirus* infections are relatively common in humans in some areas of the world and can cause severe illnesses.

*Lassa virus* (LASV) is an arenavirus that causes Lassa hemorrhagic fever, a type of viral hemorrhagic fever (VHF), in human and non-human primates. *Lassa virus* is an emerging virus and a select agent, requiring containment under Biosafety Level 4 or an equivalent standard. LASV is endemic in West African countries, especially Sierra Leone, the Republic of Guinea, Nigeria, and Liberia, where the annual incidence of infection is between 300,000 and 500,000 cases, resulting in 5,000 deaths per year (Kyei et al. (2015), BMC Infectious Diseases 15:217).

Lassa viruses are enveloped, single-stranded, bisegmented, ambisense RNA viruses (Lashley, Felissa R., and Jerry D. Durham. Emerging Infectious Diseases: Trends and Issues. New York: Springer Pub., 2002). Their genome is contained in two RNA segments that code for two proteins each, one in each sense, for a total of four viral proteins (Ridley, Matt. *Genome: The Autobiography of a Species in 23 Chapters*. New York: HarperCollins, 1999). The large segment encodes a small zinc-binding protein (Z) that regulates transcription and replication, and the RNA polymerase (L). The small segment encodes the nucleoprotein (NP) and the surface glycoprotein precursor (GP, also known as the viral spike), which is proteolytically cleaved into the envelope glycoproteins GP1 and GP2 that bind to the alpha-dystroglycan receptor and mediate host cell entry (Cornu, T. I.; De La Torre, J. C. (2001). RING Finger Z Protein of Lymphocytic Choriomeningitis Virus (LCMV) Inhibits Transcription and RNA Replication of an LCMV S-Segment Minigenome". *Journal of Virology* 75 (19): 9415-9426; Djavani M, et al. (September 1997). "Completion of the Lassa fever virus sequence and identification of a RING finger open reading frame at the L RNA 5' End.". *Virology* 235 (2): 414-8; Cao, W.; Henry, M. D.; Borrow, P.; Yamada, H.; Elder, J. H.; Ravkov, E. V.; Nichol, S. T.; Compans, R. W.; Campbell, K. P.; Oldstone, M. B. (1998). "Identification of -Dystroglycan as a Receptor for Lymphocytic Choriomeningitis Virus and Lassa Fever Virus". *Science* 282 (5396): 2079-2081)

The pathogenesis of the *Lassa virus* remains unclear, but it has been shown that the main targets of the virus are antigen-presenting cells (mainly dendritic cells) and endothelial cells (Mahanty, S.; Hutchinson, K.; Agarwal, S.; McRae, M.; Rollin, P. E.; Pulendran, B. (2003). "Cutting edge: Impairment of dendritic cells and adaptive immunity by Ebola and Lassa viruses". *Journal of immunology,* 170 (6): 2797-2801; Baize, S.; Kaplon, J.; Faure, C.; Pannetier, D.; Georges-Courbot, M. C.; Deubel, V. (2004). "*Lassa virus* infection of human dendritic cells and macrophages is productive but fails to activate cells". *Journal of immunology* (Baltimore, Md.: 1950) 172 (5): 2861-2869). Also, it is reported that *Lassa virus* prevents a host's innate immune system by NP activity. NP encoded in *Lassa virus* is essential in viral replication and transcription, but it also suppresses host innate interferon (IFN) response by inhibiting translocation of IRF-3. NP of *Lassa virus* is reported to have an exonuclease activity to only dsRNAs. dsRNA exonuclease activity of the NP leads to counteract IFN responses by digesting the PAMP which leads to the evasion of host immune responses.

Currently there is no US licensed vaccine for humans against the *Lassa virus*. Lassa fever is one of the most prevalent viral hemorrhagic fevers in West Africa responsible for thousands of deaths annually.

What is therefore needed are vaccine compositions and methods of use to prevent and treat disease caused by hemorrhagic fever virus infection, such as an ebolavirus, marburgvirus, or *Lassa virus* infection.

SUMMARY OF THE INVENTION

The compositions and methods of the invention described herein are useful for generating an immune response to at least one hemorrhagic fever virus in a subject in need thereof. Advantageously, the compositions and methods may be used prophylactically to immunize a subject against ebolavirus, marburgvirus or *Lassa virus* infection, or used therapeutically to prevent, treat or ameliorate the onset and severity of disease.

In a first aspect, the present invention is a recombinant modified vaccinia Ankara (MVA) vector comprising a glycoprotein sequence and a matrix protein sequence, wherein both the glycoprotein sequence and matrix protein sequence are inserted into the MVA vector under the control of promoters compatible with poxvirus expression systems.

In one embodiment, the glycoprotein sequence and the matrix protein sequence are inserted into one or more deletion sites of the MVA vector.

In one embodiment, the glycoprotein sequence and the matrix protein sequence are inserted into the MVA vector in a natural deletion site, a modified natural deletion site, or between essential or non-essential MVA genes.

In another embodiment, the glycoprotein sequence and the matrix protein sequence are inserted into the same natural deletion site, a modified natural deletion site, or between the same essential or non-essential MVA genes In another embodiment, the glycoprotein sequence and the matrix protein sequence are inserted into a deletion site selected from I, II, III, IV, V or VI and the matrix protein sequence is inserted into a deletion site selected from I, II, III, IV, V or VI.

In another embodiment, the glycoprotein sequence and the matrix protein sequence are inserted into different natural deletion sites, modified deletion sites, or between different essential or non-essential MVA genes.

In another embodiment, the glycoprotein sequence is inserted in a first deletion site and matrix protein sequence is inserted into a second deletion site.

In a particular embodiment, the glycoprotein sequence is inserted between two essential and highly conserved MVA genes; and the matrix protein sequence is inserted into a restructured and modified deletion III.

In one embodiment, the deletion III is modified to remove non-essential sequences and insert the matrix protein sequence between essential genes.

In a particular embodiment, the matrix protein sequence is inserted between MVA genes, I8R and G1L.

In a particular embodiment, the glycoprotein sequence is inserted between two essential and highly conserved MVA genes to limit the formation of viable deletion mutants.

In a particular embodiment, the glycoprotein protein sequence is inserted between MVA genes, I8R and G1L.

In one embodiment, the promoter is selected from the group consisting of Pm2H5, Psyn II, and mH5 promoters or combinations thereof.

In one embodiment, the glycoprotein sequence is optimized. In a particular embodiment, the glycoprotein sequence is optimized by changing selected codons to other synonymous codons that are optimal for protein expression by MVA, interrupting homopolymer stretches using silent mutations, interrupting transcription terminator motifs using silent mutations, or leading to expression of the transmembrane (rather than secreted) form of glycoprotein, and combinations thereof.

In one embodiment, the recombinant MVA viral vector expresses glycoprotein and matrix proteins that assemble into VLPs.

In one embodiment, the glycoprotein sequence and the matrix protein sequence are from a Filovirus species selected from the group of consisting of *Zaire ebolavirus*, Sudan ebolavirus, Taï forest ebolavirus, Bundibugyo ebolavirus, Reston ebolavirus, and *Marburg marburgvirus*, or a combination thereof.

In a particular embodiment, the glycoprotein sequence and the matrix protein sequence are from a *Zaire ebolavirus*.

In a particular embodiment, the glycoprotein sequence and the matrix protein sequence are from a 2014 epidemic strain of *Zaire ebolavirus*.

In a particular embodiment, the glycoprotein sequence and the matrix protein sequence are from a Sudan ebolavirus.

In a particular embodiment, the glycoprotein sequence and the matrix protein sequence are from a Bundibugyo ebolavirus.

In a particular embodiment, the glycoprotein sequence is from *Zaire ebolavirus* and the matrix protein sequence is from a Sudan ebolavirus.

In a particular embodiment, the glycoprotein sequence is from *Zaire ebolavirus* and the matrix protein sequence is from Bundibugyo ebolavirus.

In a particular embodiment, the glycoprotein sequence is from Sudan ebolavirus and the matrix protein sequence is from a *Zaire ebolavirus*.

In a particular embodiment, the glycoprotein sequence is from a Sudan ebolavirus and the matrix protein sequence is from a Bundibugyo ebolavirus.

In a particular embodiment, the glycoprotein sequence is from a Bundibugyo ebolavirus and the matrix protein sequence is from a Sudan ebolavirus.

In a particular embodiment, the glycoprotein sequence is from a Bundibugyo ebolavirus and the matrix protein sequence is from a *Zaire ebolavirus*.

In a particular embodiment, the glycoprotein sequence and the matrix protein sequence are from a *Marburg marburgvirus*.

In a particular embodiment, the glycoprotein sequence and the matrix protein sequence are from a *Lassa virus*.

In one embodiment, the recombinant MVA viral vector expresses *Lassa virus* glycoprotein and Z proteins that assemble into VLPs.

In one embodiment, the recombinant MVA viral vector expresses *Lassa virus* glycoprotein, NP and Z proteins that assemble into VLPs.

In a second aspect, the present invention is a pharmaceutical composition comprising the recombinant MVA vector of the present invention and a pharmaceutically acceptable carrier.

In one embodiment, the recombinant MVA vector is formulated for intraperitoneal, intramuscular, intradermal, epidermal, mucosal or intravenous administration.

In a third aspect, the present invention is a pharmaceutical composition comprising a first recombinant MVA vector and a second recombinant MVA vector, each comprising a glycoprotein sequence and a matrix protein sequence, wherein (i) the glycoprotein sequence of the first recombinant MVA vector is different than the glycoprotein sequence of the second recombinant MVA vector and/or (ii) the matrix protein sequence of the first recombinant MVA vector is different than the matrix protein sequence of the second recombinant MVA vector.

In a particular embodiment, the glycoprotein sequence of the first recombinant MVA vector is from a different species than the glycoprotein sequence of the second recombinant MVA vector.

In a particular embodiment, the glycoprotein sequences of the recombinant MVA vectors are from a *Zaire ebolavirus* and a Bundibugyo ebolavirus.

In a particular embodiment, the glycoprotein sequences of the recombinant MVA vectors are from a *Zaire ebolavirus* and a Sudan ebolavirus.

In a particular embodiment, the glycoprotein sequences of the recombinant MVA vectors are from a Sudan ebolavirus and a Bundibugyo ebolavirus.

In a particular embodiment, the glycoprotein sequences of the recombinant MVA vectors are from a *Zaire ebolavirus* and a *Marburg marburgvirus*.

In a particular embodiment, the glycoprotein sequences of the recombinant MVA vectors are from a Sudan ebolavirus and a *Marburg marburgvirus*.

In a particular embodiment, the glycoprotein sequences of the recombinant MVA vectors are from a Bundibugyo ebolavirus and a *Marburg marburgvirus*.

In a particular embodiment, the glycoprotein sequences of the recombinant MVA vectors are from a *Zaire ebolavirus* and a *Lassa virus*.

In a particular embodiment, the glycoprotein sequences of the recombinant MVA vectors are from a Sudan ebolavirus and a *Lassa virus*.

In a particular embodiment, the glycoprotein sequences of the recombinant MVA vectors are from a Bundibugyo ebolavirus and a *Lassa virus*.

In a particular embodiment, the glycoprotein sequences of the recombinant MVA vectors are from a *Marburg marburgvirus* and a *Lassa virus*.

In another particular embodiment, the matrix protein sequence of the first recombinant MVA vector is from a different species than the matrix protein sequence of the second recombinant MVA vector.

In a particular embodiment, the matrix protein sequences of the recombinant MVA vectors are from a *Zaire ebolavirus* and a Bundibugyo ebolavirus.

In a particular embodiment, the matrix protein sequences of the recombinant MVA vectors are from a *Zaire ebolavirus* and a Sudan ebolavirus.

In a particular embodiment, the matrix protein sequences of the recombinant MVA vectors are from a Sudan ebolavirus and a Bundibugyo ebolavirus.

In a particular embodiment, the matrix protein sequences of the recombinant MVA vectors are from a *Zaire ebolavirus* and a *Marburg marburgvirus*.

In a particular embodiment, the matrix protein sequences of the recombinant MVA vectors are from a Sudan ebolavirus and a *Marburg marburgvirus*.

In a particular embodiment, the matrix protein sequences of the recombinant MVA vectors are from a Bundibugyo ebolavirus and a *Marburg marburgvirus*.

In a particular embodiment, the matrix protein sequences of the recombinant MVA vectors are from a *Zaire ebolavirus* and a *Lassa virus*.

In a particular embodiment, the matrix protein sequences of the recombinant MVA vectors are from a Sudan ebolavirus and a *Lassa virus*.

In a particular embodiment, the matrix protein sequences of the recombinant MVA vectors are from a Bundibugyo ebolavirus and a *Lassa virus*.

In a particular embodiment, the matrix protein sequences of the recombinant MVA vectors are from a *Marburg marburgvirus* and a *Lassa virus*.

In a fourth aspect, the present invention is a pharmaceutical composition comprising three or more recombinant MVA vectors each comprising a glycoprotein sequence and a matrix protein sequence, wherein (i) the three or more recombinant MVA vectors contain different glycoprotein sequences and/or (ii) the three recombinant MVA vectors contain different matrix protein sequences.

In a particular embodiment, the glycoprotein sequence and matrix sequence of each recombinant vector are from the same species.

In a particular embodiment, the glycoprotein sequences of the three or more recombinant MVA vectors are from different species.

In a particular embodiment, the glycoprotein sequences of the three or more recombinant MVA vectors are from a *Zaire ebolavirus*, a Sudan ebolavirus, and a Bundibugyo ebolavirus.

In a particular embodiment, the glycoprotein sequences of the three or more recombinant MVA vectors are from a *Zaire ebolavirus*, a Sudan ebolavirus, and a *Marburg marburgvirus*.

In a particular embodiment, the glycoprotein sequences of the three or more recombinant MVA vectors are from a *Zaire ebolavirus*, a Sudan ebolavirus, and a *Lassa virus*.

In a particular embodiment, the glycoprotein sequences of the three or more recombinant MVA vectors are from a *Zaire ebolavirus*, a Bundibugyo ebolavirus, and a *Marburg marburgvirus*.

In a particular embodiment, the glycoprotein sequences of the three or more recombinant MVA vectors are from a *Zaire ebolavirus*, a Bundibugyo ebolavirus, and a *Lassa virus*.

In a particular embodiment, the glycoprotein sequences of the three or more recombinant MVA vectors are from a *Zaire ebolavirus*, a *Marburg marburgvirus*, and a *Lassa virus*.

In a particular embodiment, the glycoprotein sequences of the three or more recombinant MVA vectors are from a Sudan ebolavirus, a Bundibugyo ebolavirus, and a *Marburg marburgvirus*.

In a particular embodiment, the glycoprotein sequences of the three or more recombinant MVA vectors are from a Sudan ebolavirus, a Bundibugyo ebolavirus, and a *Lassa virus*.

In a particular embodiment, the glycoprotein sequences of the three or more recombinant MVA vectors are from a Sudan ebolavirus, a *Marburg marburgvirus*, and a *Lassa virus*.

In a particular embodiment, the glycoprotein sequences of the three or more recombinant MVA vectors are from a Bundibugyo ebolavirus, a *Marburg marburgvirus*, and a *Lassa virus*.

In a particular embodiment, the glycoprotein sequences of the three or more recombinant MVA vectors are from a *Zaire ebolavirus*, a Sudan ebolavirus, a Bundibugyo ebolavirus, and a *Marburg marburgvirus*.

In a particular embodiment, the glycoprotein sequences of the three or more recombinant MVA vectors are from a *Zaire ebolavirus*, a Sudan ebolavirus, a Bundibugyo ebolavirus, and a *Lassa virus*.

In a particular embodiment, the glycoprotein sequences of the three or more recombinant MVA vectors are from a Sudan ebolavirus, a Bundibugyo ebolavirus, a *Marburg marburgvirus*, and a *Lassa virus*.

In a particular embodiment, the glycoprotein sequences of the three or more recombinant MVA vectors are from a *Zaire ebolavirus*, a Bundibugyo ebolavirus, a *Marburg marburgvirus*, and a *Lassa virus*.

In a particular embodiment, the glycoprotein sequences of the three or more recombinant MVA vectors are from a *Zaire ebolavirus*, a Sudan ebolavirus, a Bundibugyo ebolavirus, a *Marburg marburgvirus*, and a *Lassa virus*.

In a particular embodiment, the matrix protein sequences of the three or more recombinant MVA vectors are from different species.

In a particular embodiment, the matrix protein sequences of the three or more recombinant MVA vectors are from a *Zaire ebolavirus*, a Sudan ebolavirus, and a Bundibugyo ebolavirus.

In a particular embodiment, the matrix protein sequences of the three or more recombinant MVA vectors are from a *Zaire ebolavirus*, a Sudan ebolavirus, and a *Marburg marburgvirus*.

In a particular embodiment, the matrix protein sequences of the three or more recombinant MVA vectors are from a *Zaire ebolavirus*, a Sudan ebolavirus, and a *Lassa virus*.

In a particular embodiment, the matrix protein sequences of the three or more recombinant MVA vectors are from a *Zaire ebolavirus*, a Bundibugyo ebolavirus, and a *Marburg marburgvirus*.

In a particular embodiment, the matrix protein sequences of the three or more recombinant MVA vectors are from a *Zaire ebolavirus*, a Bundibugyo ebolavirus, and a *Lassa virus*.

In a particular embodiment, the matrix protein sequences of the three or more recombinant MVA vectors are from a *Zaire ebolavirus*, a *Marburg marburgvirus*, and a *Lassa virus*.

In a particular embodiment, the matrix protein sequences of the three or more recombinant MVA vectors are from a Sudan ebolavirus, a Bundibugyo ebolavirus, and a *Marburg marburgvirus*.

In a particular embodiment, the matrix protein sequences of the three or more recombinant MVA vectors are from a Sudan ebolavirus, a Bundibugyo ebolavirus, and a *Lassa virus*.

In a particular embodiment, the matrix protein sequences of the three or more recombinant MVA vectors are from a Sudan ebolavirus, a *Marburg marburgvirus*, and a *Lassa virus*.

In a particular embodiment, the matrix protein sequences of the three or more recombinant MVA vectors are from a Bundibugyo ebolavirus, a *Marburg marburgvirus*, and a *Lassa virus*.

In a particular embodiment, the matrix protein sequences of the three or more recombinant MVA vectors are from a *Zaire ebolavirus*, a Sudan ebolavirus, a Bundibugyo ebolavirus, and a *Marburg marburgvirus*.

In a particular embodiment, the matrix protein sequences of the three or more recombinant MVA vectors are from a *Zaire ebolavirus*, a Sudan ebolavirus, a Bundibugyo ebolavirus, and a *Lassa virus*.

In a particular embodiment, the matrix protein sequences of the three or more recombinant MVA vectors are from a Sudan ebolavirus, a Bundibugyo ebolavirus, a *Marburg marburgvirus*, and a *Lassa virus*.

In a particular embodiment, the matrix protein sequences of the three or more recombinant MVA vectors are from a

*Zaire ebolavirus*, a Bundibugyo ebolavirus, a *Marburg marburgvirus*, and a *Lassa virus*.

In a particular embodiment, the matrix protein sequences of the three or more recombinant MVA vectors are from a *Zaire ebolavirus*, a Sudan ebolavirus, a Bundibugyo ebolavirus, a *Marburg marburgvirus*, and a *Lassa virus*.

In a fifth aspect, the present invention is a method of inducing an immune response in a subject in need thereof, said method comprising administering the composition of the present invention to the subject in an amount sufficient to induce an immune response.

In one embodiment, the immune response is a humoral immune response, a cellular immune response or a combination thereof.

In a particular embodiment, the immune response comprises production of binding antibodies against the ebolavirus, marburgvirus, or *Lassa virus*.

In a particular embodiment, the immune response comprises production of neutralizing antibodies against the ebolavirus, marburgvirus, or *Lassa virus*.

In a particular embodiment, the immune response comprises production of non-neutralizing antibodies against the ebolavirus, marburgvirus, or *Lassa virus*.

In a particular embodiment, the immune response comprises production of a cell-mediated immune response against the ebolavirus, marburgvirus, or *Lassa virus*.

In a particular embodiment, the immune response comprises production of neutralizing and non-neutralizing antibodies against the ebolavirus, marburgvirus, or *Lassa virus*.

In a particular embodiment, the immune response comprises production of neutralizing antibodies and cell-mediated immunity against the ebolavirus, marburgvirus, or *Lassa virus*.

In a particular embodiment, the immune response comprises production of non-neutralizing antibodies and cell-mediated immunity against the ebolavirus, marburgvirus, or *Lassa virus*.

In a particular embodiment, the immune response comprises production of neutralizing antibodies, non-neutralizing antibodies, and cell-mediated immunity against the ebolavirus, marburgvirus, or *Lassa virus*.

In a sixth aspect, the present invention is a method of preventing a hemorrhagic fever virus infection in a subject in need thereof, said method comprising administering the recombinant MVA vector of the present invention to the subject in a prophylactically effective amount.

In one embodiment, the hemorrhagic fever infection is an ebolavirus, marburgvirus, or *Lassa virus* infection.

In one embodiment, the method prevents infection by a *Zaire ebolavirus*.

In another embodiment, the method prevents infection by a Sudan ebolavirus.

In another embodiment, the method prevents infection by a Bundibugyo ebolavirus.

In another embodiment, the method prevents infection by a *Marburg marburgvirus*.

In another embodiment, the method prevents infection by a *Lassa virus*.

In yet another embodiment, the method prevents infection by more than one species of hemorrhagic fever virus, e.g., a *Zaire ebolavirus* and a Sudan ebolavirus or a *Zaire ebolavirus* and a *Marburg marburgvirus* or a *Zaire ebolavirus* and a *Lassa virus*.

In a seventh aspect, the present invention is a method of inducing an immune response in a subject in need thereof, said method comprising administering the recombinant MVA vector of the present invention to the subject in a prophylactically effective amount.

In one embodiment, the immune response is considered a surrogate marker for protection.

In one embodiment, the method induces an immune response against a *Zaire ebolavirus*.

In another embodiment, the method induces an immune response against a Sudan ebolavirus.

In another embodiment, the method induces an immune response to a Bundibugyo ebolavirus.

In another embodiment, the method induces an immune response to a *Marburg marburgvirus*.

In another embodiment, the method induces an immune response to a *Lassa virus*.

In yet another embodiment, the method induces an immune response to more than one species of hemorrhagic fever virus, e.g., a *Zaire ebolavirus* and a Sudan ebolavirus or a *Zaire ebolavirus* and a *Marburg marburgvirus* or a Sudan ebolavirus and a *Lassa virus*

In an eighth aspect, the present invention is a method of treating hemorrhagic fever virus infection in a subject in need thereof, said method comprising administering the recombinant MVA vector in a therapeutically effective amount to the subject.

In one embodiment, the hemorrhagic fever virus infection is caused by an ebolavirus, an marburgvirus or *Lassa virus*.

In one embodiment, the subject is exposed to hemorrhagic fever virus, but not yet symptomatic of hemorrhagic fever virus infection. In a particular embodiment, treatment results in prevention of a symptomatic infection.

In another embodiment, the subject was recently exposed but exhibits minimal symptoms of infections.

In another embodiment, the method results in amelioration of at least one symptom of infection.

In one embodiment, the symptom of infection is fever and/or hemorrhagic bleeding.

In another embodiment, the method results in reduction or elimination of the subject's ability to transmit the infection to an uninfected subject.

In one embodiment, the method prevents or ameliorates a *Zaire ebolavirus* infection.

In another embodiment, the method prevents or ameliorates a Sudan ebolavirus infection.

In another embodiment, the method prevents or ameliorates a Bundibugyo ebolavirus infection.

In another embodiment, the method prevents or ameliorates a *Marburg marburgvirus* infection.

In another embodiment, the method prevents or ameliorates a *Lassa virus* infection.

In yet another embodiment, the method prevents or ameliorates infections resulting from more than one species of hemorrhagic fever virus, e.g., *Zaire ebolavirus* and Sudan ebolavirus infections or *Zaire ebolavirus* and *Marburg marburgvirus* infections or Bundibugyo ebolavirus and *Lassa virus* infections.

In a ninth aspect, the present invention is a method manufacturing a recombinant modified vaccinia Ankara (MVA) vector comprising inserting at least one glycoprotein sequence and at least one matrix protein sequence into the MVA vector operably linked to promoters compatible with poxvirus expression systems.

In one embodiment, the matrix sequence is VP40, and the GP sequence and the VP40 sequence are from a Filovirus species selected from the group consisting of *Zaire ebolavirus*, Sudan ebolavirus, nil forest ebolavirus, Bundibugyo ebolavirus, Reston ebolavirus, and *Marburg marburgvirus*, or a combination thereof.

In a particular embodiment, the GP sequence and the VP40 sequence are from a *Zaire ebolavirus*.

In a particular embodiment, the GP sequence and the VP40 sequence are from a 2014 epidemic strain of *Zaire ebolavirus*.

In a particular embodiment, the GP sequence and the VP40 sequence are from a Sudan ebolavirus.

In a particular embodiment, the GP sequence and the VP40 sequence are from a Bundibugyo ebolavirus.

In a particular embodiment, the GP sequence is from *Zaire ebolavirus* and the VP40 sequence is from a Sudan ebolavirus.

In a particular embodiment, the GP sequence is from *Zaire ebolavirus* and the VP40 sequence is from Bundibugyo ebolavirus.

In a particular embodiment, the GP sequence is from Sudan ebolavirus and the VP40 sequence is from a *Zaire ebolavirus*.

In a particular embodiment, the GP sequence is from a Sudan ebolavirus and the VP40 sequence is from a Bundibugyo ebolavirus.

In a particular embodiment, the GP sequence is from a Bundibugyo ebolavirus and the VP40 sequence is from a Sudan ebolavirus.

In a particular embodiment, the GP sequence is from a Bundibugyo ebolavirus and the VP40 sequence is from a *Zaire ebolavirus*.

In a particular embodiment, the GP sequence and the VP40 sequence are from a *Marburg marburgvirus*.

In a particular embodiment, the GP sequence is from a *Lassa virus*, and the matrix protein sequence is a Z sequence from a *Lassa virus*.

In a particular embodiment, the GP sequence is from a *Lassa virus*, the matrix protein sequence is a Z sequence from a *Lassa virus* and further comprises a nucleoprotein (NP) sequence from *Lassa virus*.

In one embodiment, the recombinant MVA viral vector expresses *Lassa virus* glycoprotein and matrix proteins that assemble into VLPs.

The numbering illustrates the positions (in kilobase pairs) of the various elements in the genome of the MVA vaccine vector. For clarity and brevity, the diagram is not to scale; pairs of diagonal lines indicate a section of the MVA genome that is not illustrated because its contents are not relevant to the invention. Arrows labeled "gp" and "vp40" illustrate the positions of the genes encoding GP and VP40, respectively for use with ebolavirus or *Marburgvirus* sequences. Rectangles labeled "I8R" and "G1L" indicate the positions of the two MVA genetic elements flanking the gene encoding GP. Rectangles labeled "A50R" and "B1R" indicate the positions of the two MVA genetic elements flanking the gene encoding VP40.

Figure 1:
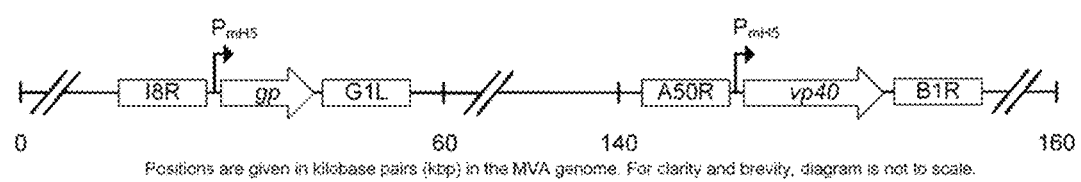
FIG. 1 is a simple line drawing illustrating the design of the MVA vectors.

The design for vectors containing EBOV, SUDV, BDBV, MARV and LASV genes is highly similar; therefore, the diagram in FIG. 1 may apply to the recombinant MVA vaccine vectors described in this application. The "GP" annotation in FIG. 1 indicates a GP sequence from EBOV, SUDV, BDBV, or MARV. The "VP40" annotation in FIG. 1 indicates a VP40 sequence from EBOV, SUDV, BDBV, or MARV. Other embodiments may deviate from this general design and are described herein.

In other embodiments for expressing LASV sequences, this illustration may represent a vector expressing LASV sequences where the GP sequence of FIG. 1 may instead represent the *Lassa virus* GP sequence and the "VP40" sequence of FIG. 1 may instead represent the *Lassa virus* Z sequence. In another embodiment, the "VP40" in FIG. 1 represents the *Lassa virus* Z sequence and NP sequence in reverse orientation each operably linked to a promoter compatible with poxvirus expression systems.

Figure 2:
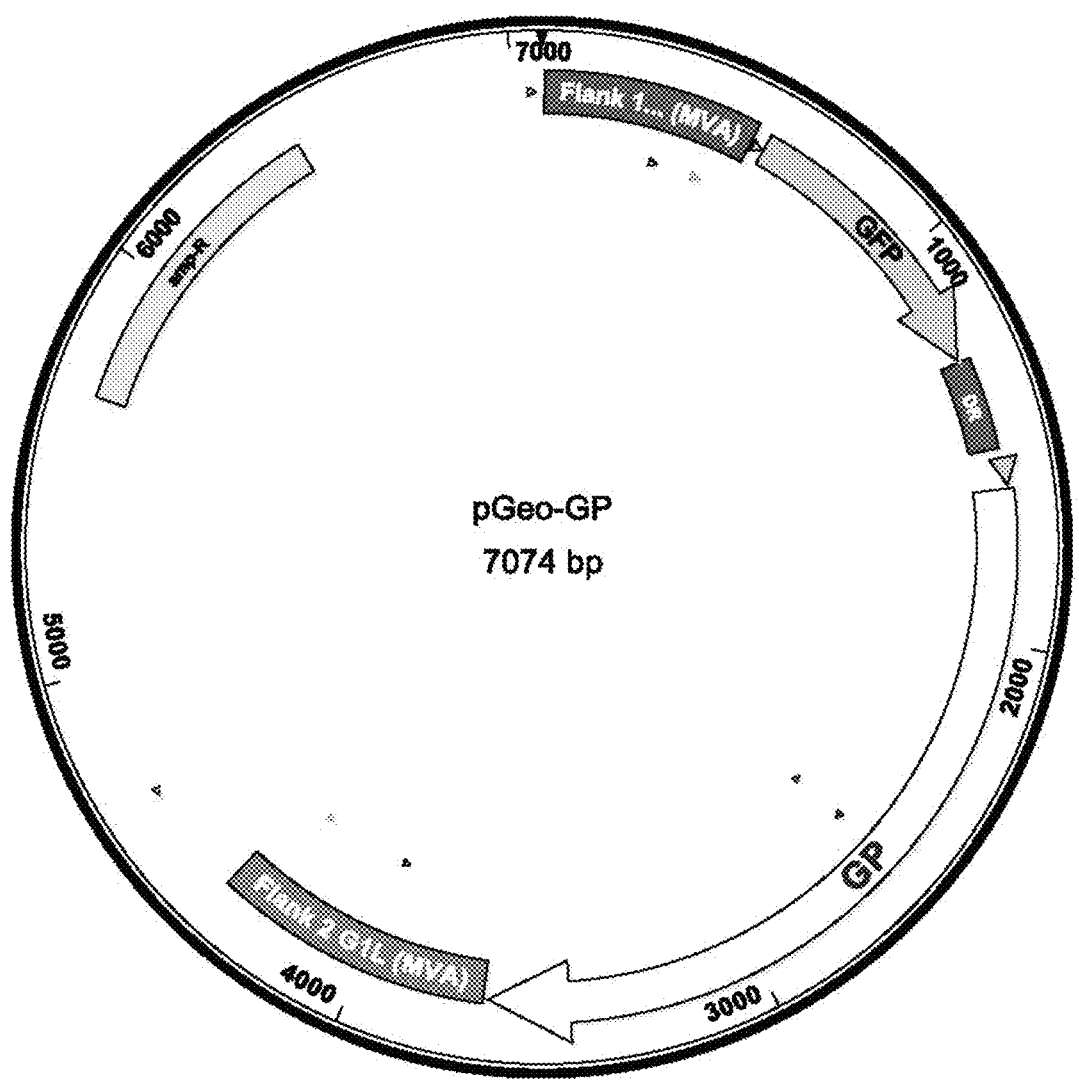

FIG. 2 is a schematic for the shuttle vector for filovirus or Marburg virus GP.

The ampicillin resistance marker, allowing the vector to replicate in bacteria, is illustrated with a block labeled "amp-R." The two flanking sequences, allowing the vector to recombine with the MVA genome, are illustrated with a block and a block labeled "Flank 1" and "Flank 2" respectively. The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of GP into the MVA genome. The modified H5 (mH5) promoter, which enables transcription of the inserted heterologous gene, is illustrated with a triangle between the DR and GP elements. The filovirus GP gene is illustrated with a white arrow labeled "GP."

The shuttle vectors for EBOV, SUDV, BDBV, MARV and LASV glycoproteins use a highly similar design; therefore, FIG. 2 provides a single diagram that applies universally to the MVA vaccine vectors described in this application. FIG. 2 illustrates the design of all glycoprotein shuttle vectors of the invention. The "GP" annotation in FIG. 2 applies to glycoprotein sequences from EBOV, SUDV, BDBV, MARV and LASV.

The shuttle vectors for the various species differ in two principal ways. First, the glycoprotein sequences vary by species. Second, the restriction sites used to insert the glycoprotein sequences into the shuttle vector may vary by species. Neither of these differences affects the orientation of the elements of the shuttle vector.

Figure 3:
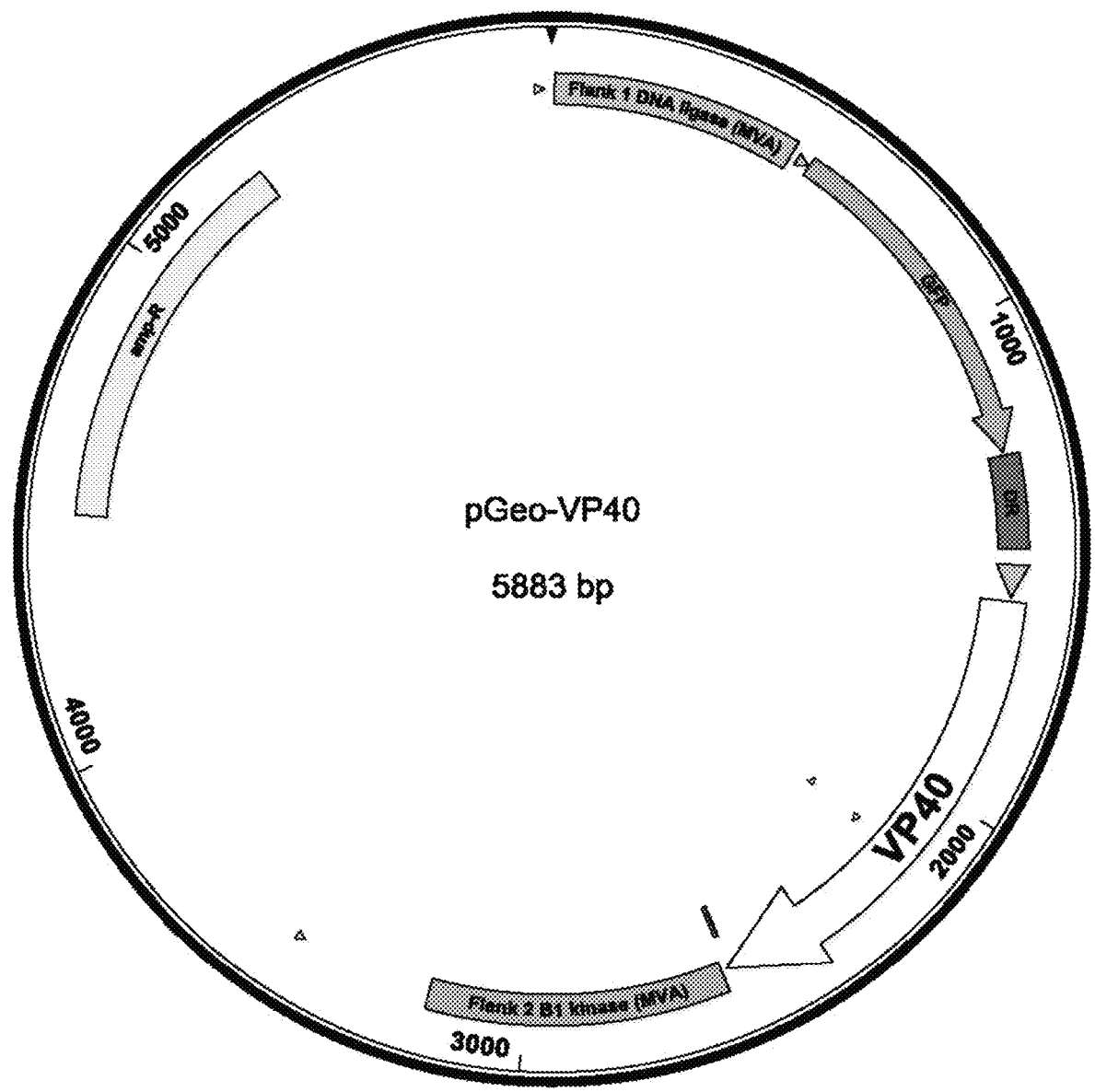

FIG. 3 is a schematic for the shuttle vector for filovirus or Marburg virus VP40.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of VP40 into the MVA genome. The modified H5 (mH5) promoter, which enables transcription of the inserted heterologous gene, is illustrated with a triangle between the DR and VP40 elements. The filovirus VP40 gene is illustrated with a white arrow labeled "VP40."

The shuttle vectors for EBOV, SUDV, BDBV, and MARV VP40s use a highly similar design and naming convention; therefore, FIG. 3 provides a single diagram that applies universally to the MVA vaccine vectors described in this application. FIG. 3 illustrates the design of all VP40 shuttle vectors of the invention. The "VP40" annotation in FIG. 3 applies to VP40 sequences from EBOV, SUDV, BDBV, and MARV.

The shuttle vectors for the various species differ in two principal ways. First, the VP40 sequences vary by species. Second, the restriction sites used to insert the VP40 sequences into the shuttle vector may vary by species. Neither of these differences affects the orientation of the elements of the shuttle vector.

Figure 4A:
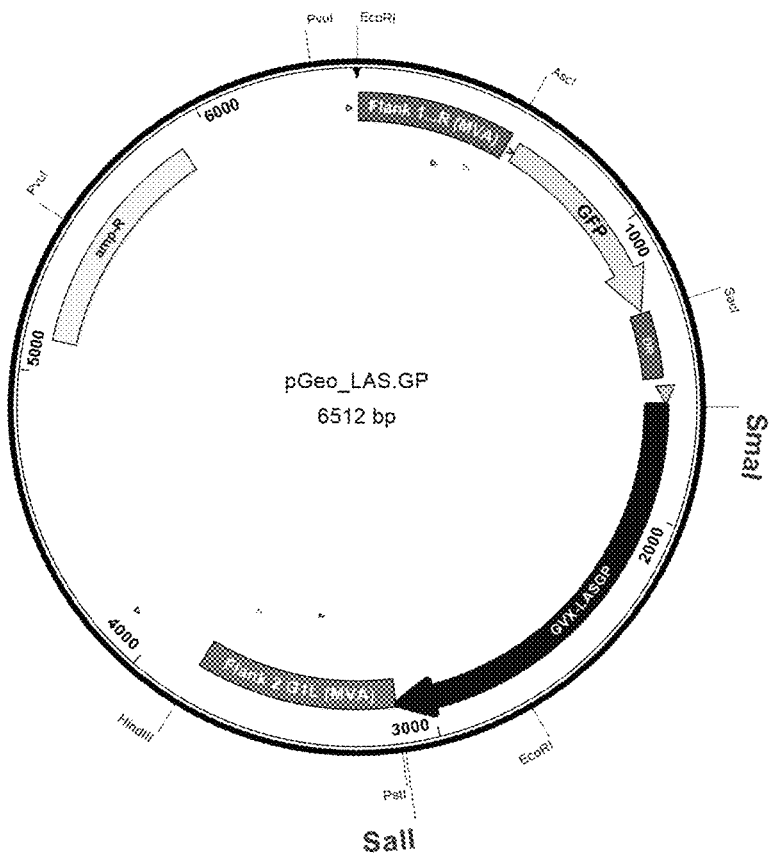
Figure 4B:
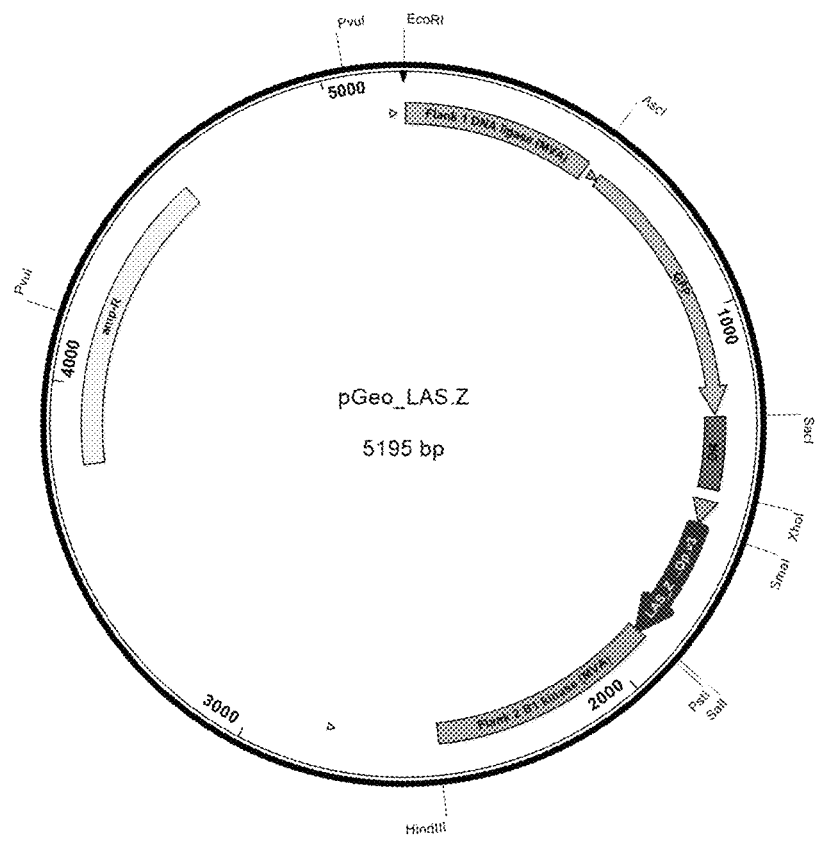

FIG. 4A and FIG. 4B provide a schematic for the shuttle vector for Lassa GP (4A) and Z (4B) genes. The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of GP and Z into the MVA genome. The modified H5 (mH5) promoter and P7.5 promoter, which enable transcription of the inserted heterologous gene, GP and Z respectively, are illustrated with a triangle between the DR and GP or Z elements.

Figure 5:
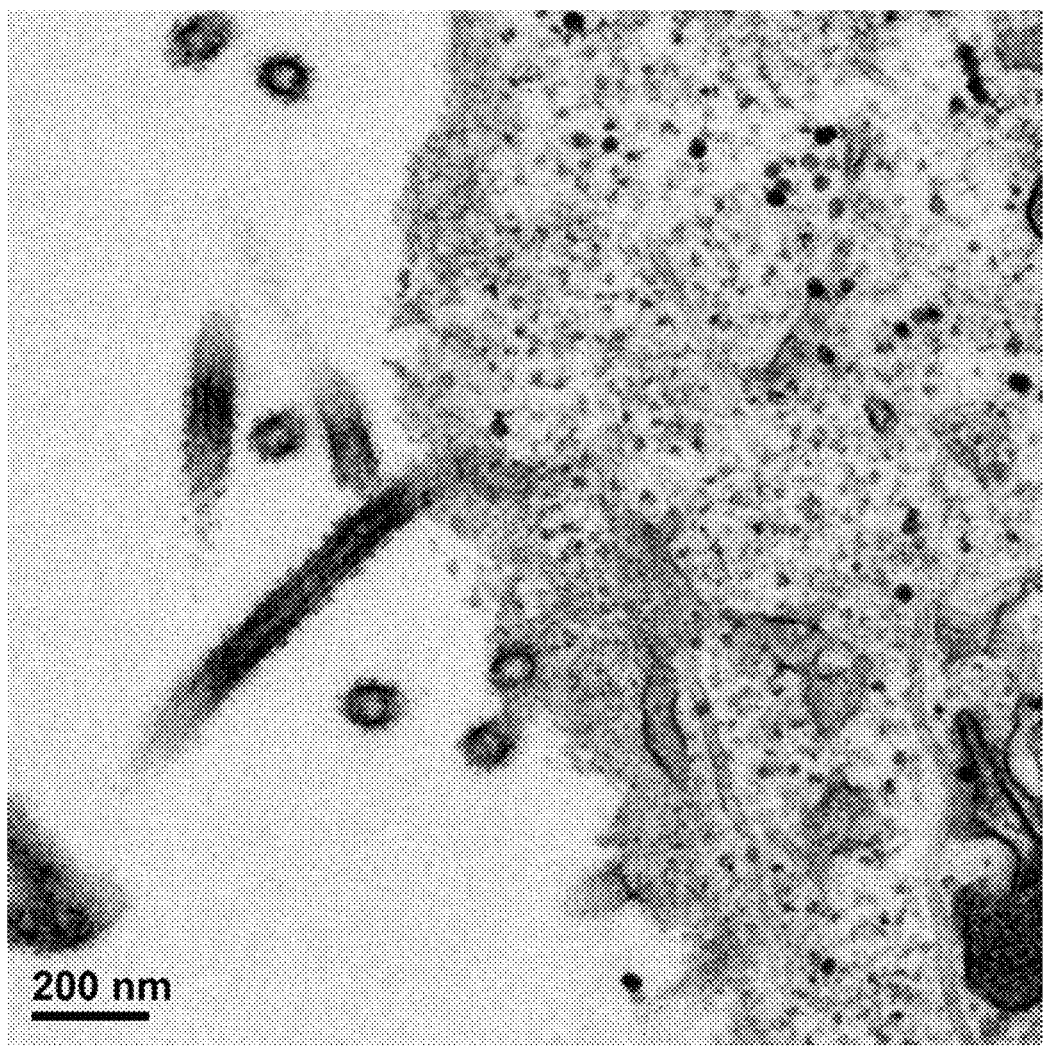

FIG. 5 is an electron micrograph showing virus-like particle (VLP) production by cells transfected with plasmid DNA vectors encoding EBOV GP and VP40 proteins. The sequences of the GP and VP40 in these plasmid DNA vectors are identical to the sequences of the GP and VP40 genes that are used in the MVA vaccine vector that expresses GP and VP40 from the 2014 strain of EBOV. This experiment demonstrated that the 2014 EBOV antigen sequences of this invention are capable of forming VLPs when introduced into cultured cells.

Figure 6:
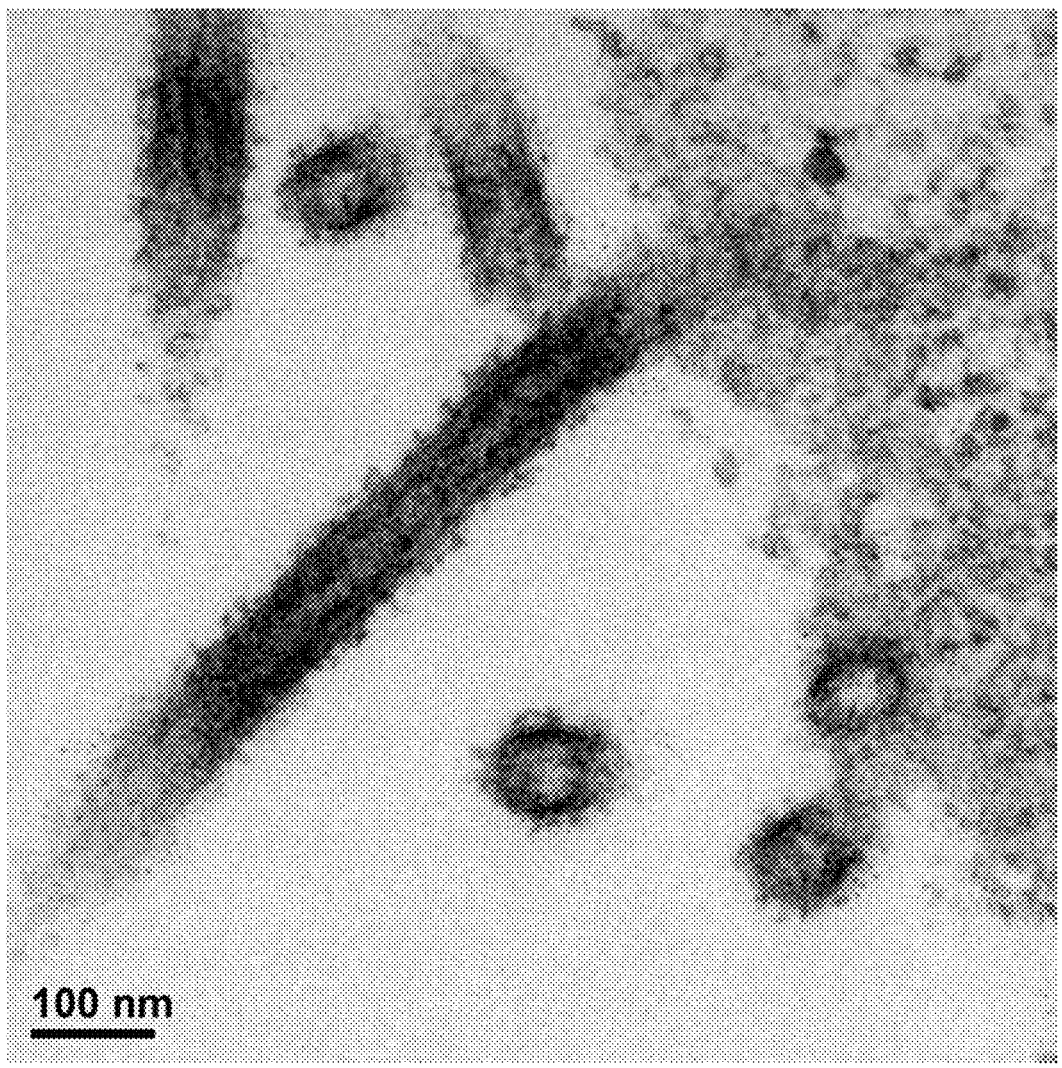

FIG. 6 is a higher magnification of the VLP in FIG. 5 to show the display of ebolavirus GP spikes on the VLP.

Figure 7:
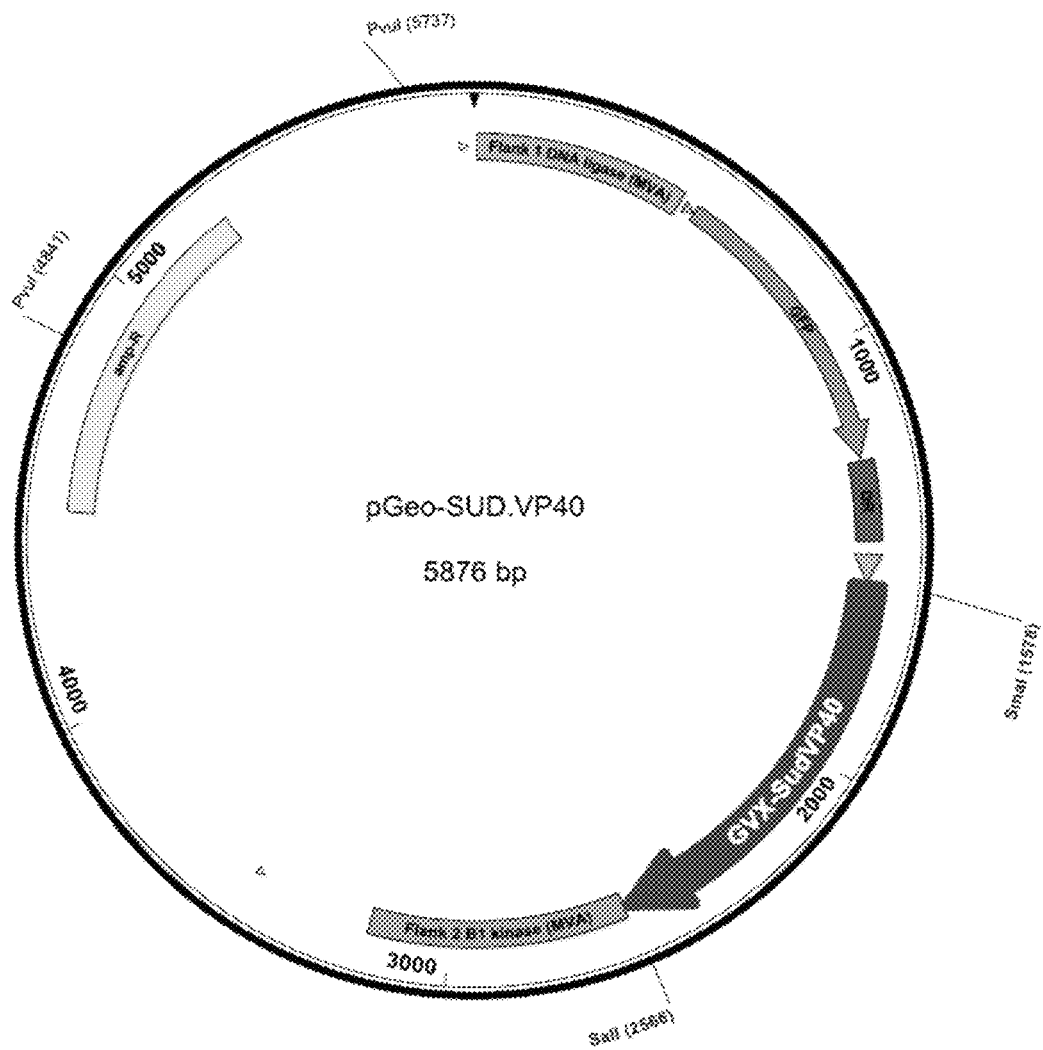

FIG. 7 is a schematic for the shuttle vector for pGEO.SUD.VP40.

Figure 8:
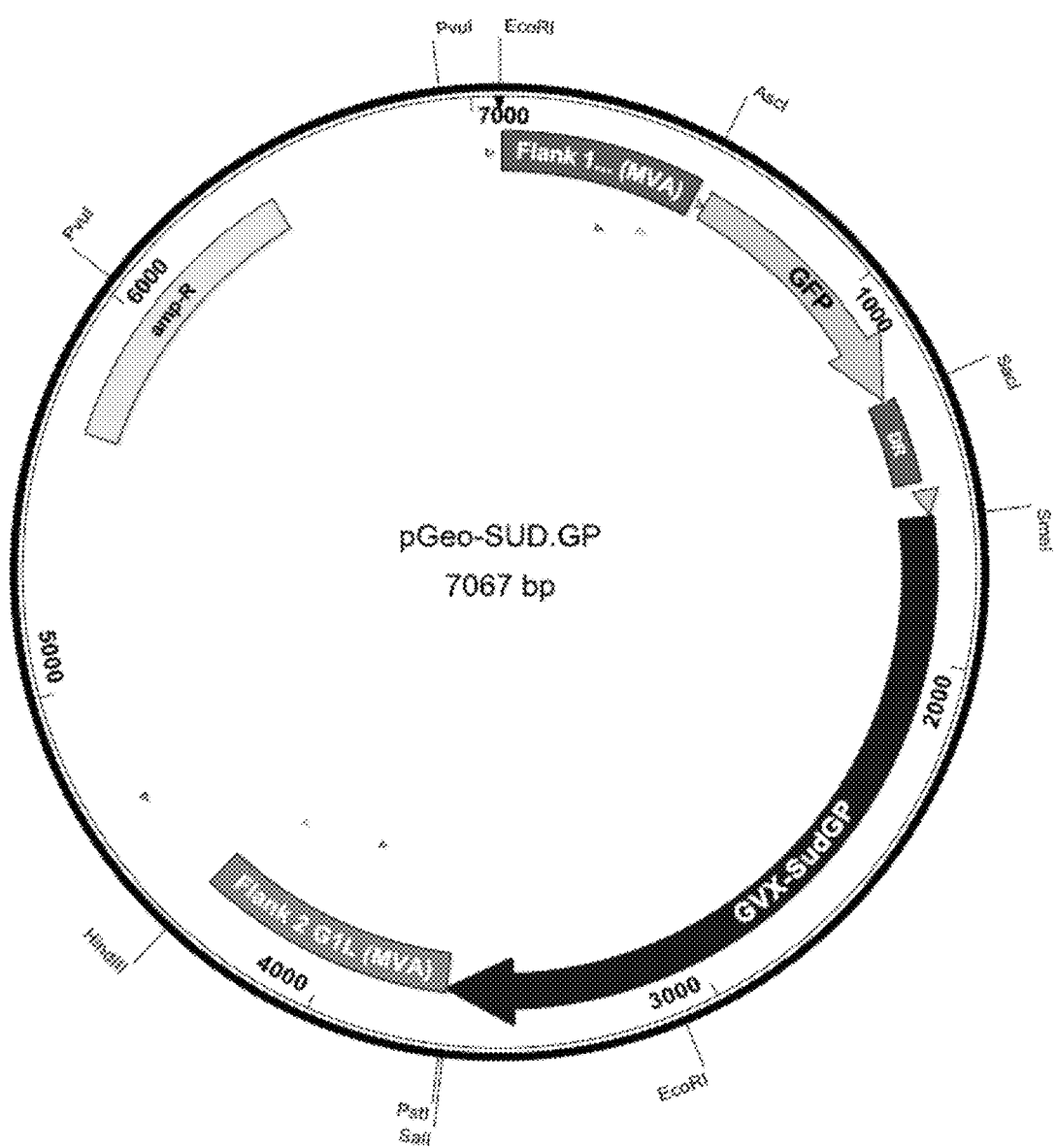

FIG. 8 is a schematic for the shuttle vector for pGEO.SUD.GP.

Figure 9:
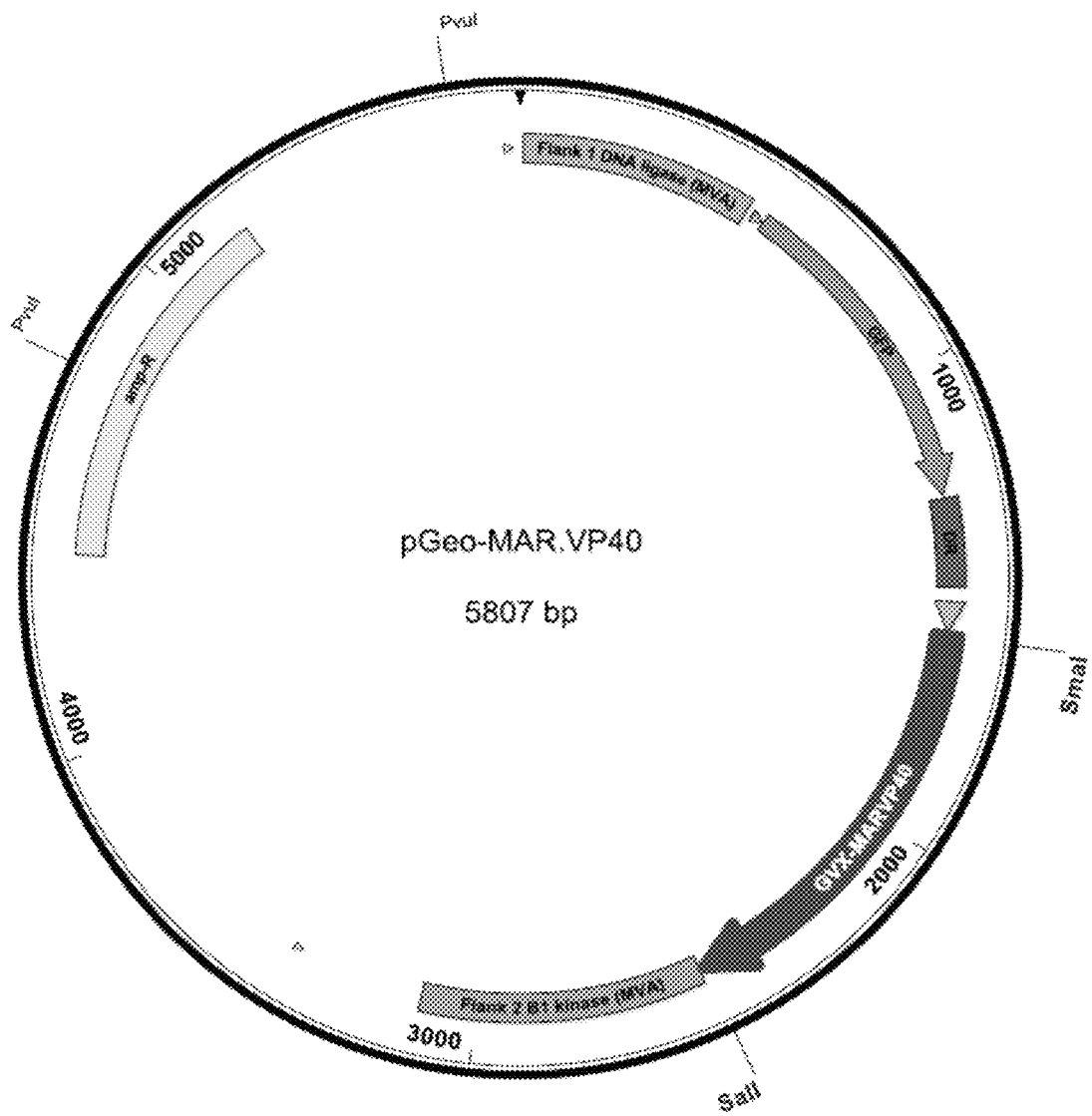

FIG. 9 is a schematic for the shuttle vector for pGEO.MAR.VP40.

Figure 10:
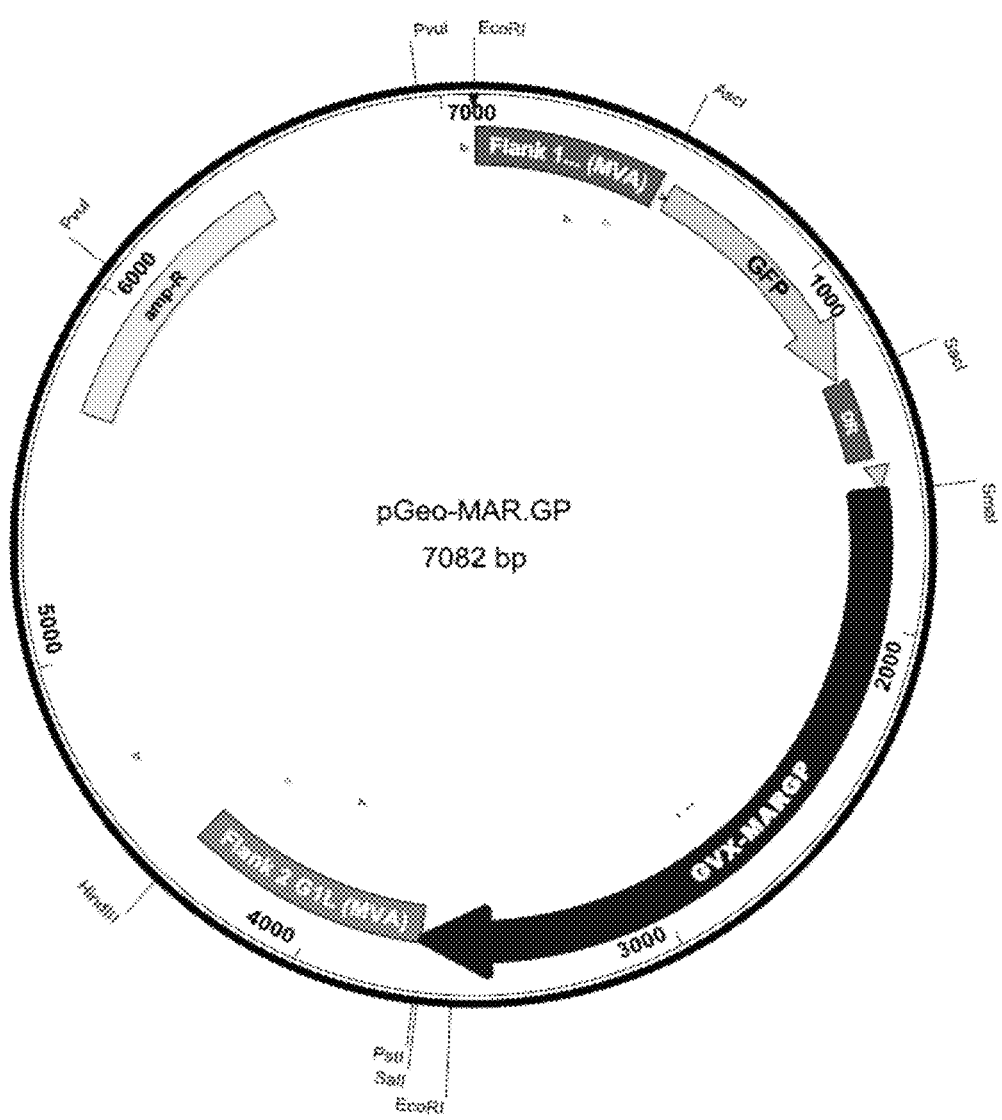

FIG. 10 is a schematic for the shuttle vector for pGEO.MAR.GP.

Figures 11A, 11B:
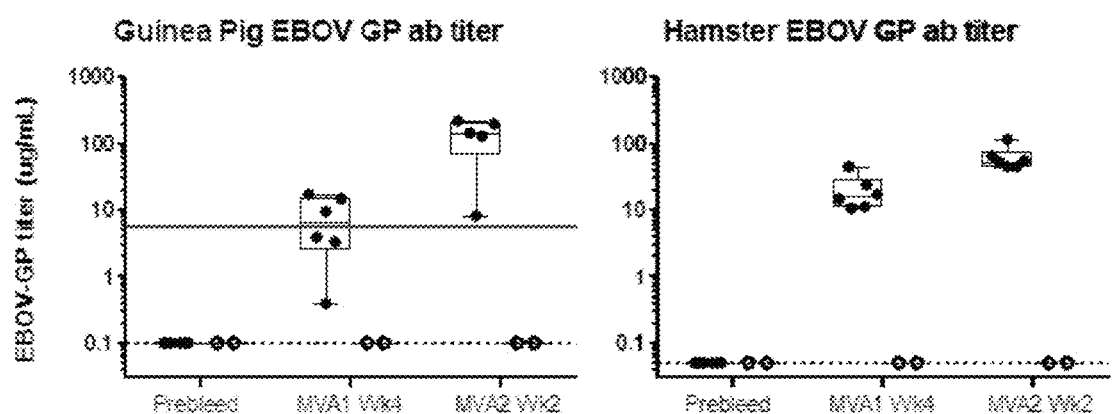

FIG. 11A and FIG. 11B show binding antibody responses to the Ebola virus glycoprotein (GP) elicited by the vaccinations and specifically the results for binding Ab elicited by the MVA/Z-VLP vaccine. Guinea pig sera are shown on the left (FIG. 11A) and Syrian golden hamster sera on the right (FIG. 11B). The closed symbols are for animals receiving MVA/Z-VLP vaccine and the open symbols for animals vaccinated with the parental MVA (no vaccine inserts). The horizontal line in the left panel indicates the titer of binding Ab in sera pooled from six guinea pigs vaccinated with a chimeric vesicular stomatitis virus (VSV) expressing GP. Prebleed is prior to first MVA inoculation; MVA1wk4, four weeks after the first MVA inoculation and MVA2wk2, two weeks after the second MVA inoculation.

Figure 12A:
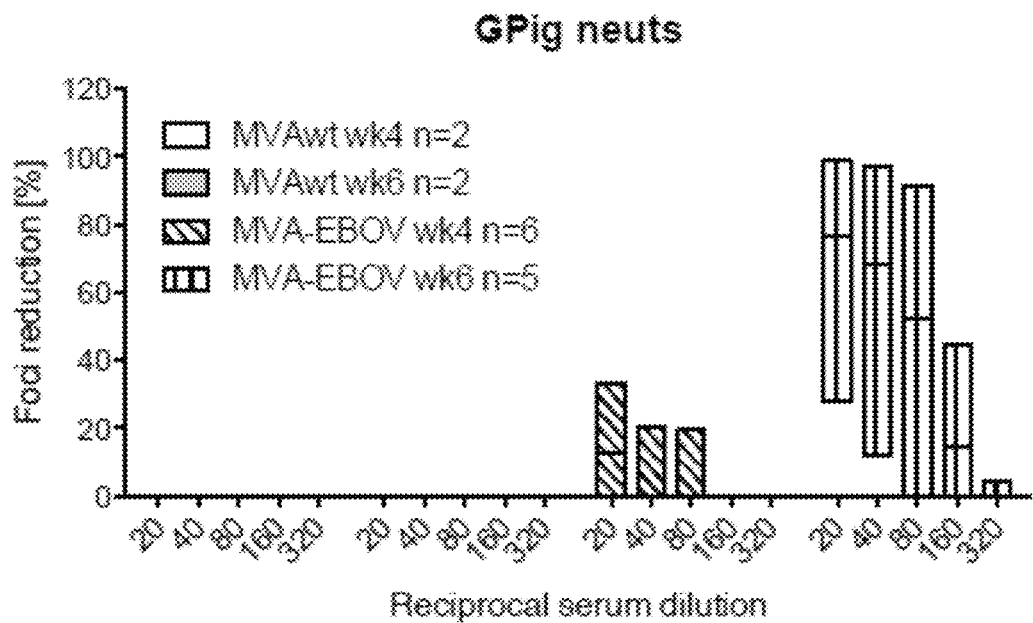
Figure 12B:
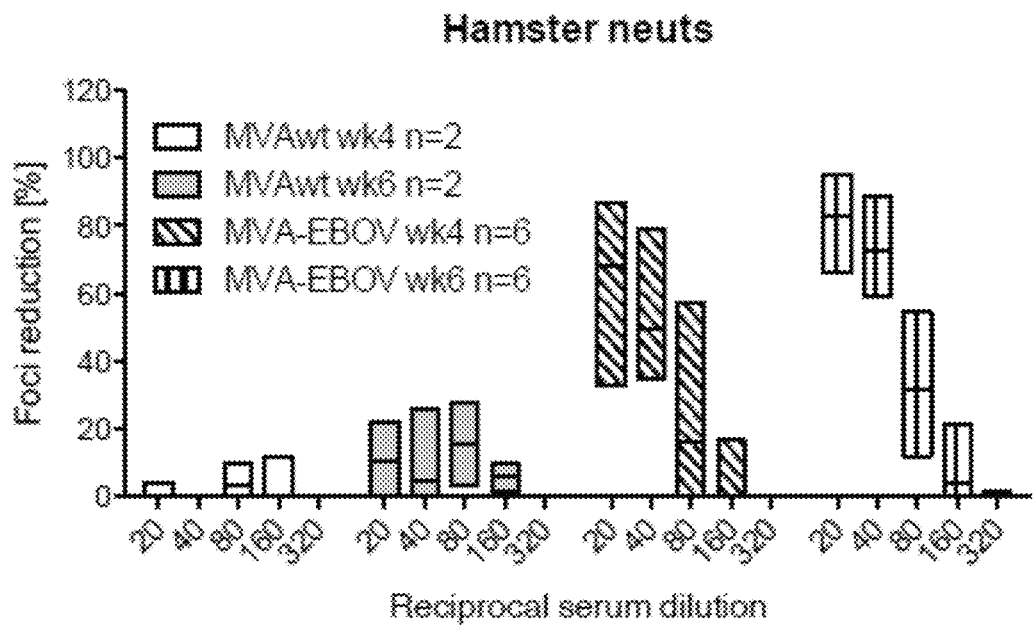

FIG. 12A and FIG. 12B shows neutralizing Ab responses to Ebola virus elicited by the vaccinations and specifically shows the results for neutralizing Ab elicited by the MVA/Z-VLP vaccine. The upper panel (FIG. 12A), GPig shows neutralizing titers elicited in guinea pigs and the bottom panel (FIG. 12B) shows neutralizing titers elicited in SGH. MVAwt are data for animals infected with parental MVA. MVA-EBOV are data for animals vaccinated with MVA/Z-VLP.

Figures 13A, 13B, 13C, 13D:
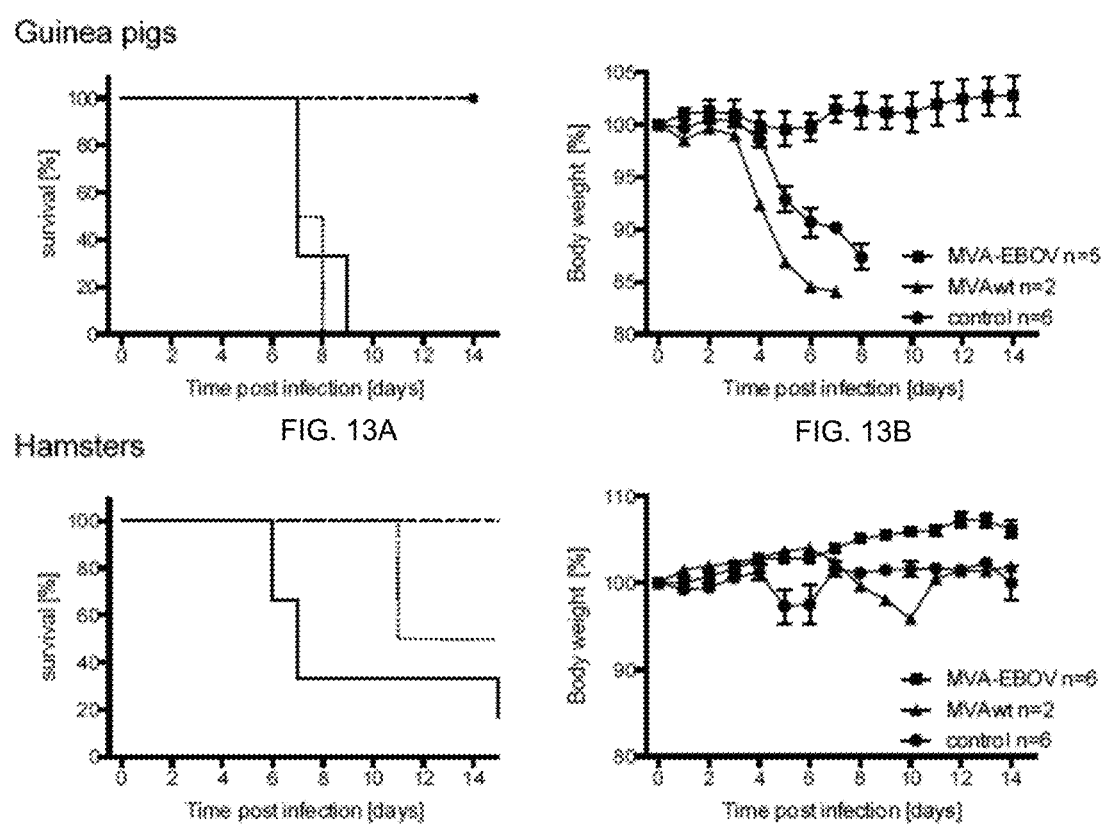

FIG. 13A-FIG. 13B show post challenge survival (left panel FIG. 13A) and body weight charts (right panel FIG. 13B) for guinea pig. FIG. 13C-FIG. 13D show presents post challenge survival (left panel FIG. 13C) and body weight charts (right panel FIG. 13D) for Syrian golden hamster (SGHs). Vaccination with MVA/Z-VLP clearly demonstrates protection against a highly virulent challenge. All of the vaccinated guinea pigs and SGHs survived the challenge.

DETAILED DESCRIPTION OF THE INVENTION

Compositions and methods are provided to produce an immune response to a hemorrhagic fever virus, such as a member of the genus *Ebolavirus, Marburgvirus*, or *Arenavirus*, in a subject in need thereof. The compositions and methods of the present invention can be used to prevent infection in an unexposed person or to treat disease in a subject exposed to a hemorrhagic fever virus who is not yet symptomatic or has minimal symptoms. In one embodiment, treatment limits an infection and/or the severity of disease.

Ideal immunogenic compositions or vaccines have the characteristics of safety, efficacy, scope of protection and longevity, however, compositions having fewer than all of these characteristics may still be useful in preventing viral infection or limiting symptoms or disease progression in an exposed subject treated prior to the development of symptoms. In one embodiment the present invention provides a vaccine that permits at least partial, if not complete, protection after a single immunization.

In one embodiment, the composition is a recombinant vaccine that comprises one or more genes from a hemorrhagic fever virus selected from the group consisting of EBOV, SUDV, BDBV, TAFV, MARV, LASV, and combinations thereof.

In exemplary embodiments, the immune responses are long-lasting and durable so that repeated boosters are not required, but in one embodiment, one or more administrations of the compositions provided herein are provided to boost the initial primed immune response.

Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "antigen" refers to a substance or molecule, such as a protein, or fragment thereof, that is capable of inducing an immune response.

The term "arenavirus" refers to any virus that is a member of the family Arenaviridae.

The term "binding antibody" or "bAb" refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term "Bundibugyo virus" or "BDBV" refers to a virus belonging to species Bundibugyo ebolavirus.

The term ""cell-mediated immune response" refers to the immunological defense provided by lymphocytes, such as the defense provided by sensitized T cell lymphocytes when they directly lyse cells expressing foreign antigens and secrete cytokines (e.g., IFN-gamma.), which can modulate macrophage and natural killer (NK) cell effector functions and augment T cell expansion and differentiation. The cellular immune response is the $2^{nd}$ branch of the adaptive immune response.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term "deletion" in the context of a polypeptide or protein refers to removal of codons for one or more amino acid residues from the polypeptide or protein sequence. The term deletion in the context of a nucleic acid refers to removal of one or more bases from a nucleic acid sequence.

The term "Ebola virus" or "EBOV" refers to a virus belonging to species *Zaire ebolavirus*.

The term "*Ebolavirus*" refers to the genus of the family Filoviridae, order Mononegavirales, which includes the five known species: *Zaire ebolavirus*, Sudan ebolavirus, Tai Forest ebolavirus (also known as Ivory Coast ebolavirus or Cote d'Ivoire ebolavirus (CIEBOV)), Bundibugyo ebolavirus, and Reston ebolavirus.

The term "ebolavirus" or "*Ebolavirus*" refers to any member of the genus *Ebolavirus*.

The term "filovirus" refers collectively to members of the Filoviridae family of single stranded (−) RNA viruses including ebolaviruses and Marburg viruses.

The term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein retains activity of the full-length protein. In another embodiment, the fragment of the full-length protein does not retain the activity of the full-length protein.

The term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein.

As used herein, the term "GP" refers to the ebolavirus or marburgivirus surface glycoprotein, or the gene or transcript encoding the ebolavirus or marburgvirus surface glycoprotein.

As used herein, the phrase "heterologous sequence" refers to any nucleic acid, protein, polypeptide or peptide sequence which is not normally associated in nature with another nucleic acid or protein, polypeptide or peptide sequence of interest.

As used herein, the phrase "heterologous gene insert" refers to any nucleic acid sequence that has been, or is to be inserted into the recombinant vectors described herein. The heterologous gene insert may refer to only the gene product encoding sequence or may refer to a sequence comprising a promoter, a gene product encoding sequence (such as GP, VP or Z), and any regulatory sequences associated or operably linked therewith.

The term "homopolymer stretch" refers to a sequence comprising at least four of the same nucleotides uninterrupted by any other nucleotide, e.g., GGGG or TTTTTTT.

The term "humoral immune response" refers to the stimulation of Ab production. Humoral immune response also refers to the accessory proteins and events that accompany antibody production, including T helper cell activation and cytokine production, affinity maturation, and memory cell generation. The humoral immune response is one of two branches of the adaptive immune response.

The term "humoral immunity" refers to the immunological defense provided by antibody, such as neutralizing Ab that can directly block infection; or, binding Ab that identifies a virus or infected cell for killing by such innate immune responses as complement (C')-mediated lysis, phagocytosis, and natural killer cells.

The term "immune response" refers to any response to an antigen or antigenic determinant by the immune system of a subject (e.g., a human). Exemplary immune responses include humoral immune responses (e.g., production of antigen-specific antibodies) and cell-mediated immune responses (e.g., production of antigen-specific T cells).

The term "improved therapeutic outcome" relative to a subject diagnosed as infected with a particular virus (e.g., an ebolavirus) refers to a slowing or diminution in the growth of virus, or viral load, or detectable symptoms associated with infection by that particular virus; or a reduction in the ability of the infected subject to transmit the infection to another, uninfected subject.

The term "inducing an immune response" means eliciting a humoral response (e.g., the production of antibodies) or a cellular response (e.g., the activation of T cells) directed against a virus (e.g., ebolavirus) in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g. 1 to 4 residues) are inserted at any one site within the polypeptide or protein molecule.

The term "lassavirus," "*Lassa virus*," or "LASV" refers to an arenavirus that is any member of the species *Lassa virus*.

The term "marburgvirus" or "*Marburgvirus*" refers to a filovirus that is any member of the genus *Marburgvirus*.

The term "modified vaccinia Ankara," "modified vaccinia ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in (Mayr, A. et al. 1975 Infection 3:6-14; Swiss Patent No. 568,392).

The term "neutralizing antibody" or "NAb" is meant an antibody which either is purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

The term "prevent", "preventing" and "prevention" refers to the inhibition of the development or onset of a condition (e.g., an ebolavirus infection or a condition associated therewith), or the prevention of the recurrence, onset, or development of one or more symptoms of a condition in a subject resulting from the administration of a therapy or the administration of a combination of therapies.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., an ebolavirus infection or a condition or symptom associated therewith or to enhance or improve the prophylactic effect(s) of another therapy.

The term "recombinant" means a polynucleotide of semi-synthetic, or synthetic origin that either does not occur in nature or is linked to another polynucleotide in an arrangement not found in nature.

The term "recombinant," with respect to a viral vector, means a vector (e.g., a viral genome that has been manipulated in vitro, e.g., using recombinant nucleic acid techniques to express heterologous viral nucleic acid sequences.

The term "regulatory sequence" "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., *E. coli*). In the context of MVA vector construction, shuttle vectors are usually DNA plasmids that can be manipulated in *E. coli* and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" is means any mammal, including but not limited to, humans, domestic and farm animals, and zoo, sports, or pet animals, such as dogs, horses, cats, cows, rats, mice, guinea pigs and the like.

The term "Sudan virus" or SUDV refers to a virus belonging to species Sudan ebolavirus.

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval—FDA. Final rule. Fed Regist 57: 58942-58960, 1992.)

The term "surrogate marker for protection" means a surrogate marker that is used in a clinical or animal trial as a substitute for the clinically meaningful endpoint of prevention of ebolavirus or marburgvirus infection.

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "Taï forest virus" or "TAFV" refers to a virus belonging to species nil forest ebolavirus.

The term "therapeutically effective amount" means the amount of the composition (e.g., the recombinant MVA vector or pharmaceutical composition) that, when administered to a mammal for treating an infection, is sufficient to effect such treatment for the infection.

The term "treating" or "treat" refer to the eradication or control of a filovirus, a reduction in the titer of the filovirus, a reduction in the numbers of the filovirus, the reduction or amelioration of the progression, severity, and/or duration of a condition or one or more symptoms caused by the filovirus resulting from the administration of one or more therapies, or the reduction or elimination of the subject's ability to transmit the infection to another, uninfected subject.

The term "vaccine" means material used to provoke an immune response and confer immunity after administration of the material to a subject. Such immunity may include a cellular or humoral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a glycoprotein or matrix protein described here.

The term "viral infection" means an infection by a viral pathogen (e.g., a member of genus *Ebolavirus*) wherein there is clinical evidence of the infection based on symptoms or based on the demonstration of the presence of the viral pathogen in a biological sample from the subject.

The term "virus-like particles" or "VLP" refers to a structure which resembles the native virus antigenically and morphologically.

The term "VP40" refers to the ebolavirus or marburgvirus large matrix protein, or the gene or transcript encoding the ebolavirus or marburgvirus large matrix protein.

II. Filoviruses

The compositions of the present invention are useful for inducing an immune response to a filovirus. The Filoviridae family includes genera *Marburgvirus, Ebolavirus* and *Cuevavirus*. Filoviruses are enveloped, negative strand RNA viruses having a thread-like appearance.

Members of genera *Ebolavirus* and *Marburgvirus* are among the most pathogenic viruses in humans and non-human primates (Feldman and Klenk, 1996, Adv. Virus Res. 47, 1), both causing severe hemorrhagic fever (HF) (Johnson et al., 1997, Lancet 1, no. 8011, P. 569).

Both are zoonotic agents, where human outbreaks initially occur as a result of direct contact with infected wildlife, with subsequent person-to-person transmission through contact with bodily fluids. Although the ecology of these agents remains incompletely understood, several species of African fruit bats may be reservoirs for members of genera *Ebolavirus* and *Marburgvirus*. Filovirus outbreaks are sporadic, sometimes interspersed by years or even decades of no apparent disease activity.

A. *Ebolavirus* Species and Sequences

The term *Ebolavirus* refers to a genus within the family Filoviridae. Like other filoviruses, species within the *Ebolavirus* genus consist of a single strand of negative sense RNA that is approximately 19 kb in length. The RNA contains seven sequentially arranged genes that produce 8 mRNAs upon infection. *Ebolavirus* virions, like virions of other filoviruses, contain seven proteins: (1) a surface glycoprotein (GP), (2) a nucleoprotein (NP), (3-6) four virion structural proteins (VP40, VP35, VP30, and VP24), and an (7) RNA-dependent RNA polymerase (L). The glycoprotein of an ebolavirus is unlike other filoviruses in that it is encoded in two open reading frames. Transcriptional editing is needed to express the transmembrane form that is incorporated into the virion. The unedited form produces a nonstructural secreted glycoprotein (sGP) that is synthesized in large amounts early during the course of infection.

Based on nucleotide sequence and outbreak location, isolates in genus *Ebolavirus* are classified into five antigenically distinct species: *Zaire ebolavirus*, Sudan ebolavirus, nil Forest ebolavirus (also known as Ivory Coast ebolavirus or Cote d'Ivoire ebolavirus (CIEBOV)), Bundibugyo ebolavirus, and Reston ebolavirus. Known viruses belonging to species *Zaire ebolavirus* are commonly referred to as Ebola viruses (EBOV). Known viruses belonging to species Sudan ebolavirus are commonly referred to as Sudan viruses (SUDV). Known viruses belonging to species Taï Forest ebolavirus are commonly referred to as Tai Forest viruses (TAFV). Known viruses belonging to species Bundibugyo ebolavirus are commonly referred to as Bundibugyo viruses (BDBV). Known viruses belonging to species *Marburg marburgvirus* include Marburg virus (MARV) and Ravn virus (RAVV).

Of these, EBOV and SUDV are the most pathogenic, and are the only two that have been associated with recurring outbreaks. Together, EBOV and SUDV account for 94% of EBOV-related deaths.

Infection by a member of genus *Ebolavirus* can lead to Ebola Hemorrhagic Fever (EHF), also known as Ebola Virus Disease (EVD) the clinical manifestations of which are severe. The incubation period varies between 2 to 21 days after exposure to the virus, but the average is 8 to 10 days. The different species in genus *Ebolavirus* are believed to cause somewhat different clinical syndromes. Even within a single species, variation among strains can cause differences in clinical symptoms. However, opportunities for close observation of the diseases under good conditions have been rare.

The initial symptoms of EHF are generally a severe frontal and temporal headache, generalized aches and pains, malaise, and by the second day the victim will often have a fever. The subsequent signs and symptoms indicate multisystem involvement and include systemic (prostration), gastrointestinal (anorexia, nausea, vomiting, abdominal pain, diarrhea), respiratory (chest pain, shortness of breath, cough, nasal discharge), vascular (conjunctival injection, postural hypotension, oedema) and neurological (headache, confusion, coma) manifestations. Hemorrhagic manifestations arise during the peak of the illness and include petechiae, ecchymoses, uncontrolled oozing from venipuncture sites, mucosal hemorrhages, and post-mortem evidence of visceral hemorrhagic effusions. A macropapular rash associated with varying severity of erythema and desquamate can often be noted by day 5-7 of the illness; this symptom is a valuable differential diagnostic feature and is usually followed by desquamation in survivors. Abdominal pain is sometimes associated with hyperamylasaemia and true pancreatitis. In later stages, shock, convulsions, severe metabolic disturbances, and, in more than half the cases, diffuse coagulopathy supervene. See Sanchez A, Geisbert T W, Feldmann H. Filoviridae: Marburg and Ebola viruses. In: Knipe D M, Howley P M, eds. Fields virology. Philadelphia: Lippincott Williams & Wilkins, 2006: 1409-1448; Pattyn S R. Ebola virus haemorrhagic fever. Amsterdam: Elsevier, North-Holland, 1978; Peters C J, LeDuc L W. Ebola: the virus and the disease. J Infect Dis 1999; 179 (suppl 1): S1-S288; Feldmann H, Geisbert T, Kawaoka Y. Filoviruses: recent advances and future challenges. J Infect Dis 2007; 196 (suppl 2): S129-S443.

Patients with fatal disease develop clinical signs early during infection and typically die between day 6 and 16 as a result of hypovolaemic shock and multiorgan failure. Hemorrhages can be severe but are only present in fewer than half of patients. In non-fatal cases, patients typically have a fever for several days and improve around day 6-11, about the time that the humoral antibody response is noted. Patients with non-fatal or asymptomatic disease mount specific IgM and IgG responses that seem to be associated with a temporary early and strong inflammatory response, including interleukin β, interleukin 6, and tumour necrosis factor α (TNFα).

While case fatality rates vary between outbreaks and among the *Ebolavirus* species, *Zaire ebolavirus* has been associated with up to 90% mortality, while Sudan ebolavirus has been associated with up to 60% mortality.

Using current methodology, ebolavirus is detectable in blood only after onset of symptoms, which accompany the rise in circulating virus. It may take up to three days after symptoms start for the virus to reach detectable levels. Laboratory tests used in diagnosis include, for example, antigen-capture enzyme-linked immunosorbent assay (ELISA) testing, IgM ELISA, polymerase chain reaction (PCR), virus isolation, and later in the course of infection or recovery-detection of IgM and IgG antibodies.

No vaccine or therapeutic has been approved by the FDA for ebolavirus, for either prophylactic or therapeutic use. Present treatment strategies are primarily symptomatic and supportive. In developing countries, these strategies typically include isolation, malaria treatment, broad spectrum antibiotics, and antipyretics before diagnosis. Fluid substitution, preferentially intravenous administration, and analgesics may also be provided. In developed countries with facilities having appropriate isolation units, intensive care treatment is provided and directed towards maintenance of effective blood volume and electrolyte balance. Shock, cerebral edema, renal failure, coagulation disorders, and secondary bacterial infection must also be managed. Organ failure is also addressed, e.g., by dialysis for kidney failure and extracorporeal membrane oxygenation for lung failure.

B. Marburg Virus Species and Sequences

Marburgviruses are substantially identical structurally to ebolaviruses. The marburgvirus genome consists of a single strand of negative sense RNA that is approximately 19.1 kb in length and which encodes a series of polypeptides that correspond in sequence and function to those of ebolaviruses, although the exact intergenic regions are different between the two genera. Thus, a marburgvirus consists of seven polypeptides, which are (as in ebolaviruses) the envelope glycoprotein (GP), the nucleoprotein (NP), matrix proteins VP24 and VP40, the transcription factor VP30, the polymerase cofactor VP35, and the viral polymerase.

Only one species of marburgvirus has been reported, *Marburg marburgvirus* (formerly Lake Victoria marburgvirus), and two individual viruses, Marburg virus (MARV) and Ravn virus (RAVN), within this species.

Marburg hemorrhagic fever (MHF) may affects both humans and non-human primates. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea may then appear. Symptoms become increasingly severe and may include jaundice, inflammation of the pancreas, severe weight loss, delirium, shock, liver failure, massive hemorrhaging, and multi-organ dysfunction.

There is no vaccine for marburgvirus approved by the FDA, either prophylactic or therapeutic. As with EHF, current treatment generally currently consists of supportive therapy, including maintenance of blood volume and electrolyte balance, as well as analgesics and standard nursing care.

C. Lassa Virus Species and Sequences

*Lassa virus* is an arenavirus belonging to genus *Arenavirus*, family Arenaviridae. The arenavirus genome consists of two single-stranded negative-sense RNAs, one approximately 7.2 kb in length and the other approximately 3.5 kb in length. Each of the RNAs encodes two proteins. The gene sequences for the proteins are oriented in opposite directions; this arrangement is referred to as an ambisense coding strategy. The large (7.2 kb) genomic RNA encodes the RNA-dependent RNA polymerase (L) protein and the matrix (Z) protein. The small (3.5 kb) genomic RNA encodes the nucleoprotein (NP) and the glycoprotein precursor (GP). On each genomic RNA, the two genes are separated by an intergenic region (IGR) The ambisense coding strategy results in different mechanisms of transcription for the four proteins. The NP and L mRNAs are transcribed directly from the genomic RNA. The GP and Z mRNAs, on the other hand, are translated from anti-genomic RNAs. The IGR is believed to serve as a signal for termination of transcription. (Shao et al. (2015), Pathogens 4: 283-306).

Lassa fever is the acute hemorrhagic fever caused by *Lassa virus*. Symptoms typically appear 6-21 days after infection. Approximately 80% of cases are mild, involving mild fever, general malaise, weakness, and headache. In approximately 20% of cases, Lassa fever causes more severe symptoms including high fever, sore throat, mucosal bleeding, respiratory distress, vomiting, swelling, severe pain, and shock. Certain neurological problems may also occur. Of patients hospitalized for Lassa fever, approximately 15%-20% die from the infection (Kyei et al. (2015), BMC Infectious Diseases 15:217). Unlike filoviruses, which cause sporadic outbreaks, *Lassa virus* is a common human pathogen that causes endemic disease in a large area of West Africa (Andersen et al. (2015), Cell 162:738-750). Official estimates indicate 300,000-500,000 cases of Lassa fever each year with approximately 5,000-10,000 deaths; however, other measures indicate that the disease may be much more serious, accounting for as many as 3 million cases and 67,000 deaths annually (Leski et al. (2015) Emerging Infectious Diseases 21(4):609-618). Several experimental vaccines against LASV have been tested in animal models. To date, however, no Lassa fever vaccine has yet been approved for sale (Falzarano and Feldmann (2015), Current Opinion in Virology 3:343-351). Other than supportive care, there are few options for treatment of *Lassa virus* infection. Only the broad-spectrum antiviral drug ribavirin has shown efficacy, and it must be used early in the course of the disease in order to be effective (Olschlager and Flatz (2013), PLoS Pathogens 9(4):e1003212).

III. Recombinant Viral Vectors

In one aspect, the present invention is a recombinant viral vector comprising one or more genes of a hemorrhagic fever virus, such as an *Ebolavirus*, a *Marburgvirus*, or an *Arenavirus*. In certain embodiments, the recombinant viral vector is a vaccinia viral vector, and more particularly, an MVA vector, comprising one or more genes of a hemorrhagic fever virus, such as an *Ebolavirus*, a *Marburgvirus*, or an *Arenavirus*.

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

Several such strains of vaccinia virus have been developed to avoid undesired side effects of smallpox vaccination. Thus, a modified vaccinia Ankara (MVA) has been generated by long-term serial passages of the Ankara strain of vaccinia virus (CVA) on chicken embryo fibroblasts (for review see Mayr, A. et al. 1975 Infection 3:6-14; Swiss Patent No. 568,392). The MVA virus is publicly available from American Type Culture Collection as ATCC No.: VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine. MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 PNAS USA 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

Recombinant MVA vaccinia viruses can be prepared as set out hereinafter. A DNA-construct which contains a DNA-sequence which codes for a foreign polypeptide flanked by MVA DNA sequences adjacent to a predetermined insertion site (e.g. between two conserved essential MVA genes such as I8R/G1L; in restructured and modified deletion III; or at other non-essential sites within the MVA genome) is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. Such methods of making recombinant MVA vectors are described in PCT publication WO/2006/026667 incorporated by reference herein. The DNA-construct contains sequences flanking the left and the right side of a naturally occurring deletion. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffner 1980 PNAS USA 77:2163-2167) or by other methods known to those skilled in the art.

The MVA vectors described and tested herein were unexpectedly found to be effective after a single prime or a homologous prime/boost regimen. Other MVA vector designs require a heterologous prime/boost regimen while still other published studies have been unable to induce effective immune responses with MVA vectors. Conversely, the present MVA vector design and methods of manufacture are useful in producing effective MVA vaccine vectors for eliciting effective T-cell and antibody immune responses. Furthermore, the utility of an MVA vaccine vector capable of eliciting effective immune responses and antibody production after a single homologous prime boost is significant for considerations such as use, commercialization and transport of materials especially to affected third world locations.

In one embodiment, the present invention is a recombinant viral vector (e.g., an MVA vector) comprising one or more heterologous gene inserts of a filovirus (e.g., an ebolavirus or marburgvirus). The viral vector (e.g., an MVA vector) may be constructed using conventional techniques known to one of skill in the art. The one or more heterologous gene inserts encode a polypeptide having desired immunogenicity, i.e., a polypeptide that can induce an immune reaction, cellular immunity and/or humoral immunity, in vivo by administration thereof. The gene region of the viral vector (e.g., an MVA vector) where the gene encoding a polypeptide having immunogenicity is introduced is flanked by regions that are indispensable. In the introduction of a gene encoding a polypeptide having immunogenicity, an appropriate promoter may be operatively linked upstream of the gene encoding a polypeptide having desired immunogenicity.

The one or more genes may be selected from any species of hemorrhagic fever virus. In one embodiment, the one more genes are selected from an *Ebolavirus*, *Marburgvirus* or *Arenavirus* species, and more particularly, a hemorrhagic fever virus selected from the group consisting of EBOV, SUDV, TAFV, BDBV, RESTV, MARV, and LASV, or a combination thereof. In exemplary embodiments, the gene encodes a polypeptide or protein capable of inducing an immune response in the subject to which it is administered, and more particularly, an immune response capable of providing a protective and/or therapeutic benefit to the subject. In one embodiment, the one or more genes encode the virus glycoprotein (GP), the secreted GP (sGP), the major nucleoprotein (NP), RNA-dependent RNA polymerase (L), or one or more virion structural proteins (e.g., Z, VP40, VP35, VP30, or VP24)). The heterologous gene inserts are inserted into one or more deletion sites of the vector under the control of promoters compatible with poxvirus expression systems.

In one embodiment, the deletion III site is restructured and modified to remove non-essential flanking sequences.

In exemplary embodiments, the vaccine is constructed to express an ebolavirus GP for example EBOV GP, which is inserted between two conserved essential MVA genes (I8R and G1L) using shuttle vector pGeo-GP; and to express EBOV VP40, which is inserted into deletion III using shuttle vector pGeo-VP40. pGeo-GP and pGeo-VP40 are constructed with an ampicillin resistance marker, allowing the vector to replicate in bacteria; with two flanking sequences, allowing the vector to recombine with a specific location in the MVA genome; with a green fluorescent protein (GFP)

selection marker, allowing the selection of recombinant MVAs; with a sequence homologous to part of Flank 1 of the MVA sequence, enabling removal of the GFP sequence from the MVA vector after insertion of VP40 into the MVA genome; with a modified H5 (mH5) promoter, which enables transcription of the inserted heterologous gene insert; and with a filovirus gene. pGeo-GP and pGeo-VP40 differ in that pGeo-GP contains the GP sequence, whereas pGeo-VP40 contains the VP40 sequence; and in that pGeo-GP recombines with sequences of MVA I8R and G1L (two essential genes) and pGeo-VP40 recombines with regions flanking the restructured and modified Deletion III of MVA.

In exemplary embodiments, the present invention provides a recombinant MVA vector comprising a gene encoding the glycoprotein (GP) gene and a gene encoding VP40, in each case, from an ebolavirus, marburgvirus, or Lassa virus.

In certain embodiments, the polypeptide, or the nucleic acid sequence encoding the polypeptide, may have a mutation or deletion (e.g., an internal deletion, truncation of the amino- or carboxy-terminus, or a point mutation).

The one or more genes introduced into the recombinant viral vector are under the control of regulatory sequences that direct its expression in a cell.

The nucleic acid material of the viral vector may be encapsulated, e.g., in a lipid membrane or by structural proteins (e.g., capsid proteins), that may include one or more viral polypeptides.

In exemplary embodiments, the present invention is a recombinant viral vector (e.g., a recombinant MVA vector) comprising one or more genes, or one or more polypeptides encoded by the gene or genes, from an ebolavirus, marburgvirus, or Lassa virus. The ebolavirus, marburgvirus, or Lassa virus gene may encode a polypeptide or protein capable of inducing an immune response in the subject to which it is administered, and more particularly, an immune response capable of providing a protective and/or therapeutic benefit to the subject, e.g., the ebolavirus, marburgvirus, or Lassa virus glycoprotein. As used herein, the term "ebolavirus, marburgvirus, or Lassa virus glycoprotein" refers to the glycoprotein polypeptide encoded by the ebolavirus, marburgvirus, or Lassa virus genome, whether in secreted or transmembrane bound form, or any fragment or mutation of the glycoprotein polypeptide, that is encoded by the ebolavirus, marburgvirus, or Lassa virus genome so long as it has the ability to induce or enhance an immune response or confer a protective or therapeutic benefit to the subject, e.g., against one or more of SUDV, EBOV, TAFV, BDBV, MARV, or LASV. The nucleic acid sequences of ebolavirus, marburgvirus, or Lassa virus glycoproteins are published and are available from a variety of sources, including, e.g., GenBank and PubMed. Exemplary GenBank references including ebolavirus, marburgvirus, or Lassa virus glycoprotein sequences include those corresponding to accession numbers KM233103 (EBOV, 2014 strain), KC242798 (EBOV, central sequence), KC545390 (SUDV), KC545396 (BDBV), NC 001608 (MARV), and JN650517 (LASV GP and NP) and JN650518 (LASV Z).

In certain embodiments, the one or more genes encodes a polypeptide, or fragment thereof, that is substantially identical (e.g., at least 60%, 65%, 70%, 75%, 80%, 85%, 90%, 95%, 98%, 99%, or even 100% identical) to the selected ebolavirus, marburgvirus, or Lassa virus glycoprotein over at least 20, 25, 30, 35, 40, 45, 50, 55, 60, 65, or 70 contiguous residues of the selected ebolavirus, marburgvirus, or Lassa virus glycoprotein that retain immunogenic activity.

In exemplary embodiments, the recombinant viral vector may also include an ebolavirus, marburgvirus, or Lassa virus glycoprotein present on its surface. The ebolavirus, marburgvirus, or Lassa virus glycoprotein may be obtained by any suitable means, including, e.g., application of genetic engineering techniques to a viral source, chemical synthesis techniques, recombinant production, or any combination thereof.

In another embodiments, the present invention is a recombinant MVA vector comprising at least one heterologous gene insert from an ebolavirus, marburgvirus, or Lassa virus, wherein the gene is selected from the group encoding the glycoprotein (GP), the secreted GP (sGP), the major nucleoprotein (NP), RNA-dependent RNA polymerase (L), or one or more other viral proteins (e.g., Z, VP40, VP35, VP30, or VP24)).

In a particular embodiment, the present invention is a recombinant MVA vector comprising a gene encoding GP and a gene encoding VP40. In another embodiment, the present invention is a recombinant MVA vector comprising genes encoding GP, Z, and NP. The heterologous gene inserts are inserted into one or more deletion sites of the MVA vector under the control of promoters compatible with poxvirus expression systems.

In one embodiment, the GP is inserted into deletion site I, II, III, IV, V or VI of the MVA vector, and the VP40 is inserted into deletion site I, II, III, IV, V or VI of the MVA vector.

In one embodiment, the GP is inserted between I8R and G1L of the MVA vector, or into restructured and modified deletion III of the MVA vector; and the VP40 is inserted between I8R and GIL of the MVA vector, or into restructured and modified deletion site III of the MVA vector.

In one embodiment relating to LASV, the GP is inserted into deletion site I, II, III, IV, V or VI of the MVA vector, and the Z is inserted into deletion site I, II, III, IV, V or VI of the MVA vector.

In one embodiment, the recombinant vector comprises in a first deletion site, a gene encoding GP operably linked to a promoter compatible with poxvirus expression systems, and in a second deletion site, genes encoding Z and NP in reverse orientation each operably linked to a promoter compatible with poxvirus expression systems.

In one embodiment relating to LASV, the GP is inserted between I8R and GIL of the MVA vector, or into restructured and modified deletion III of the MVA vector; and the Z is inserted between I8R and G1L of the MVA vector, or into restructured and modified deletion site III of the MVA vector.

In another embodiment relating to LASV, the GP and Z are inserted into different deletion sites. For example, the GP sequence is inserted between two essential and highly conserved MVA genes, I8R/G1L, to limit the formation of viable deletion mutants; and, the Z sequence is inserted into a restructured and modified deletion III site.

In exemplary embodiments, the present invention is a recombinant MVA vector comprising at least one heterologous gene insert (e.g., one or more gene inserts) from an ebolavirus or a marburgvirus which is under the control of regulatory sequences that direct its expression in a cell. The gene may be, for example, under the control of a promoter selected from the group consisting of Pm2H5, Psyn II, or mH5 promoters.

The recombinant viral vector of the present invention can be used to infect cells of a subject, which, in turn, promotes the translation into a protein product of the one or more viral genes of the viral vector (e.g., an ebolavirus, marburgvirus, or *Lassa virus* glycoprotein). As discussed further herein, the recombinant viral vector can be administered to a subject so that it infects one or more cells of the subject, which then promotes expression of the one or more viral genes of the viral vector and stimulates an immune response that is protective against infection by an ebolavirus, marburgvirus, or *Lassa virus* (e.g., EBOV) or that reduces or prevents infection by an ebolavirus, marburgvirus, or *Lassa virus* (e.g., EBOV).

In one embodiment, the recombinant MVA vaccine expresses proteins that assemble into virus-like particles (VLPs) comprising the GP (glycoprotein), and VP40 (matrix protein). While not wanting to be bound by any particular theory, it is believed that the GP is provided to elicit a protective immune response and the VP40 (matrix protein) is provided to enable assembly of VLPs and as a target for T cell immune responses, thereby enhancing the protective immune response and providing cross-protection.

Similarly relating to LASV, in one embodiment, the recombinant MVA vaccine expresses proteins that assemble into virus-like particles (VLPs) comprising the GP (glycoprotein), and Z (matrix protein). While not wanting to be bound by any particular theory, it is believed that the GP is provided to elicit a protective immune response and the Z (matrix protein) is provided to enable assembly of VLPs and as a target for T cell immune responses, thereby enhancing the protective immune response and providing cross-protection.

For references, see Stahelin, *Front in Microbiol* 5:300 (2014); Marzi et al., *J Infect Dis* 204 Suppl 3:S1066 (2011); Warfield and Aman, *J Infect Dis* 204 Suppl 3:S1053 (2011); and Mire et al., *PLoS Negl Trop Dis* 7:e2600 (2013).

One or more genes may be optimized for use in an MVA vector. Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the gene. In exemplary embodiments, the number of homopolymer stretches in the GP or VP40 sequence will be reduced to stabilize the construct. A silent mutation may be provided for anything similar to a vaccinia termination signal. An extra nucleotide may be added in order to express the transmembrane, rather than the secreted, form of ebolavirus GP.

In exemplary embodiments, the GP and VP40 sequences are codon optimized for expression in MVA using a computer algorithm; GP and VP40 sequences with runs of ≥5 deoxyguanosines, ≥5 deoxycytidines, ≥5 deoxyadenosines, and ≥5 deoxythymidines are interrupted by silent mutation to minimize loss of expression due to frame shift mutations; and the GP sequence is modified through addition of an extra nucleotide to express the transmembrane, rather than the secreted, form of ebolavirus GP.

In one embodiment, the present invention provides a vaccine vector composition that is monovalent. As used herein the term monovalent refers to a vaccine vector composition that contains GP and matrix sequences from one species of ebolavirus, Marbugvirus, or *Arenavirus*.

In another embodiment, the present invention provides a vaccine that is bivalent. As used herein the term monovalent refers to a vaccine vector composition that contains two vectors having GP and matrix sequences from different species of ebolavirus, Marbugvirus, or *Arenavirus*.

In another embodiment, the present invention provides a vaccine that is trivalent. As used herein the term trivalent refers to a vaccine vector composition that contains three vectors having GP and matrix sequences from different species of ebolavirus, Marbugvirus, or *Arenavirus*.

In another embodiment, the present invention provides a vaccine that is quadrivalent. As used herein the term quadrivalent refers to a vaccine vector composition that contains four vectors having GP and matrix sequences from different species of ebolavirus, Marbugvirus, or *Arenavirus*. As used herein, the terms tetravalent and quadrivalent are synonymous.

In one embodiment, the recombinant viral vector (e.g., an MVA vector) comprises two heterologous gene inserts from an *Ebolavirus* species, a Marbugvirus species, or an *Arenavirus* species, wherein the first heterologous gene insert and the second heterologous gene insert are from the same species of *Ebolavirus*, Marbugvirus, or *Arenavirus* species.

In another embodiment, the recombinant viral vector (e.g., an MVA vector) comprises two heterologous gene inserts from an *Ebolavirus* species, a Marbugvirus species, or an *Arenavirus* species, wherein the first heterologous gene insert is from an *Ebolavirus*, Marbugvirus, or *Arenavirus* species different than the second heterologous gene insert. In one embodiment, the first heterologous gene insert is from the EBOV virus and the second heterologous gene insert is from an ebolavirus or a marburgvirus selected from SUDV, TAFV, BDBV, RESTV, MARV, or LASV.

In exemplary embodiments, the recombinant viral vector (e.g., an MVA vector) comprises three heterologous gene inserts from an *Ebolavirus* species, or a Marbugvirus species, or an *Arenavirus* species, wherein the first heterologous gene insert is from an *Ebolavirus* species, a Marbugvirus species, or an *Arenavirus* species different at least from one of the second or third heterologous gene inserts. In one embodiment, the first heterologous gene insert is from the EBOV virus and the second and third heterologous gene inserts are selected from an ebolavirus or a marburgvirus selected from SUDV, TAFV, BDBV, RESTV, MARV, or LASV. The second and third heterologous gene inserts may be the same or different.

The recombinant viral vectors of the present invention may be used alone, or in combination. In one embodiment, two different recombinant viral vectors are used in combination, where the difference may refer to the one or more heterologous gene inserts or the other components of the recombinant viral vector or both. In exemplary embodiments, two or more recombinant viral vectors are used in combination in order to protect against infection by all versions of ebolavirus, marburgvirus, and *Lassa virus* known to be lethal in humans.

The present invention also extends to host cells comprising the recombinant viral vector described above, as well as isolated virions prepared from host cells infected with the recombinant viral vector.

IV. Pharmaceutical Composition

The recombinant viral vectors of the present invention are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect and/or treat a hemorrhagic fever virus (e.g., an ebolavirus) comprising a recombinant MVA vector that expresses at least one hemorrhagic fever virus polypeptide (e.g., a GP) or an immunogenic fragment thereof. The vaccine composition may comprise one or more additional therapeutic agents.

The pharmaceutical composition may comprise 1, 2, 3, 4 or more than 4 different recombinant MVA vectors.

In one embodiment, the present invention provides a vaccine vector composition that is monovalent. As used herein the term monovalent refers to a vaccine vector composition that contains GP and matrix sequences from one species of ebolavirus, Marbugvirus, or *Arenavirus*.

In another embodiment, the present invention provides a vaccine that is bivalent. As used herein the term monovalent refers to a vaccine vector composition that contains two vectors having GP and matrix sequences from different species of ebolavirus, Marbugvirus, or *Arenavirus*.

In another embodiment, the present invention provides a vaccine that is trivalent. As used herein the term trivalent refers to a vaccine vector composition that contains three vectors having GP and matrix sequences from different species of ebolavirus, Marbugvirus, or *Arenavirus*.

In another embodiment, the present invention provides a vaccine that is quadrivalent. As used herein the term monovalent refers to a vaccine vector composition that contains four vectors having GP and matrix sequences from different species of ebolavirus, Marbugvirus, or *Arenavirus*. As used herein, the terms tetravalent and quadrivalent are synonymous.

As used herein, the phrase "pharmaceutically acceptable carrier" encompasses any of the standard pharmaceutical carriers, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. One exemplary pharmaceutically acceptable carrier is physiological saline.

Other physiologically acceptable diluents, excipients, carriers, or adjuvants and their formulations are known to those skilled in the art.

The compositions utilized in the methods described herein can be administered by a route selected from, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, Remington: The *Science* and Practice of Pharmacy (21.sup.st ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastrointestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

Pharmaceutical compositions comprising any of the nucleic acid molecules encoding Ebola viral proteins of the present invention are useful to immunize a subject against disease caused by ebolavirus infection. Thus, this invention further provides methods of immunizing a subject against disease caused by ebolavirus infection, e.g., hemorrhagic fever, comprising administering to the subject an immunoeffective amount of a pharmaceutical composition of the invention. This subject may be an animal, for example a mammal, such as a primate or preferably a human.

The vaccines of the present invention are also suitable for veterinary immunization. The vaccines of the present invention comprising nucleic acid molecules encoding ebolavirus structural gene products from the Reston ebolavirus species, which is known to infect animals, are particularly useful in such veterinary immunization methods.

The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

Kits

This invention also provides kits comprising the vaccines of the present invention. For example, kits comprising a vaccine and instructions for use are within the scope of this invention.

V. Method of Use

The compositions of the invention can be used as vaccines for inducing an immune response to a filovirus or an arenavirus, such as a member of the genus *Ebolavirus*, the genus *Marburgvirus*, or the genus *Arenavirus*, including any species thereof.

In exemplary embodiments, the present invention provides a method of preventing a filovirus or arenavirus (e.g., ebolavirus) infection to a subject in need thereof (e.g., an unexposed) subject, said method comprising administering the composition of the present invention to the subject in a prophylactically effective amount. The result of the method is that the subject is partially or completely immunized against the virus.

In exemplary embodiments, the present invention provides a method of treating a filovirus or arenavirus (e.g., ebolavirus) infection in a subject in need thereof (e.g., an exposed subject, such as a subject who has been recently exposed but is not yet symptomatic, or a subject who has been recently exposed and is only mildly symptomatic), said method comprising administering the composition of the present invention to the subject in a therapeutically effective amount. The result of treatment is a subject that has an improved therapeutic profile.

In certain embodiments, the compositions of the invention can be used as vaccines for treating a subject infected with more than one filovirus or more than one areavirus, e.g., multiple species of *Ebolavirus* or *Arenavirus*. The recombinant viral vector comprises genes or sequences encoding viral proteins of multiple species of *Ebolavirus* or *Arenavirus* and/or the pharmaceutical composition comprises more than one type of recombinant viral vector, in terms of the heterologous gene inserts or sequences contained.

Typically the vaccines will be in an admixture and administered simultaneously, but may also be administered separately.

A subject to be treated according to the methods described herein (e.g., a subject infected with, an ebolavirus) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been identified using standard tests or may have been identified, without examination, as one at high risk due to the presence of one or more risk factors (e.g., exposure to ebolavirus, etc.).

Prophylactic treatment may be administered, for example, to a subject not yet exposed to or infected by a hemorrhagic fever virus but who is susceptible to, or otherwise at risk of exposure or infection with an a hemorrhagic fever virus.

Therapeutic treatment may be administered, for example, to a subject already exposed to or infected by a hemorrhagic fever virus who is not yet ill, or showing symptoms or infection, suffering from a disorder in order to improve or stabilize the subject's condition (e.g., a patient already infected with an a hemorrhagic fever virus). The result is an improved therapeutic profile. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of viral replication, a decrease in viral titers or viral load, eradication or clearing of the virus.

In other embodiments, treatment may result in amelioration of one or more symptoms of the infection, including any symptom identified above. According to this embodiment, confirmation of treatment can be assessed by detecting an improvement in or the absence of symptoms.

In other embodiments, treatment may result in reduction or elimination of the ability of the subject to transmit the infection to another, uninfected subject. Confirmation of treatment according to this embodiment is generally assessed using the same methods used to determine amelioration of the disorder, but the reduction in viral titer or viral load necessary to prevent transmission may differ from the reduction in viral titer or viral load necessary to ameliorate the disorder.

In one embodiment, the present invention is a method of inducing an immune response in a subject (e.g., a human) by administering to the subject a recombinant viral vector that encodes at least one gene from a hemorrhagic fever virus, such as a member of genus *Ebolavirus* a member of genus *Marburgvirus*, or a member of genus *Arenavirus*. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Ebolavirus*, more particularly, EBOV. In certain embodiments, the recombinant viral vector encodes at least two genes from an ebolavirus, more particularly, EBOV. The immune response may be a cellular immune response or a humoral immune response, or a combination thereof.

In another particular embodiment, the present invention is a method of inducing an immune response in a subject (e.g., a human) by administering to the subject a recombinant viral vector that encodes at that encodes at least one gene from a member of genus *Marburgvirus*, more particularly, MARV. In certain embodiments, the recombinant viral vector encodes at least two genes from a marburgvirus, more particularly, MARV. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Ebolavirus*, more particularly, SUDV. In certain embodiments, the recombinant viral vector encodes at least two genes from an ebolavirus, more particularly, SUDV. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Ebolavirus*, more particularly, BDBV. In certain embodiments, the recombinant viral vector encodes at least two genes from an ebolavirus, more particularly, BDBV. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from a member of genus *Arenavirus*, more particularly, LASV. In certain embodiments, the recombinant viral vector encodes at least two genes from an arenavirus, more particularly, LASV. The immune response may be a cellular immune response or a humoral immune response, or a combination thereof.

In another embodiment, the invention features a method of treating a filovirus infection (e.g., an ebolavirus infection) in a subject (e.g., a human) in need thereof by administering to the subject a recombinant viral vector that encodes at least one gene from the *Zaire ebolavirus* species of ebolavirus (e.g., the EBOV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating a filovirus infection (e.g., an ebolavirus infection) in a subject (e.g., a human) by administering to the subject a recombinant viral vector that encodes at least one gene from the Sudan ebolavirus species of ebolavirus (e.g., the SUDV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating a filovirus infection (e.g., an ebolavirus infection) in a subject (e.g., a human) by administering to the subject a recombinant viral vector that encodes at least one gene from the Bundibugyo ebolavirus species of ebolavirus (e.g., the BDBV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating a filovirus infection (e.g., a marburgvirus infection) in a subject (e.g., a human) by administering to the subject a recombinant viral vector that encodes at least one gene from the *Marburg marburgvirus* species of marburgvirus (e.g., the MARV glycoprotein). The subject being treated may not have, but is at risk of developing, an infection by a filovirus, for example, an infection caused by a filovirus selected from TAFV, EBOV, SUDV, BDBV, MARV or a combination thereof.

In another embodiment, the invention features a method of treating an arenavirus infection (e.g., a *Lassa virus* infection) in a subject (e.g., a human) by administering to the subject a recombinant viral vector that encodes at least one gene from the *Lassa virus* species of arenavirus (e.g., the LASV glycoprotein). The subject being treated may not have, but is at risk of developing, an infection by an arenavirus, for example, an infection caused by LASV.

In another embodiment, the subject may already be infected with at least one filovirus or arenavirus (e.g., an ebolavirus or a *Lassa virus*). The infection may be caused by a hemorrhagic fever virus selected from the group consisting of TAFV, EBOV, SUDV, BDBV, MARV, LASV, or a combination thereof.

The composition may be administered, e.g., by injection (e.g., intramuscular, intraarterial, intravascular, intravenous, intraperitoneal, or subcutaneous).

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

While not to be bound by any specific mechanism, it is believed that upon inoculation with a pharmaceutical composition as described herein, the immune system of the host responds to the vaccine by producing antibodies, both secretory and serum, specific for ebolavirus, marburgvirus, or *Lassa virus* proteins; and by producing a cell-mediated immune response specific for ebolavirus, marburgvirus, or *Lassa virus*. As a result of the vaccination, the host becomes at least partially or completely immune to ebolavirus, marburgvirus, or *Lassa virus* infection, or resistant to developing moderate or severe disease caused by ebolavirus, marburgvirus, or *Lassa virus* infection.

In one aspect, methods are provided to alleviate, reduce the severity of, or reduce the occurrence of, one or more of the symptoms (e.g., fever, hemorrhagic fever, severe headache, muscle pain, malaise, extreme asthenia, conjunctivitis, popular rash, dysphagia, nausea, vomiting, bloody diarrhea followed by diffuse hemorrhages, delirium, shock, jaundice, thrombocytopenia, lymphocytopenia, neutrophilia, focal necrosis in various organs (e.g., kidneys and liver), and acute respiratory distress) associated with ebolavirus, marburgvirus, or *Lassa virus* infection comprising administering an effective amount of a pharmaceutical composition comprising a recombinant MVA viral vector that comprises GP and VP40 sequences from the *Zaire ebolavirus*, Sudan ebolavirus, Taï Forest ebolavirus, Bundibugyo ebolavirus, Reston ebolavirus, or *Marburg marburgvirus* species of filovirus; or comprising GP and Z sequences from the *Lassa virus* species of arenavirus; or comprising GP, Z, and NP sequences from the *Lassa virus* species of arenavirus.

In one embodiment, the MVA viral vector comprises GP and VP40 sequences from a *Zaire ebolavirus* species.

In one embodiment, the MVA viral vector comprises GP and VP40 sequences from a Sudan ebolavirus species.

In one embodiment, the MVA viral vector comprises GP and VP40 sequences from aBundibugyo ebolavirus species.

In one embodiment, the MVA viral vector comprises GP and VP40 sequences from a *Marburg marburgvirus* species. In one embodiment, the MVA viral vector comprises GP and Z sequences from a *Lassa virus* species.

In one embodiment, the MVA viral vector comprises GP, Z, and NP sequences from a *Lassa virus* species.

In another embodiment, a combination of at least two different recombinant MVA viral vectors are administered wherein the GP and VP40 sequences are from a *Zaire ebolavirus*, Sudan ebolavirus, Taï Forest ebolavirus, Bundibugyo ebolavirus, Reston ebolavirus, or *Marburg marburgvirus* species of filovirus. Also included in this embodiment are combinations of one recombinant MVA viral vector encoding GP and VP40 from a filovirus with another recombinant MVA viral vector encoding GP and Z or GP, Z, and NP from the *Lassa virus* species of arenavirus.

In one embodiment, the pharmaceutical composition comprises two recombinant MVA vaccines expressing GP and VP40 sequences from a *Zaire ebolavirus* and a Bundibugyo ebolavirus species of ebolavirus.

In one embodiment, the pharmaceutical composition comprises two recombinant MVA vaccines expressing GP and VP40 sequences from a *Zaire ebolavirus* and a Sudan ebolavirus.

In one embodiment, the pharmaceutical composition comprises two recombinant MVA vaccines expressing GP and VP40 sequences from a Sudan ebolavirus and a Bundibugyo ebolavirus.

In one embodiment, the pharmaceutical composition comprises two recombinant MVA vaccines expressing GP and VP40 sequences from a *Zaire ebolavirus* and a *Marburg marburgvirus*.

In one embodiment, the pharmaceutical composition comprises two recombinant MVA vaccines expressing GP and VP40 sequences from a Bundibugyo ebolavirus species and a *Marburg marburgvirus*.

In one embodiment, the pharmaceutical composition comprises two recombinant MVA vaccines expressing GP and VP40 sequences from a Sudan ebolavirus and a *Marburg marburgvirus*

In one embodiment, the pharmaceutical composition comprises two recombinant MVA vaccines, one expressing GP and VP40 sequences from a *Zaire ebolavirus* and the other expressing GP and Z sequences from a *Lassa virus*.

In one embodiment, the pharmaceutical composition comprises two recombinant MVA vaccines, one expressing GP and VP40 sequences from a Sudan ebolavirus and the other expressing GP and Z sequences from a *Lassa virus*.

In one embodiment, the pharmaceutical composition comprises two recombinant MVA vaccines, one expressing GP and VP40 sequences from a Bundibugyo ebolavirus and the other expressing GP and Z sequences from a *Lassa virus*.

In one embodiment, the pharmaceutical composition comprises two recombinant MVA vaccines, one expressing GP and VP40 sequences from a *Marburg marburgvirus* and the other expressing GP and Z sequences from a *Lassa virus*.

In one embodiment, the pharmaceutical composition comprises two recombinant MVA vaccines, one expressing GP and VP40 sequences from a *Zaire ebolavirus* and the other expressing GP, Z, and NP sequences from a *Lassa virus*.

In one embodiment, the pharmaceutical composition comprises two recombinant MVA vaccines, one expressing GP and VP40 sequences from a Sudan ebolavirus and the other expressing GP, Z, and NP sequences from a *Lassa virus*.

In one embodiment, the pharmaceutical composition comprises two recombinant MVA vaccines, one expressing GP and VP40 sequences from a Bundibugyo ebolavirus and the other expressing GP, Z, and NP sequences from a *Lassa virus*.

In one embodiment, the pharmaceutical composition comprises two recombinant MVA vaccines, one expressing GP and VP40 sequences from a *Marburg marburgvirus* and the other expressing GP, Z, and NP sequences from a *Lassa virus*.

In another embodiment, a combination of three or more different recombinant MVA viral vectors are administered wherein the GP and VP40 sequences are from a *Zaire ebolavirus*, a Sudan ebolavirus, a Taï Forest ebolavirus, a Bundibugyo ebolavirus, a Reston ebolavirus, or a *Marburg marburgvirus* species of Filovirus. Also included in this embodiment are combinations of two or more recombinant MVA viral vectors encoding GP and VP40 from filoviruses with another recombinant MVA viral vector encoding GP and Z or GP, Z, and NP from the *Lassa virus* species of arenavirus.

In one embodiment, the pharmaceutical composition comprises three recombinant MVA vaccines expressing glycoprotein and matrix protein sequences from a *Zaire ebolavirus*, a Bundibugyo ebolavirus, and a Sudan ebolavirus.

In one embodiment, the pharmaceutical composition comprises three recombinant MVA vaccines expressing glycoprotein and matrix protein sequences from a *Zaire ebolavirus*, a Bundibugyo ebolavirus, and a *Marburg marburgvirus*.

In one embodiment, the pharmaceutical composition comprises three recombinant MVA vaccines expressing glycoprotein and matrix protein sequences from a *Zaire ebolavirus*, a Sudan ebolavirus, and a *Marburg marburgvirus*.

In one embodiment, the pharmaceutical composition comprises three recombinant MVA vaccines expressing glycoprotein and matrix protein sequences from a Bundibugyo ebolavirus, a Sudan ebolavirus, and a *Marburg marburgvirus*.

In one embodiment, the pharmaceutical composition comprises three recombinant MVA vaccines expressing glycoprotein and matrix protein sequences from a *Zaire ebolavirus*, a Sudan ebolavirus, and a *Lassa virus*.

In one embodiment, the pharmaceutical composition comprises three recombinant MVA vaccines expressing glycoprotein and matrix protein sequences from a *Zaire ebolavirus*, a Bundibugyo ebolavirus, and a *Lassa virus*.

In one embodiment, the pharmaceutical composition comprises three recombinant MVA vaccines expressing glycoprotein and matrix protein sequences from a *Zaire ebolavirus*, a *Marburg marburgvirus*, and a *Lassa virus*.

In one embodiment, the pharmaceutical composition comprises three recombinant MVA vaccines expressing glycoprotein and matrix protein sequences from a Sudan ebolavirus, a Bundibugyo ebolavirus, and a *Lassa virus*.

In one embodiment, the pharmaceutical composition comprises three recombinant MVA vaccines expressing glycoprotein and matrix protein sequences from a Sudan ebolavirus, a *Marburg marburgvirus*, and a *Lassa virus*.

In one embodiment, the pharmaceutical composition comprises three recombinant MVA vaccines expressing glycoprotein and matrix protein sequences from a Bundibugyo ebolavirus, a *Marburg marburgvirus*, and a *Lassa virus*.

In one embodiment, the pharmaceutical composition comprises three recombinant MVA vaccines expressing glycoprotein and matrix protein sequences from a *Zaire ebolavirus*, a Sudan ebolavirus, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Zaire ebolavirus*, a Bundibugyo ebolavirus, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a *Zaire ebolavirus*, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a Sudan ebolavirus, a Bundibugyo ebolavirus, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a Sudan ebolavirus, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises three recombinant MVA vaccines expressing glycoprotein and matrix protein sequences from a Bundibugyo ebolavirus, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises four recombinant MVA vaccines expressing glycoprotein and matrix protein sequences from a *Zaire ebolavirus*, a Bundibugyo ebolavirus, a Sudan ebolavirus, and a *Marburg marburgvirus*.

In one embodiment, the pharmaceutical composition comprises four recombinant MVA vaccines expressing glycoprotein and matrix protein sequences from a *Zaire ebolavirus*, a Bundibugyo ebolavirus, a Sudan ebolavirus, and a *Lassa virus*.

In one embodiment, the pharmaceutical composition comprises four recombinant MVA vaccines expressing glycoprotein and matrix protein sequences from a Sudan ebolavirus, a Bundibugyo ebolavirus, a *Marburg marburgvirus*, and a *Lassa virus*.

In one embodiment, the pharmaceutical composition comprises four recombinant MVA vaccines expressing glycoprotein and matrix protein sequences from a *Zaire ebolavirus*, a Bundibugyo ebolavirus, a *Marburg marburgvirus*, and a *Lassa virus*.

In one embodiment, the pharmaceutical composition comprises four recombinant MVA vaccines expressing glycoprotein and matrix protein sequences from a *Zaire ebolavirus*, a Bundibugyo ebolavirus, a Sudan ebolavirus, and a *Lassa virus*, and the recombinant MVA comprising *Lassa virus* sequences also expresses the nucleoprotein of a *Lassa virus*.

In one embodiment, the pharmaceutical composition comprises four recombinant MVA vaccines expressing glycoprotein and matrix protein sequences from a Sudan ebolavirus, a Bundibugyo ebolavirus, a *Marburg marburgvirus*, and a *Lassa virus*, and the recombinant MVA comprising *Lassa virus* sequences also expresses the nucleoprotein of a *Lassa virus*.

In one embodiment, the pharmaceutical composition comprises four recombinant MVA vaccines expressing glycoprotein and matrix protein sequences from a *Zaire ebolavirus*, a Bundibugyo ebolavirus, a *Marburg marburgvirus*, and a *Lassa virus*, and the recombinant MVA comprising *Lassa virus* sequences also expresses the nucleoprotein of a *Lassa virus*.

In another aspect, the invention provides methods of inducing an immune response to ebolavirus, marburgvirus, or *Lassa virus* comprising administering an effective amount of a pharmaceutical composition comprising a recombinant MVA vaccine expressing glycoprotein and matrix protein from at least one species of ebolavirus, marburgvirus, or *Lassa virus*. The Lassa vaccine of this aspect may also express the *Lassa virus* nucleoprotein.

In another aspect, the invention provides methods of providing anti-ebolavirus, anti-marburgvirus, or anti-*Lassa virus* immunity comprising administering an effective amount of a pharmaceutical composition comprising a recombinant MVA vaccine expressing glycoprotein and matrix protein from at least one species of ebolavirus, marburgvirus, or *Lassa virus*. The Lassa vaccine of this aspect may also express the *Lassa virus* nucleoprotein.

In another aspect, the invention provides methods of reducing the spread of ebolavirus, marburgvirus, or *Lassa virus* infection within a subject or from an infected subject to an uninfected subject, comprising administering an effective amount of a pharmaceutical composition comprising a recombinant MVA vaccine expressing glycoprotein and matrix protein from at least one species of ebolavirus, marburgvirus, or *Lassa virus*. The Lassa vaccine of this aspect may also express the *Lassa virus* nucleoprotein. In another aspect, the invention provides methods of reducing symptoms of ebolavirus, marburgvirus, or *Lassa virus* infection comprising administering an effective amount of a pharmaceutical composition comprising a recombinant MVA vaccine expressing glycoprotein and matrix protein from at least one species of ebolavirus, marburgvirus, or *Lassa virus*. The Lassa vaccine of this aspect may also express the *Lassa virus* nucleoprotein. In another aspect, the invention provides methods of inducing an immune response which is considered a surrogate marker for protection against ebolavirus, marburgvirus, or *Lassa virus* infection. Data for determination of whether a response constitutes a surrogate marker for protection are obtained using immune response data obtained using the measurements outlined above.

It will also be appreciated that single or multiple administrations of the vaccine compositions of the present invention may be carried out. For example, subjects who are particularly susceptible to ebolavirus, marburgvirus, or *Lassa virus* infection may require multiple immunizations to establish and/or maintain protective immune responses. Levels of induced immunity can be monitored by measuring amounts of binding and neutralizing secretory and serum antibodies as well as levels of T cells, and dosages adjusted or vaccinations repeated as necessary to maintain desired levels of protection.

In one embodiment, administration is repeated at least twice, at least 3 times, at least 4 times, at least 5 times, at least 6 times, at least 7 times, at least 8 times, or more than 8 times.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 week, 3 week, 4 week or more than 4 week intervals are provided between administrations.

In one specific embodiment, a 4-week interval is used between 2 administrations.

Dosage

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0 \times 10^6$ TCID$_{50}$ to about $5.0 \times 10^9$ TCID$_{50}$. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a pathogenic species of ebolavirus. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or more polypeptides of the ebolavirus, marburgvirus, or *Lassa virus* (e.g., the ebolavirus, marburgvirus, or *Lassa virus* glycoprotein and large matrix protein; the Lassa vaccine of this invention may also express the *Lassa virus* nucleoprotein), or a nucleic acid molecule encoding one or more genes of the ebolavirus, marburgvirus, or *Lassa virus*, and is administered at a dosage of, e.g., between $1.0 \times 10^4$ and $9.9 \times 10^{12}$ TCID$_{50}$ of the viral vector, preferably between $1.0 \times 10^5$ TCID$_{50}$ and $1.0 \times 10^{11}$ TCID$_{50}$ pfu, more preferably between $1.0 \times 10^6$ and $1.0 \times 10^{10}$ TCID$_{50}$ pfu, or most preferably between $5.0 \times 10^6$ and $5.0 \times 10^9$ TCID$_{50}$. The composition may include, e.g., at least $5.0 \times 10^6$ TCID$_{50}$ of the viral vector (e.g., $1.0 \times 10^8$ TCID$_{50}$ of the viral vector). A physician or researcher can decide the appropriate amount and dosage regimen.

The composition of the method may include, e.g., between $1.0 \times 10^4$ and $9.9 \times 10^{12}$ TCID$_{50}$ of the viral vector, preferably between $1.0 \times 10^5$ TCID$_{50}$ and $1.0 \times 10^{11}$ TCID$_{50}$ pfu, more preferably between $1.0 \times 10^6$ and $1.0 \times 10^{10}$ TCID$_{50}$ pfu, or most preferably between $5.0 \times 10^6$ and $5.0 \times 10^9$ TCID$_{50}$. The composition may include, e.g., at least $5.0 \times 10^6$ TCID$_{50}$ of the viral vector (e.g., $1.0 \times 10^8$ TCID$_{50}$ of the viral vector). The method may include, e.g., administering the composition to the subject two or more times.

The invention also features a method of inducing an immune response to ebolavirus, marburgvirus, or *Lassa virus* in a subject (e.g., a human) that includes administering to the subject an effective amount of a recombinant viral vector that encodes at least one gene from the ebolavirus (e.g., the ebolavirus, marburgvirus, or *Lassa virus* glycoprotein and large matrix protein; the Lassa vaccine of this invention may also express the *Lassa virus* nucleoprotein). The infection may be caused by the *Zaire ebolavirus*, Sudan ebolavirus, nil Forest ebolavirus, Bundibugyo ebolavirus, or Reston ebolavirus species of ebolavirus; by the *Marburg marburgvirus* species of marburgvirus; or by the *Lassa virus* species of arenavirus. The subject being treated may not have, but is at risk of developing, an infection by an ebolavirus, a marburgvirus, or an arenavirus. Alternatively, the subject may already be infected with an ebolavirus, a marburgvirus, or an arenavirus. The composition may be administered, e.g., by injection (e.g., intramuscular, intraarterial, intravascular, intravenous, intraperitoneal, or subcutaneous).

The term "effective amount" is meant the amount of a composition administered to improve, inhibit, or ameliorate a condition of a subject, or a symptom of a disorder, in a clinically relevant manner (e.g., improve, inhibit, or ameliorate infection by ebolavirus, marburgvirus, or arenavirus or provide an effective immune response to infection by ebolavirus, marburgvirus, or arenavirus). Any improvement in the subject is considered sufficient to achieve treatment. Preferably, an amount sufficient to treat is an amount that prevents the occurrence or one or more symptoms of ebolavirus, marburgvirus, or arenavirus infection or is an amount that reduces the severity of, or the length of time during which a subject suffers from, one or more symptoms of ebolavirus, marburgvirus, or arenavirus infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of ebolavirus infection) varies depending upon the manner of administration and the age, body weight, and general health of the subject being treated. Ultimately, the prescribers or researchers will decide the appropriate amount and dosage.

It is important to note that the value of the present invention may never be demonstrated in terms of actual clinical benefit. Instead, it is likely that the value of the invention will be demonstrated in terms of success against a surrogate marker for protection. For an indication such as ebolavirus, marburgvirus, or *Lassa virus* infection, in which it is impractical or unethical to attempt to measure clinical benefit of an intervention, the FDA's Accelerated Approval process allows approval of a new vaccine based on efficacy against a surrogate endpoint. Therefore, the value of the invention may lie in its ability to induce an immune response that constitutes a surrogate marker for protection.

Similarly, FDA may allow approval of vaccines against ebolaviruses, marburgviruses, or arenaviruses based on its Animal Rule. In this case, approval is achieved based on efficacy in animals. The value of the invention may lie in its ability to protect relevant animal species against infection with ebolaviruses, marburgviruses, or arenaviruses, thus providing adequate evidence to justify its approval.

The composition of the method may include, e.g., between $1.0 \times 10^4$ and $9.9 \times 10^{12}$ TCID$_{50}$ of the viral vector, preferably between $1.0 \times 10^5$ TCID$_{50}$ and $1.0 \times 10^{11}$ TCID$_{50}$ pfu, more preferably between $1.0 \times 10^6$ and $1.0 \times 10^{10}$ TCID$_{50}$ pfu, or most preferably between $5.0 \times 10^6$ and $5.0 \times 10^9$ TCID$_{50}$. The composition may include, e.g., at least $5.0 \times 10^6$ TCID$_{50}$ of the viral vector (e.g., $1.0 \times 10^8$ TCID$_{50}$ of the viral vector). The method may include, e.g., administering the composition two or more times.

In some instances it may be desirable to combine the ebolavirus, marburgvirus, or arenavirus vaccines of the present invention with vaccines which induce protective responses to other agents, particularly other viruses. For example, the vaccine compositions of the present invention can be administered simultaneously, separately or sequentially with other genetic immunization vaccines such as those for influenza (Ulmer, J. B. et al., *Science* 259:1745-1749 (1993); Raz, E. et al., PNAS (USA) 91:9519-9523 (1994)), malaria (Doolan, D. L. et al., J. Exp. Med. 183:1739-1746 (1996); Sedegah, M. et al., PNAS (USA) 91:9866-9870 (1994)), and tuberculosis (Tascon, R. C. et al., Nat. Med. 2:888-892 (1996)).

Administration

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

In addition, single or multiple administrations of the compositions of the present invention may be given to a subject. For example, subjects who are particularly susceptible to ebolavirus infection may require multiple treatments to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against viral infection.

The claimed invention is further describe by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1. MVA Vaccine Vectors

This Example provides information on exemplary MVA vaccine vectors. Table 1 lists seven MVA vaccine vectors.

TABLE 1

MVA vaccine vectors

| Vaccine designation | GP sequence | Matrix protein sequence | Nucleoprotein sequence |
|---|---|---|---|
| GEO-EM01 | Optimized GP sequence for EBOV 2014 (current epidemic) | Optimized VP40 sequence for EBOV 2014 (current epidemic) | Not applicable |
| GEO-EM02 | Optimized GP sequence for EBOV, central EBOV sequence | Optimized VP40 sequence for EBOV, central EBOV sequence | Not applicable |
| GEO-EM03 | Optimized GP sequence for SUDV, central SUDV sequence | Optimized VP40 sequence for SUDV, central SUDV sequence | Not applicable |
| GEO-EM04 | Optimized GP sequence for BDBV, central BDBV sequence | Optimized VP40 sequence for BDBV, central BDBV sequence | Not applicable |
| GEO-EM05 | Optimized GP sequence for MARV, 1980 Mt. Elgon-Musoke strain | Optimized VP40 sequence for MARV, 1980 Mt. Elgon-Musoke strain | Not applicable |
| GEO-EM06 | Optimized GP sequence for LASV, Josiah strain | Optimized Z sequence for LASV, Josiah strain | Not applicable |
| GEO-EM07 | Optimized GP sequence for LASV, Josiah strain | Optimized Z sequence for LASV, Josiah strain | Optimized NP sequence for LASV, Josiah strain |

Table 2 lists the accession numbers for the GenBank sequences used for design of the five MVA vaccine vectors of this invention

TABLE 2

MVA vaccine vectors of this invention, source of sequences

| Vaccine designation | GenBank accession number for source sequence |
|---|---|
| GEO-EM01 | KM233103.1 |
| GEO-EM02 | KC242798.1 |
| GEO-EM03 | KC545390.1 |
| GEO-EM04 | KC545396.1 |
| GEO-EM05 | NC_001608 |
| GEO-EM06 | JN650517.1, JN650518.1 |
| GEO-EM07 | JN650517.1, JN650518.1 |

Example 2. Sequence Optimization

Example 2 illustrates the process for optimization of GP and VP40 sequences for use in an MVA vaccine vector. This Example shows the optimization of one GP and one VP40 sequence, both of which are included in GEO-EM01 (the vaccine for the 2014 EBOV strain). The process followed for vaccines against other strains is highly similar, involving the same set of operations.

The native nucleotide sequence for 2014 EBOV GP (which would lead to expression of sGP) was obtained from GenBank (accession number KM233103.1)

```
SEQ ID 01:
Native nucleotide sequence for 2014
EBOV GP, from GenBank:
ATGGGTGTTACAGGAATATTGCAGTTACCTCGTGA

TCGATTCAAGAGGACATCATTCTTTCTTTGGGTAA

TTATCCTTTTCCAAAGAACATTTTCCATCCCGCTT

GGAGTTATCCACAATAGTACATTACAGGTTAGTGA

TGTCGACAAACTAGTTTGTCGTGACAAACTGTCAT

CCACAAATCAATTGAGATCAGTTGGACTGAATCTC

GAGGGGAATGGAGTGGCAACTGACGTGCCATCTGT

GACTAAAAGATGGGCTTCAGGTCCGGTGTCCCAC

CAAAGGTGGTCAATTATGAAGCTGGTGAATGGGCT

GAAAACTGCTACAATCTTGAAATCAAAAAACCTGA

CGGGAGTGAGTGTCTACCAGCAGCGCCAGACGGGA

TTCGGGGCTTCCCCCGGTGCCGGTATGTGCACAAA

GTATCAGGAACGGGACCATGTGCCGGAGACTTTGC

CTTCCACAAAGAGGGTGCTTTCTTCCTGTATGATC

GACTTGCTTCCACAGTTATCTACCGAGGAACGACT

TTCGCTGAAGGTGTCGTTGCATTTCTGATACTGCC

CCAAGCTAAGAAGGACTTCTTCAGCTCACACCCCT

TGAGAGAGCCGGTCAATGCAACGGAGGACCCGTCG

AGTGGCTATTATTCTACCACAATTAGATATCAGGC

TACCGGTTTTGGAACTAATGAGACAGAGTACTTGT

TCGAGGTTGACAATTTGACCTACGTCCAACTTGAA

TCAAGATTCACACCACAGTTTCTGCTCCAGCTGAA

TGAGACAATATATGCAAGTGGGAAGAGGAGCAACA

CCACGGGAAAACTAATTTGGAAGGTCAACCCCGAA

ATTGATACAACAATCGGGGAGTGGGCCTTCTGGGA

AACTAAAAAAACCTCACTAGAAAAATTCGCAGTGA

AGAGTTGTCTTTCACAGCTGTATCAAACGGACCCA

AAAACATCAGTGGTCAGAGTCCGGCGCGAACTTCT

TCCGACCCAGAGACCAACACAACAAATGAAGACCA

CAAAATCATGGCTTCAGAAAATTCCTCTGCAATGG

TTCAAGTGCACAGTCAAGGAAGGAAAGCTGCAGTG

TCGCATCTGACAACCCTTGCCACAATCTCCACGAG

TCCTCAACCTCCCACAACCAAAACAGGTCCGGACA

ACAGCACCCATAATACACCCGTGTATAAACTTGAC

ATCTCTGAGGCAACTCAAGTTGGACAACATCACCG

TAGAGCAGACAACGACAGCACAGCCTCCGACACTC

CCCCCGCCACGACCGCAGCCGGACCCTTAAAAGCA
```

GAGAACACCAACACGAGTAAGAGCGCTGACTCCCT

GGACCTCGCCACCACGACAAGCCCCCAAAACTACA

GCGAGACTGCTGGCAACAACAACACTCATCACCAA

GATACCGGAGAAGAGAGTGCCAGCAGCGGGAAGCT

AGGCTTAATTACCAATACTATTGCTGGAGTAGCAG

GACTGATCACAGGCGGGAGAAGGACTCGAAGAGAA

GTAATTGTCAATGCTCAACCCAAATGCAACCCCAA

TTTACATTACTGGACTACTCAGGATGAAGGTGCTG

CAATCGGATTGGCCTGGATACCATATTTCGGGCCA

GCAGCCGAAGGAATTTACACAGAGGGGCTAATGCA

CAACCAAGATGGTTTAATCTGTGGGTTGAGGCAGC

TGGCCAACGAAACGACTCAAGCTCTCCAACTGTTC

CTGAGAGCCACAACTGAGCTGCGAACCTTTTCAAT

CCTCAACCGTAAGGCAATTGACTTCCTGCTGCAGC

GATGGGGTGGCACATGCCACATTTTGGGACCGGAC

TGCTGTATCGAACCACATGATTGGACCAAGAACAT

AACAGACAAAATTGATCAGATTATTCATGATTTTG

TTGATAAAACCCTTCCGGACCAGGGGGACAATGAC

AATTGGTGGACAGGATGGAGACAATGGATACCGGC

AGGTATTGGAGTTACAGGTGTTATAATTGCAGTTA

TCGCTTTATTCTGTATATGCAAATTTGTCTTTTAG

A single A nucleotide (indicated below by a bold underlined letter) was added to the native 2014 EBOV GP sequence (SEQ ID 01) to create the full-length GP sequence (SEQ ID 02). The purpose of this addition was to eliminate expression of the secreted form of the Ebola glycoprotein (sGP) and to ensure that full-length GP will be expressed. (Volchkov et al., 1995), Virology 214, 421-430). The GP sequence was translated in the EditSeq program (DNAStar) to verify that the sequence will express the full-length GP protein. SEQ ID: 03 is the product of the in silico translation.

```
SEQ ID 02:
Full-length 2014 EBOV GP
nucleotide sequence:
ATGGGTGTTACAGGAATATTGCAGTTACCTCGTGA

TCGATTCAAGAGGACATCATTCTTTCTTTGGGTAA

TTATCCTTTTCCAAAGAACATTTTCCATCCCGCTT

GGAGTTATCCACAATAGTACATTACAGGTTAGTGA

TGTCGACAAACTAGTTTGTCGTGACAAACTGTCAT

CCACAAATCAATTGAGATCAGTTGGACTGAATCTC

GAGGGGAATGGAGTGGCAACTGACGTGCCATCTGT

GACTAAAAGATGGGCTTCAGGTCCGGTGTCCCAC

CAAAGGTGGTCAATTATGAAGCTGGTGAATGGGCT

GAAAACTGCTACAATCTTGAAATCAAAAAACCTGA
```

-continued

```
CGGGAGTGAGTGTCTACCAGCAGCGCCAGACGGGA

TTCGGGGCTTCCCCCGGTGCCGGTATGTGCACAAA

GTATCAGGAACGGGACCATGTGCCGGAGACTTTGC

CTTCCACAAAGAGGGTGCTTTCTTCCTGTATGATC

GACTTGCTTCCACAGTTATCTACCGAGGAACGACT

TTCGCTGAAGGTGTCGTTGCATTTCTGATACTGCC

CCAAGCTAAGAAGGACTTCTTCAGCTCACACCCCT

TGAGAGAGCCGGTCAATGCAACGGAGGACCCGTCG

AGTGGCTATTATTCTACCACAATTAGATATCAGGC

TACCGGTTTTGGAACTAATGAGACAGAGTACTTGT

TCGAGGTTGACAATTTGACCTACGTCCAACTTGAA

TCAAGATTCACACCACAGTTTCTGCTCCAGCTGAA

TGAGACAATATATGCAAGTGGGAAGAGGAGCAACA

CCACGGGAAAACTAATTTGGAAGGTCAACCCCGAA

ATTGATACAACAATCGGGGAGTGGGCCTTCTGGGA

AACTAAAAAAAACCTCACTAGAAAAATTCGCAGTG

AAGAGTTGTCTTTCACAGCTGTATCAAACGGACCC

AAAAACATCAGTGGTCAGAGTCCGGCGCGAACTTC

TTCCGACCCAGAGACCAACACAACAAATGAAGACC

ACAAAATCATGGCTTCAGAAAATTCCTCTGCAATG

GTTCAAGTGCACAGTCAAGGAAGGAAAGCTGCAGT

GTCGCATCTGACAACCCTTGCCACAATCTCCACGA

GTCCTCAACCTCCCACAACCAAAACAGGTCCGGAC

AACAGCACCCATAATACACCCGTGTATAAACTTGA

CATCTCTGAGGCAACTCAAGTTGGACAACATCACC

GTAGAGCAGACAACGACAGCACAGCCTCCGACACT

CCCCCCGCCACGACCGCAGCCGGACCCTTAAAAGC

AGAGAACACCAACACGAGTAAGAGCGCTGACTCCC

TGGACCTCGCCACCACGACAAGCCCCCAAAACTAC

AGCGAGACTGCTGGCAACAACAACACTCATCACCA

AGATACCGGAGAAGAGAGTGCCAGCAGCGGGAAGC

TAGGCTTAATTACCAATACTATTGCTGGAGTAGCA

GGACTGATCACAGGCGGGAGAAGGACTCGAAGAGA

AGTAATTGTCAATGCTCAACCCAAATGCAACCCCA

ATTTACATTACTGGACTACTCAGGATGAAGGTGCT

GCAATCGGATTGGCCTGGATACCATATTTCGGGCC

AGCAGCCGAAGGAATTTACACAGAGGGGCTAATGC

ACAACCAAGATGGTTTAATCTGTGGGTTGAGGCAG

CTGGCCAACGAAACGACTCAAGCTCTCCAACTGTT

CCTGAGAGCCACAACTGAGCTGCGAACCTTTTCAA
```

```
TCCTCAACCGTAAGGCAATTGACTTCCTGCTGCAG

CGATGGGGTGGCACATGCCACATTTTGGGACCGGA

CTGCTGTATCGAACCACATGATTGGACCAAGAACA

TAACAGACAAAATTGATCAGATTATTCATGATTTT

GTTGATAAAACCCTTCCGGACCAGGGGACAATGA

CAATTGGTGGACAGGATGGGACAATGGATACCGG

CAGGTATTGGAGTTACAGGTGTTATAATTGCAGTT

ATCGCTTTATTCTGTATATGCAAATTTGTCTTTTA

G
```

SEQ ID 03:
Full-length 2014 EBOV GP
protein sequence, generated
in EditSeq software from
SEQ ID 02:

```
MGVTGILQLPRDRFKRTSFFLWVIILFQRTFSIPL

GVIHNSTLQVSDVDKLVCRDKLSSTNQLRSVGLNL

EGNGVATDVPSVTKRWGFRSGVPPKVVNYEAGEWA

ENCYNLEIKKPDGSECLPAAPDGIRGFPRCRYVHK

VSGTGPCAGDFAFHKEGAFFLYDRLASTVIYRGTT

FAEGVVAFLILPQAKKDFFSSHPLREPVNATEDPS

SGYYSTTIRYQATGFGTNETEYLFEVDNLTYVQLE

SRFTPQFLLQLNETIYASGKRSNTTGKLIWKVNPE

IDTTIGEWAFWETKKNLTRKIRSEELSFTAVSNGP

KNISGQSPARTSSDPETNTTNEDHKIMASENSSAM

VQVHSQGRKAAVSHLTTLATISTSPQPPTTKTGPD

NSTHNTPVYKLD1SEATQVGQHHRRADNDSTASDT

PPATTAAGPLKAENTNTSKSADSLDLATTTSPQNY

SETAGNNNTHHQDTGEESASSGKLGLITNTIAGVA

GLITGGRRTRREVIVNAQPKCNPNLHYWTTQDEGA

AIGLAWIPYFGPAAEGIYTEGLMFINQDGLICGLR

QLANETTQALQLFLRATTELRTFSILNRKAIDFLL

QRWGGTCHILGPDCCIEPHDWTKNITDKIDQIIHD

FVDKTLPDQGDNDNWWTGWRQWIPAGIGVTGVIIA

VIALFCICKFVF
```

The full-length 2014 EBOV GP sequence (SEQ ID 02) was optimized for vaccinia virus expression using the online Gene Optimizer algorithm to generate SEQ ID 04.

SEQ ID 04:
Codon-optimized full-length
2014 EBOV GP sequence:

```
ATGGGAGTAACTGGAATTCTACAACTACCAAGAGA

TAGATTCAAAAGAACATCTTTTTTTCTATGGGTTA

TAATTCTATTTCAAAGAACATTTTCTATTCCATTG

GGAGTAATTCATAATTCTACATTGCAAGTATCTGA

TGTAGATAAACTAGTATGTAGAGATAAATTGTCTA
```

-continued
```
GTACAAATCAACTAAGATCTGTAGGATTGAATCTA
GAAGGAAATGGTGTAGCGACAGATGTTCCATCTGT
AACAAAAAGATGGGGTTTTAGATCTGGTGTACCAC
CAAAAGTAGTAAATTATGAAGCGGGAGAATGGGCG
GAAAATTGTTATAATCTAGAAATTAAAAAACCAGA
TGGATCTGAATGTCTACCAGCGGCGCCAGATGGAA
TTAGAGGATTTCCAAGATGTAGATATGTTCATAAA
GTATCTGGAACAGGACCATGTGCGGGAGATTTTGC
GTTTCATAAAGAAGGAGCATTTTTTCTATATGATA
GACTAGCGTCTACAGTAATATATAGAGGAACAACA
TTTGCGGAAGGTGTAGTAGCTTTTCTAATTCTACC
ACAAGCGAAAAAGATTTTTTAGTTCTCATCCAC
TAAGAGAACCAGTAAATGCGACAGAAGATCCTTCT
TCTGGATATTATTCTACTACAATTAGATATCAAGC
GACAGGATTTGGAACAAATGAAACAGAATATCTAT
TTGAAGTTGATAATCTAACATATGTACAACTAGAA
AGTAGATTCACACCACAATTTCTATTGCAATTGAA
TGAAACAATATATGCGTCTGGAAAAAGATCTAATA
CAACTGGAAAACTAATTTGGAAAGTAAATCCAGAA
ATTGATACAACAATTGGAGAATGGGCTTTTTGGGA
AACAAAAAAAATTTGACAAGAAAAATTAGATCTG
AAGAATTGTCTTTTACAGCGGTATCTAATGGACCA
AAAAATATTTCTGGACAATCTCCAGCGAGAACTTC
TTCTGATCCAGAAACAAATACTACAAATGAAGATC
ACAAAATTATGGCGTCTGAAAATTCTTCTGCTATG
GTACAAGTACATTCTCAAGGAAGAAAAGCGGCGGT
ATCTCATCTAACAACACTAGCGACTATTTCTACAT
CTCCACAACCACCAACAACAAAAACTGGACCAGAT
AATAGTACACATAATACTCCAGTTTATAAACTAGA
TATTTCTGAAGCGACACAAGTTGGACAACATCATA
GAAGAGCGGATAATGATTCTACAGCGTCTGATACA
CCACCAGCTACAACAGCTGCTGGACCATTGAAAGC
GGAAAATACAAATACTTCTAAATCTGCGGATTCTC
TAGATTTGGCGACAACAACTTCTCCTCAAAATTAT
TCTGAAACAGCGGGAAATAATAATACTCATCATCA
AGATACTGGAGAAGAATCTGCGTCTAGTGGAAAAT
TGGGACTAATTACAAATACAATTGCGGGTGTAGCG
GGATTGATTACTGGTGGAAGAAGAACTAGAAGAGA
AGTAATAGTTAATGCGCAACCTAAATGTAATCCAA
ATCTACATTATTGGACAACTCAAGATGAAGGTGCT
GCGATTGGACTAGCTTGGATTCCATATTTTGGACC
TGCGGCGAAGGAATATATACTGAAGGACTAATGC
ATAATCAAGATGGACTAATTTGTGGACTAAGACAA
CTAGCGAATGAAACTACACAAGCGCTACAACTATT
TTTGAGAGCGACAACAGAACTAAGAACTTTTAGTA
TTCTAAATAGAAAAGCGATTGATTTTTTGCTACAA
AGATGGGGAGGAACATGTCATATTCTAGGACCAGA
TTGTTGTATTGAACCACATGATTGGACAAAAAATA
TTACAGACAAAATTGATCAAATTATTCATGATTTT
GTTGATAAAACACTACCAGATCAAGGAGATAATGA
TAATTGGTGGACAGGATGGAGACAATGGATTCCAG
CGGGAATTGGAGTAACAGGTGTAATTATTGCGGTT
ATTGCGCTATTTTGTATATGTAAATTTGTTTTTTA
A
```

The codon-optimized full-length 2014 EBOV GP sequence (SEQ ID 04) was searched for homopolymer stretches consisting of ≥5 G bases or ≥C bases. None were found.

The codon-optimized full-length 2014 EBOV GP sequence (SEQ ID 04) was searched for homopolymer stretches consisting of ≥5 T bases or ≥A bases. Fifteen such stretches were found and were eliminated through silent mutations as listed in Table 3, to generate SEQ ID 05.

TABLE 3

Elimination of homopolymer stretches in optimized 2014 EBOV GP sequence

| No. | Homopolymer | Changes (Silent mutation) | Mutation position (base number) in sequence | Codon change (silent mutation) |
|---|---|---|---|---|
| 1 | 7T | T to C | 57 | TTT to TTC |
| 2 | 5A | A to G | 252 | AAA to AAG |
| 3 | 6A | A to G | 342 | AAA to AAG |
| 4 | 6T | T to C | 477 | TTT to TTC |
| 5 | 6A | A to G | 570 | AAA to AAG |
| 6 | 7T | T to C | 579 | TTT to TTC |
| 7 | 6A | A to G | 795 | AAA to AAG |
| 8 | 5T | T to C | 870 | TTT to TTC |
| 9 | 9A | A to G | 882 885 | AAA to AAG |
| 10 | 5A | A to G | 900 | AAA to AAG |
| 11 | 6A | A to G | 948 | AAA to AAG |
| 12 | 5A | A to G | 1143 | AAA to AAG |
| 13 | 5T | T to C | 1716 | TTT to TTC |
| 14 | 6T | T to C | 1776 | TTT to TTC |
| 15 | 6A | A to G | 1851 | AAA to AAG |

*Shown as lower case in SEQ ID NO: 5

```
SEQ ID 05:
Homopolymer-free, codon-optimized,
full-length 2014 EBOV GP sequence:
ATGGGAGTAACTGGAATTCTACAACTACCAAGAGA
TAGATTCAAAAGAACATCTTTcTTTCTATGGGTTA
TAATTCTATTTCAAAGAACATTTTCTATTCCATTG
GGAGTAATTCATAATTCTACATTGCAAGTATCTGA
```

-continued

TGTAGATAAACTAGTATGTAGAGATAAATTGTCTA

GTACAAATCAACTAAGATCTGTAGGATTGAATCTA

GAAGGAAATGGTGTAGCGACAGATGTTCCATCTGT

AACAAAgAGATGGGGTTTTAGATCTGGTGTACCAC

CAAAAGTAGTAAATTATGAAGCGGGAGAATGGGCG

GAAAATTGTTATAATCTAGAAATTAAgAAACCAGA

TGGATCTGAATGTCTACCAGCGGCGCCAGATGGAA

TTAGAGGATTTCCAAGATGTAGATATGTTCATAAA

GTATCTGGAACAGGACCATGTGCGGGAGATTTTGC

GTTTCATAAAGAAGGAGCATTcTTTCTATATGATA

GACTAGCGTCTACAGTAATATATAGAGGAACAACA

TTTGCGGAAGGTGTAGTAGCTTTTCTAATTCTACC

ACAAGCGAAgAAAGATTTcTTTAGTTCTCATCCAC

TAAGAGAACCAGTAAATGCGACAGAAGATCCTTCT

TCTGGATATTATTCTACTACAATTAGATATCAAGC

GACAGGATTTGGAACAAATGAAACAGAATATCTAT

TTGAAGTTGATAATCTAACATATGTACAACTAGAA

AGTAGATTCACACCACAATTTCTATTGCAATTGAA

TGAAACAATATATGCGTCTGGAAAgAGATCTAATA

CAACTGGAAAACTAATTTGGAAAGTAAATCCAGAA

ATTGATACAACAATTGGAGAATGGGCTTTcTGGGA

AACAAAgAAgAATTTGACAAGAAAgATTAGATCTG

AAGAATTGTCTTTTACAGCGGTATCTAATGGACCA

AAgAATATTTCTGGACAATCTCCAGCGAGAACTTC

TTCTGATCCAGAAACAAATACTACAAATGAAGATC

ACAAAATTATGGCGTCTGAAAATTCTTCTGCTATG

GTACAAGTACATTCTCAAGGAAGAAAAGCGGCGGT

ATCTCATCTAACAACACTAGCGACTATTTCTACAT

CTCCACAACCACCAACAACAAAgACTGGACCAGAT

AATAGTACACATAATACTCCAGTTTATAAACTAGA

TATTTCTGAAGCGACACAAGTTGGACAACATCATA

GAAGAGCGGATAATGATTCTACAGCGTCTGATACA

CCACCAGCTACAACAGCTGCTGGACCATTGAAAGC

GGAAAATACAAATACTTCTAAATCTGCGGATTCTC

TAGATTTGGCGACAACAACTTCTCCTCAAAATTAT

TCTGAAACAGCGGGAAATAATAATACTCATCATCA

AGATACTGGAGAAGAATCTGCGTCTAGTGGAAAAT

TGGGACTAATTACAAATACAATTGCGGGTGTAGCG

GGATTGATTACTGGTGGAAGAAGAACTAGAAGAGA

AGTAATAGTTAATGCGCAACCTAAATGTAATCCAA

-continued

ATCTACATTATTGGACAACTCAAGATGAAGGTGCT

GCGATTGGACTAGCTTGGATTCCATATTTTGGACC

TGCGGCGGAAGGAATATATACTGAAGGACTAATGC

ATAATCAAGATGGACTAATTTGTGGACTAAGACAA

CTAGCGAATGAAACTACACAAGCGCTACAACTATT cTTGAGAGCGACAACAGAACTAAGAACTTTTAGTA

TTCTAAATAGAAAAGCGATTGATTTcTTGCTACAA

AGATGGGGAGGAACATGTCATATTCTAGGACCAGA

TTGTTGTATTGAACCACATGATTGGACAAAgAATA

TTACAGACAAAATTGATCAAATTATTCATGATTTT

GTTGATAAAACACTACCAGATCAAGGAGATAATGA

TAATTGGTGGACAGGATGGAGACAATGGATTCCAG

CGGGAATTGGAGTAACAGGTGTAATTATTGCGGTT

ATTGCGCTATTTTGTATATGTAAATTTGTTTTTTA

A

The homopolymer-free, codon-optimized, full-length 2014 EBOV GP sequence (SEQ ID 05) was searched for vaccinia transcription terminator motifs. None were found.

A second stop codon and a vaccinia transcription terminator sequence were added at the end of the homopolymer-free, codon-optimized, full-length 2014 EBOV GP sequence (SEQ ID 05) to generate SEQ ID 06.

SEQ ID 06:
Homopolymer-free, codon-optimized,
full-length 2014 EBOV GP sequence
with stop codon and transcription
terminator added:
ATGGGAGTAACTGGAATTCTACAACTACCAAGAGA TAGATTCAAAAGAACATCTTTcTTTCTATGGGTTA

TAATTCTATTTCAAAGAACATTTTCTATTCCATTG

GGAGTAATTCATAATTCTACATTGCAAGTATCTGA

TGTAGATAAACTAGTATGTAGAGATAAATTGTCTA

GTACAAATCAACTAAGATCTGTAGGATTGAATCTA

GAAGGAAATGGTGTAGCGACAGATGTTCCATCTGT

AACAAAgAGATGGGGTTTTAGATCTGGTGTACCAC

CAAAAGTAGTAAATTATGAAGCGGGAGAATGGGCG

GAAAATTGTTATAATCTAGAAATTAAgAAACCAGA

TGGATCTGAATGTCTACCAGCGGCGCCAGATGGAA

TTAGAGGATTTCCAAGATGTAGATATGTTCATAAA

GTATCTGGAACAGGACCATGTGCGGGAGATTTTGC

GTTTCATAAAGAAGGAGCATTcTTTCTATATGATA

GACTAGCGTCTACAGTAATATATAGAGGAACAACA

TTTGCGGAAGGTGTAGTAGCTTTTCTAATTCTACC

ACAAGCGAAgAAAGATTTcTTTAGTTCTCATCCAC

TAAGAGAACCAGTAAATGCGACAGAAGATCCTTCT

TCTGGATATTATTCTACTACAATTAGATATCAAGC

GACAGGATTTGGAACAAATGAAACAGAATATCTAT

TTGAAGTTGATAATCTAACATATGTACAACTAGAA

AGTAGATTCACACCACAATTTCTATTGCAATTGAA

TGAAACAATATATGCGTCTGGAAAgAGATCTAATA

CAACTGGAAAACTAATTTGGAAAGTAAATCCAGAA

ATTGATACAACAATTGGAGAATGGGCTTTcTGGGA

AACAAAgAAgAATTTGACAAGAAAgATTAGATCTG

AAGAATTGTCTTTTACAGCGGTATCTAATGGACCA

AAgAATATTTCTGGACAATCTCCAGCGAGAACTTC

TTCTGATCCAGAAACAAATACTACAAATGAAGATC

ACAAAATTATGGCGTCTGAAAATTCTTCTGCTATG

GTACAAGTACATTCTCAAGGAAGAAAAGCGGCGGT

ATCTCATCTAACAACACTAGCGACTATTTCTACAT

CTCCACAACCACCAACAACAAAgACTGGACCAGAT

AATAGTACACATAATACTCCAGTTTATAAACTAGA

TATTTCTGAAGCGACACAAGTTGGACAACATCATA

GAAGAGCGGATAATGATTCTACAGCGTCTGATACA

CCACCAGCTACAACAGCTGCTGGACCATTGAAAGC

GGAAAATACAAATACTTCTAAATCTGCGGATTCTC

TAGATTTGGCGACAACAACTTCTCCTCAAAATTAT

TCTGAAACAGCGGGAAATAATAATACTCATCATCA

AGATACTGGAGAAGAATCTGCGTCTAGTGGAAAAT

TGGGACTAATTACAAATACAATTGCGGGTGTAGCG

GGATTGATTACTGGTGGAAGAAGAACTAGAAGAGA

AGTAATAGTTAATGCGCAACCTAAATGTAATCCAA

ATCTACATTATTGGACAACTCAAGATGAAGGTGCT

GCGATTGGACTAGCTTGGATTCCATATTTTGGACC

TGCGGCGGAAGGAATATATACTGAAGGACTAATGC

ATAATCAAGATGGACTAATTTGTGGACTAAGACAA

CTAGCGAATGAAACTACACAAGCGCTACAACTATT cTTGAGAGCGACAACAGAACTAAGAACTTTTAGTA

TTCTAAATAGAAAAGCGATTGATTTcTTGCTACAA

AGATGGGGAGGAACATGTCATATTCTAGGACCAGA

TTGTTGTATTGAACCACATGATTGGACAAAgAATA

TTACAGACAAAATTGATCAAATTATTCATGATTTT

GTTGATAAAACACTACCAGATCAAGGAGATAATGA

TAATTGGTGGACAGGATGGAGACAATGGATTCCAG

CGGGAATTGGAGTAACAGGTGTAATTATTGCGGTT

ATTGCGCTATTTTGTATATGTAAATTTGTTTTTTA

ATAATTTTTAT

The native nucleotide sequence for 2014 EBOV VP40 was obtained from GenBank (accession number KM233103.1)

SEQ ID 07:
Native nucleotide sequence
for 2014 EBOV VP40, from
GenBank:
ATGAGGCGGGTTATATTGCCTACTGCTCCTCCTGA

ATATATGGAGGCCATATACCCTGCCAGGTCAAATT

CAACAATTGCTAGGGGTGGCAACAGCAATACAGGC

TTCCTGACACCGGAGTCAGTCAATGGAGACACTCC

ATCGAATCCACTCAGGCCAATTGCTGATGACACCA

TCGACCATGCCAGCCACACACCAGGCAGTGTGTCA

TCAGCATTCATCCTCGAAGCTATGGTGAATGTCAT

ATCGGGCCCCAAAGTGCTAATGAAGCAAATTCCAA

TTTGGCTTCCTCTAGGTGTCGCTGATCAAAGACC

TACAGCTTTGACTCAACTACGGCCGCCATCATGCT

TGCTTCATATACTATCACCCATTTCGGCAAGGCAA

CCAATCCGCTTGTCAGAGTCAATCGGCTGGGTCCT

GGAATCCCGGATCACCCCCTCAGGCTCCTGCGAAT

TGGAAACCAGGCTTTCCTCCAGGAGTTCGTTCTTC

CACCAGTCCAACTACCCCAGTATTTCACCTTTGAT

TTGACAGCACTCAAACTGATCACTCAACCACTGCC

TGCTGCAACATGGACCGATGACACTCCAACTGGAT

CAAATGGAGCGTTGCGTCCAGGAATTTCATTTCAT

CCAAAACTTCGCCCCATTCTTTTACCCAACAAAAG

TGGGAAGAAGGGGAACAGTGCCGATCTAACATCTC

CGGAGAAAATCCAAGCAATAATGACTTCACTCCAG

GACTTTAAGATCGTTCCAATTGATCCAACCAAAAA

TATCATGGGTATCGAAGTGCCAGAAACTCTGGTCC

ACAAGCTGACCGGTAAGAAGGTGACTTCCAAAAAT

GGACAACCAATCATCCCTGTTCTTTTGCCAAAGTA

CATTGGGTTGGACCCGGTGGCTCCAGGAGACCTCA

CCATGGTAATCACACAGGATTGTGACACGTGTCAT

TCTCCTGCAAGTCTTCCAGCTGTGGTTGAGAAGTA

A

The native nucleotide sequence for 2014 EBOV VP40 (SEQ ID 07) was optimized for vaccinia virus expression using the online Gene Optimizer algorithm.

The codon-optimized 2014 EBOV VP40 sequence was searched for homopolymer stretches consisting of ≥5 G bases or ≥C bases. None were found.

The codon-optimized 2014 EBOV VP40 sequence was searched for homopolymer stretches consisting of ≥5 T bases or ≥5 A bases. Five such stretches were found and were eliminated through silent mutations as listed in Table 4, to generate SEQ ID 08.

TABLE 4

Elimination of homopolymer stretches in optimized 2014 EBOV VP40 sequence

| No. | Homopolymer | Changes (Silent mutation) | Mutation position (base number) in sequence | Codon change (silent mutation) |
| --- | --- | --- | --- | --- |
| 1 | 6A | A to G | 312 | AAA to AAG |
| 2 | 7A | A to G | 672 | AAA to AAG |
| 3 | 6A | A to G | 708 | AAA to AAG |
| 4 | 6A | A to G | 768 | AAA to AAG |
| 5 | 7A | A to G | 822 | AAA to AAG |

*Shown as lower case in SEQ ID NO: 8 and SEQ ID NO: 9

SEQ ID 08:
Homopolymer-free, codon-optimized
2014 EBOV VP40 sequence:
ATGAGAAGAGTAATTCTACCAACAGCGCCACCAGA

ATATATGGAAGCGATATATCCAGCGAGATCTAATT

CTACAATTGCGAGAGGTGGAAATTCTAATACTGGA

TTTCTAACACCAGAATCTGTAAATGGAGATACACC

ATCTAATCCACTAAGACCAATTGCGGATGATACAA

TAGATCATGCGAGTCATACTCCAGGATCTGTATCT

TCTGCTTTTATTCTAGAAGCTATGGTTAATGTAAT

TTCTGGACCAAAAGTACTAATGAAACAAATTCCAA

TTTGGCTACCATTGGGAGTAGCGGATCAAAAgACA

TATTCTTTTGATTCTACTACAGCGGCGATTATGCT

AGCGTCTTATACAATTACACATTTTGGAAAAGCGA

CAAATCCACTAGTTAGAGTAAATAGACTAGGACCT

GGAATACCAGATCATCCATTGAGACTACTAAGAAT

TGGAAATCAAGCTTTTCTACAAGAATTTGTTCTAC

CACCAGTACAACTACCACAATACTTTACATTTGAT

CTAACAGCGCTAAAACTAATTACACAACCATTGCC

AGCGGCGACATGGACAGATGATACACCAACAGGAT

CTAATGGTGCTCTAAGACCTGGTATTTCTTTTCAT

CCAAAACTAAGACCTATTCTATTGCCAAATAAATC

TGGAAAgAAAGGAAATTCTGCGGATCTAACATCTC

CAGAAAAgATTCAAGCGATTATGACATCTCTACAA

GACTTCAAAATTGTACCAATTGATCCAACAAAgAA

TATTATGGGAATTGAAGTACCAGAAACACTAGTTC

ATAAACTAACTGGAAAgAAAGTAACATCTAAAAAT

GGACAACCTATTATTCCAGTATTGCTACCTAAATA

TATTGGACTAGATCCAGTAGCGCCTGGAGATCTAA

CAATGGTTATTACACAAGATTGTGATACTTGTCAT

TCTCCAGCGAGTTTGCCTGCGGTAGTAGAAAAATA

A

The homopolymer-free, codon-optimized, full-length 2014 EBOV GP sequence (SEQ ID 08) was searched for vaccinia transcription terminator motifs. None were found.

A second stop codon and a vaccinia transcription terminator sequence were added at the end of the homopolymer-free, codon-optimized 2014 EBOV VP40 sequence (SEQ ID 08) to generate SEQ ID 09.

SEQ ID 09:
Homopolymer-free, codon-optimized
2014 EBOV VP40 sequence with stop
codon and transcription terminator
added:
ATGAGAAGAGTAATTCTACCAACAGCGCCACCAGA

ATATATGGAAGCGATATATCCAGCGAGATCTAATT

CTACAATTGCGAGAGGTGGAAATTCTAATACTGGA

TTTCTAACACCAGAATCTGTAAATGGAGATACACC

ATCTAATCCACTAAGACCAATTGCGGATGATACAA

TAGATCATGCGAGTCATACTCCAGGATCTGTATCT

TCTGCTTTTATTCTAGAAGCTATGGTTAATGTAAT

TTCTGGACCAAAAGTACTAATGAAACAAATTCCAA

TTTGGCTACCATTGGGAGTAGCGGATCAAAAgACA

TATTCTTTTGATTCTACTACAGCGGCGATTATGCT

AGCGTCTTATACAATTACACATTTTGGAAAAGCGA

CAAATCCACTAGTTAGAGTAAATAGACTAGGACCT

GGAATACCAGATCATCCATTGAGACTACTAAGAAT

TGGAAATCAAGCTTTTCTACAAGAATTTGTTCTAC

CACCAGTACAACTACCACAATACTTTACATTTGAT

CTAACAGCGCTAAAACTAATTACACAACCATTGCC

AGCGGCGACATGGACAGATGATACACCAACAGGAT

CTAATGGTGCTCTAAGACCTGGTATTTCTTTTCAT

CCAAAACTAAGACCTATTCTATTGCCAAATAAATC

TGGAAAgAAAGGAAATTCTGCGGATCTAACATCTC

CAGAAAAgATTCAAGCGATTATGACATCTCTACAA

GACTTCAAAATTGTACCAATTGATCCAACAAAgAA

TATTATGGGAATTGAAGTACCAGAAACACTAGTTC

ATAAACTAACTGGAAAgAAAGTAACATCTAAAAAT

GGACAACCTATTATTCCAGTATTGCTACCTAAATA

TATTGGACTAGATCCAGTAGCGCCTGGAGATCTAA

CAATGGTTATTACACAAGATTGTGATACTTGTCAT

TCTCCAGCGAGTTTGCCTGCGGTAGTAGAAAAATA

ATAATTTTTAT

Example 3: Additional Antigen Sequences for Filovirus MVA Vaccine

In another exemplary embodiment, sequences from Zaire Ebola (ZEBOV) and Sudan Ebola Virus (SUDV) are prepared in shuttle plasmids and optimized. Viral sequences are then inserted into MVA vector vaccines described herein. These sequences are modified from native sequences using the methods described herein.

TABLE 5

Zaire Ebola VP40 mutation table

| Changes (Silent mutation) | Mutation position on VP40 |
|---|---|
| A to G | 312 |
| A to G | 672 |
| A to G | 708 |
| A to G | 768 |
| A to G | 822 |

*Shown as lower case in SEQ ID NO: 10

```
SEQ ID 10:
pGEO-ZEBOV2014 VP40 sequence optimized
for insertion into MVA vector:
(FIG. 3)
GAATTCGGAGTATACGAACCGGGAAAGAGAAGATG

GTTAAAAATAAAGCGAGACTATTTGAACGAGGGTT

CCATGGCAGATTCTGCCGATTTAGTAGTACTAGGT

GCTTACTATGGTAAAGGAGCAAAGGGTGGTATCAT

GGCAGTCTTTCTAATGGGTTGTTACGACGATGAAT

CCGGTAAATGGAAGACGGTTACCAAGTGTTCAGGA

CACGATGATAATACGTTAAGGGAGTTGCAAGACCA

ATTAAAGATGATTAAAATTAACAAGGATCCCAAAA

AAATTCCAGAGTGGTTAGTAGTTAATAAAATCTAT

ATTCCCGATTTTGTAGTAGAGGATCCAAAACAATC

TCAGATATGGGAAATTTCAGGAGCAGAGTTTACAT

CTTCCAAGTCCCATACCGCAAATGGAATATCCATT

AGATTTCCTAGATTTACTAGGATAAGAGAGGATAA

AACGTGGAAAGAATCTACTCATCTAAACGATTTAG

TAAACTTGACTAAATCTTAATTTTTATGGCGCGCC

TTTCATTTGTTTTTTTCTATGCTATAAATGGTGA

GCAAGGGCGAGGAGCTGTTCACCGGGGTGGTGCCC

ATCCTGGTCGAGCTGGACGGCGACGTAAACGGCCA

CAAGTTCAGCGTGTCCGGCGAGGGCGAGGGCGATG

CCACCTACGGCAAGCTGACCCTGAAGTTCATCTGC

ACCACCGGCAAGCTGCCCGTGCCCTGGCCCACCCT

CGTGACCACCCTGACCTACGGCGTGCAGTGCTTCA

GCCGCTACCCCGACCACATGAAGCAGCACGACTTC

TTCAAGTCCGCCATGCCCGAAGGCTACGTCCAGGA

GCGCACCATCTTCTTCAAGGACGACGGCAACTACA

AGACCCGCGCCGAGGTGAAGTTCGAGGGCGACACC

CTGGTGAACCGCATCGAGCTGAAGGGCATCGACTT

CAAGGAGGACGGCAACATCCTGGGGCACAAGCTGG

AGTACAACTACAACAGCCACAACGTCTATATCATG

GCCGACAAGCAGAAGAACGGCATCAAGGTGAACTT

CAAGATCCGCCACAACATCGAGGACGGCAGCGTGC

AGCTCGCCGACCACTACCAGCAGAACACCCCCATC

GGCGACGGCCCCGTGCTGCTGCCCGACAACCACTA

CCTGAGCACCCAGTCCGCCCTGAGCAAAGACCCCA

ACGAGAAGCGCGATCACATGGTCCTGCTGGAGTTC

GTGACCGCCGCCGGGATCACTCTCGGCATGCACGA

GCTGTACAAGTAAGAGCTCCCCGATTTTGTAGTAG

AGGATCCAAAACAATCTCAGATATGGGAAATTTCA

GGAGCAGAGTTTACATCTTCCAAGTCCCATACCGC

AAATGGAATATCCATTAGATTTCCTAGATTTACTA

GGATAAGAGAGGATAAAACGTGGAAAGAATCTACT

CATCTAAACGATTTAGTAAACTTGACTAAATCTTA

ATTTTTATCTCGAGGCCGCTGGTACCCAACCTAAA

AATTGAAAATAAATACAAAGGTTCTTGAGGGTTGT

GTTAAATTGAAAGCGAGAAATAATCATAAATAAGC

CCgggATGAGAAGAGTAATTCTACCAACAGCGCCA

CCAGAATATATGGAAGCGATATATCCAGCGAGATC

TAATTCTACAATTGCGAGAGGTGGAAATTCTAATA

CTGGATTTCTAACACCAGAATCTGTAAATGGAGAT

ACACCATCTAATCCACTAAGACCAATTGCGGATGA

TACAATAGATCATGCGAGTCATACTCCAGGATCTG

TATCTTCTGCTTTTATTCTAGAAGCTATGGTTAAT

GTAATTTCTGGACCAAAAGTACTAATGAAACAAAT

TCCAATTTGGCTACCATTGGGAGTAGCGGATCAAA

AgACATATTCTTTTGATTCTACTACAGCGGCGATT

ATGCTAGCGTCTTATACAATTACACATTTTGGAAA

AGCGACAAATCCACTAGTTAGAGTAAATAGACTAG

GACCTGGAATACCAGATCATCCATTGAGACTACTA

AGAATTGGAAATCAAGCTTTTCTACAAGAATTTGT

TCTACCACCAGTACAACTACCACAATACTTTACAT

TTGATCTAACAGCGCTAAAACTAATTACACAACCA

TTGCCAGCGGCGACATGGACAGATGATACACCAAC

AGGATCTAATGGTGCTCTAAGACCTGGTATTTCTT

TTCATCCAAAACTAAGACCTATTCTATTGCCAAAT

AAATCTGGAAAgAAAGGAAATTCTGCGGATCTAAC
```

```
ATCTCCAGAAAAgATTCAAGCGATTATGACATCTC

TACAAGACTTCAAAATTGTACCAATTGATCCAACA

AAgAATATTATGGGAATTGAAGTACCAGAAACACT

AGTTCATAAACTAACTGGAAAgAAAGTAACATCTA

AAAATGGACAACCTATTATTCCAGTATTGCTACCT

AAATATATTGGACTAGATCCAGTAGCGCCTGGAGA

TCTAACAATGGTTATTACACAAGATTGTGATACTT

GTCATTCTCCAGCGAGTTTGCCTGCGGTAGTAGAA

AAATAATAATTTTTATgTCGACCTGCAGCTAATGT

ATTAGTTAAATATTAAAACTTACCACGTAAAACTT

AAAATTTAAAATGATATTTCATTGACAGATAGATC

ACACATTATGAACTTTCAAGGACTTGTGTTAACTG

ACAATTGCAAAAATCAATGGGTCGTTGGACCATTA

ATAGGAAAAGGTGGATTTGGTAGTATTTATACTAC

TAATGACAATAATTATGTAGTAAAAATAGAGCCCA

AAGCTAACGGATCATTATTTACCGAACAGGCATTT

TATACTAGAGTACTTAAACCATCCGTTATCGAAGA

ATGGAAAAAATCTCACAATATAAAGCACGTAGGTC

TTATCACGTGCAAGGCATTTGGTCTATACAAATCC

ATTAATGTGGAATATCGATTCTTGGTAATTAATAG

ATTAGGTGCAGATCTAGATGCGGTGATCAGAGCCA

ATAATAATAGATTACCAAAAAGGTCGGTGATGTTG

ATCGGAATCGAAATCTTAAATACCATACAATTTAT

GCACGAGCAAGGATATTCTCACGGAGATATTAAAG

CGAGTAATATAGTCTTGGATCAAATAGATAAGAAT

AAATTATATCTAGTGGATTACGGATTGGTTTCTAA

ATTCATGTCAAGCTTGTCTCCCTATAGTGAGTCGT

ATTAGAGCTTGGCGTAATCATGGTCATAGCTGTTT

CCTGTGTGAAATTGTTATCCGCTCACAATTCCACA

CAACATACGAGCCGGAAGCATAAAGTGTAAAGCCT

GGGGTGCCTAATGAGTGAGCTAACTCACATTAATT

GCGTTGCGCTCACTGCCCGCTTTCGAGTCGGGAAA

CCTGTCGTGCCAGCTGCATTAATGAATCGGCCAAC

GCGCGGGGAGAGGCGGTTTGCGTATTGGGCGCTCT

TCCGCTTCCTCGCTCACTGACTCGCTGCGCTCGGT

CGTTCGGCTGCGGCGAGCGGTATCAGCTCACTCAA

AGGCGGTAATACGGTTATCCACAGAATCAGGGGAT

AACGCAGGAAAGAACATGTGAGCAAAAGGCCAGCA

AAAGGCCAGGAACCGTAAAAAGGCCGCGTTGCTGG

CGTTTTTCGATAGGCTCCGCCCCCCTGACGAGCAT

CACAAAAATCGACGCTCAAGTCAGAGGTGGCGAAA

CCCGACAGGACTATAAAGATACCAGGCGTTTCCCC

CTGGAAGCTCCCTCGTGCGCTCTCCTGTTCCGACC

CTGCCGCTTACCGGATACCTGTCCGCCTTTCTCCC

TTCGGGAAGCGTGGCGCTTTCTCATAGCTCACGCT

GTAGGTATCTCAGTTCGGTGTAGGTCGTTCGCTCC

AAGCTGGGCTGTGTGCACGAACCCCCCGTTCAGCC

CGACCGCTGCGCCTTATCCGGTAACTATCGTCTTG

AGTCCAACCCGGTAAGACACGACTTATCGCCACTG

GCAGCAGCCACTGGTAACAGGATTAGCAGAGCGAG

GTATGTAGGCGGTGCTACAGAGTTCTTGAAGTGGT

GGCCTAACTACGGCTACACTAGAAGGACAGTATTT

GGTATCTGCGCTCTGCTGAAGCCAGTTACCTTCGG

AAAAAGAGTTGGTAGCTCTTGATCCGGCAAACAAA

CCACCGCTGGTAGCGGTGGTTTTTTTGTTTGCAAG

CAGCAGATTACGCGCAGAAAAAAAGGATCTCAAGA

AGATCCTTTGATCTTTTCTACGGGGTCTGACGCTC

AGTGGAACGAAAACTCACGTTAAGGGATTTTGGTC

ATGAGATTATCAAAAAGGATCTTCACCTAGATCCT

TTTAAATTAAAAATGAAGTTTTAAATCAATCTAAA

GTATATATGAGTAAACTTGGTCTGACAGTTACCAA

TGCTTAATCAGTGAGGCACCTATCTCAGCGATCTG

TCTATTTCGTTCATCCATAGTTGCCTGACTCCCCG

TCGTGTAGATAACTACGATACGGGAGGGCTTACCA

TCTGGCCCCAGTGCTGCAATGATACCGCGAGACCC

ACGCTCACCGGCTCCAGATTTATCAGCAATAAACC

AGCCAGCCGGAAGGGCCGAGCGCAGAAGTGGTCCT

GCAACTTTATCCGCCTCCATCCAGTCTATTAATTG

TTGCCGGGAAGCTAGAGTAAGTAGTTCGCCAGTTA

ATAGTTTGCGCAACGTTGTTGGCATTGCTACAGGC

ATCGTGGTGTCACGCTCGTCGTTTGGTATGGCTTC

ATTCAGCTCCGGTTCCCAACGATCAAGGCGAGTTA

CATGATCCCCCATGTTGTGCAAAAAAGCGGTTAGC

TCCTTCGGTCCTCCGATCGTTGTCAGAAGTAAGTT

GGCCGCAGTGTTATCACTCATGGTTATGGCAGCAC

TGCATAATTCTCTTACTGTCATGCCATCCGTAAGA

TGCTTTTCTGTGACTGGTGAGTACTCAACCAAGTC

ATTCTGAGAATAGTGTATGCGGCGACCGAGTTGCT

CTTGCCCGGCGTCAATACGGGATAATACCGCGCCA

CATAGCAGAACTTTAAAAGTGCTCATCATTGGAAA

ACGTTCTTCGGGGCGAAAACTCTCAAGGATCTTAC
```

-continued

CGCTGTTGAGATCCAGTTCGATGTAACCCACTCGT

GCACCCAACTGATCTTCAGCATCTTTTACTTTCAC

CAGCGTTTCTGGGTGAGCAAAAACAGGAAGGCAAA

ATGCCGCAAAAAAGGGAATAAGGGCGACACGGAAA

TGTTGAATACTCATACTCTTCCTTTTTCAATATTA

TTGAAGCATTTATCAGGGTTATTGTCTCATGAGCG

GATACATATTTGAATGTATTTAGAAAAATAAACAA

ATAGGGGTTCCGCGCACATTTCCCCGAAAAGTGCC

ACCTGACGTCTAAGAAACCATTATTATCATGACAT

TAACCTATAAAAATAGGCGTATCACGAGGCCCTTT

CGTCTCGCGCGTTTCGGTGATGACGGTGAAAACCT

CTGACACATGCAGCTCCCGGAGACGGTCACAGCTT

GTCTGTAAGCGGATGCCGGGAGCAGACAAGCCCGT

CAGGGCGCGTCAGCGGGTGTTGGCGGGTGTCGGGG

CTGGCTTAACTATGCGGCATCAGAGCAGATTGTAC

TGAGAGTGCACCATATGCGGTGTGAAATACCGCAC

AGATGCGTAAGGAGAAAATACCGCATCAGGCGCCA

TTCGCCATTCAGGCTGCGCAACTGTTGGGAAGGGC

GATCGGTGCGGGCCTCTTCGCTATTACGCCAGCTG

GCGAAAGGGGGATGTGCTGCAAGGCGATTAAGTTG

GGTAACGCCAGGGTTTTCCCAGTCACGACGTTGTA

AAACGACGGCCAGTGAATTGGATTTAGGTGACACT

ATA

TABLE 6

Zaire Ebola Glycoprotein mutation table

| Changes (Silent mutation) | Mutation position on GP |
|---|---|
| T to C | 57 |
| A to G | 252 |
| A to G | 342 |
| T to C | 477 |
| A to G | 570 |
| T to C | 579 |
| A to G | 795 |
| T to C | 870 |
| A to G | 882 |
|  | 885 |
| A to G | 900 |
| A to G | 948 |
| A to G | 1143 |
| T to C | 1716 |
| T to C | 1776 |
| A to G | 1851 |

*Shown as lower case in SEQ ID NO: 11

SEQ ID 11:
pGEO-ZEBOV2014 GP sequence optimized
for insertion into MVA vector:
(FIG. 2)
GAATTCCCTGGGACATACGTATATTTCTATGATCT

GTCTTATATGAAGTCTATACAGCGAATAGATTCAG

AATTTCTACATAATTATATATTGTACGCTAATAAG

TTTAATCTAACACTCCCCGAAGATTGTTTATAAT

CCCTACAAATTTGGATATTCTATGGCGTACAAAGG

AATATATAGACTCGTTCGATATTAGTACAGAAACA

TGGAATAAATTATTATCCAATTATTATATGAAGAT

GATAGAGTATGCTAAACTTTATGTACTAAGTCCTA

TTCTCGCTGAGGAGTTGGATAATTTTGAGAGGACG

GGAGAATTAACTAGTATTGTACAAGAAGCCATTTT

ATCTCTAAATTTACGAATTAAGATTTTAAATTTTA

AACATAAAGATGATGATACGTATATACACTTTTGT

AAAATATTATTCGGTGTCTATAACGGAACAAACGC

TACTATATATTATCATAGACCTCTAACGGGATATA

TGAATATGATTTCAGATACTATATTTGTTCCTGTA

GATAATAACTAAGGCGCGCCTTTCATTTTGTTTTT

TTCTATGCTATAAATGGTGAGCAAGGGCGAGGAGC

TGTTCACCGGGGTGGTGCCCATCCTGGTCGAGCTG

GACGGCGACGTAAACGGCCACAAGTTCAGCGTGTC

CGGCGAGGGCGAGGGCGATGCCACCTACGGCAAGC

TGACCCTGAAGTTCATCTGCACCACCGGCAAGCTG

CCCGTGCCCTGGCCCACCCTCGTGACCACCCTGAC

CTACGGCGTGCAGTGCTTCAGCCGCTACCCCGACC

ACATGAAGCAGCACGACTTCTTCAAGTCCGCCATG

CCCGAAGGCTACGTCCAGGAGCGCACCATCTTCTT

CAAGGACGACGGCAACTACAAGACCCGCGCCGAGG

TGAAGTTCGAGGGCGACACCCTGGTGAACCGCATC

GAGCTGAAGGGCATCGACTTCAAGGAGGACGGCAA

CATCCTGGGGCACAAGCTGGAGTACAACTACAACA

GCCACAACGTCTATATCATGGCCGACAAGCAGAAG

AACGGCATCAAGGTGAACTTCAAGATCCGCCACAA

CATCGAGGACGGCAGCGTGCAGCTCGCCGACCACT

ACCAGCAGAACACCCCCATCGGCGACGGCCCCGTG

CTGCTGCCCGACAACCACTACCTGAGCACCCAGTC

CGCCCTGAGCAAAGACCCCAACGAGAAGCGCGATC

ACATGGTCCTGCTGGAGTTCGTGACCGCCGCCGGG

ATCACTCTCGGCATGCACGAGCTGTACAAGTAAGA

GCTCGAGGACGGGAGAATTAACTAGTATTGTACAA

GAAGCCATTTTATCTCTAAATTTACGAATTAAGAT

```
TTTAAATTTTAAACATAAAGATGATGATACGTATA
TACACTTTTGTAAAATATTATTCGGTGTCTATAAC
GGAACAAACGCTACTATATATTATCATAGACCTCT
AACGGGATATATGAATATGATTTCAGATACTATAT
TTGTTCCTGTAGATAATAACTAACTCGAGGCCGCT
GGTACCCAACCTAAAAATTGAAAATAAATACAAAG
GTTCTTGAGGGTTGTGTTAAATTGAAAGCGAGAAA
TAATCATAAATAAGCCCgggATGGGAGTAACTGGA
ATTCTACAACTACCAAGAGATAGATTCAAAAGAAC
ATCTTTcTTTCTATGGGTTATAATTCTATTTCAAA
GAACATTTTCTATTCCATTGGGAGTAATTCATAAT
TCTACATTGCAAGTATCTGATGTAGATAAACTAGT
ATGTAGAGATAAATTGTCTAGTACAAATCAACTAA
GATCTGTAGGATTGAATCTAGAAGGAAATGGTGTA
GCGACAGATGTTCCATCTGTAACAAAgAGATGGGG
TTTTAGATCTGGTGTACCACCAAAAGTAGTAAATT
ATGAAGCGGGAGAATGGGCGGAAAATTGTTATAAT
CTAGAAATTAAgAAACCAGATGGATCTGAATGTCT
ACCAGCGGCGCCAGATGGAATTAGAGGATTTCCAA
GATGTAGATATGTTCATAAAGTATCTGGAACAGGA
CCATGTGCGGGAGATTTTGCGTTTCATAAAGAAGG
AGCATTcTTTCTATATGATAGACTAGCGTCTACAG
TAATATATAGAGGAACAACATTTGCGGAAGGTGTA
GTAGCTTTTCTAATTCTACCACAAGCGAAgAAAGA
TTTcTTTAGTTCTCATCCACTAAGAGAACCAGTAA
ATGCGACAGAAGATCCTTCTTCTGGATATTATTCT
ACTACAATTAGATATCAAGCGACAGGATTTGGAAC
AAATGAAACAGAATATCTATTTGAAGTTGATAATC
TAACATATGTACAACTAGAAAGTAGATTCACACCA
CAATTTCTATTGCAATTGAATGAAACAATATATGC
GTCTGGAAAgAGATCTAATACAACTGGAAAACTAA
TTTGGAAAGTAAATCCAGAAATTGATACAACAATT
GGAGAATGGGCTTTcTGGGAAACAAAgAAgAATTT
GACAAGAAAgATTAGATCTGAAGAATTGTCTTTTA
CAGCGGTATCTAATGGACCAAAgAATATTTCTGGA
CAATCTCCAGCGAGAACTTCTTCTGATCCAGAAAC
AAATACTACAAATGAAGATCACAAAATTATGGCGT
CTGAAAATTCTTCTGCTATGGTACAAGTACATTCT
CAAGGAAGAAAAGCGGCGGTATCTCATCTAACAAC
ACTAGCGACTATTTCTACATCTCCACAACCACCAA
```

```
CAACAAAgACTGGACCAGATAATAGTACACATAAT
ACTCCAGTTTATAAACTAGATATTTCTGAAGCGAC
ACAAGTTGGACAACATCATAGAAGAGCGGATAATG
ATTCTACAGCGTCTGATACACCACCAGCTACAACA
GCTGCTGGACCATTGAAAGCGGAAAATACAAATAC
TTCTAAATCTGCGGATTCTCTAGATTTGGCGACAA
CAACTTCTCCTCAAAATTATTCTGAAACAGCGGGA
AATAATAATACTCATCATCAAGATACTGGAGAAGA
ATCTGCGTCTAGTGGAAAATTGGGACTAATTACAA
ATACAATTGCGGGTGTAGCGGGATTGATTACTGGT
GGAAGAAGAACTAGAAGAGAAGTAATAGTTAATGC
GCAACCTAAATGTAATCCAAATCTACATTATTGGA
CAACTCAAGATGAAGGTGCTGCGATTGGACTAGCT
TGGATTCCATATTTTGGACCTGCGGCGGAAGGAAT
ATATACTGAAGGACTAATGCATAATCAAGATGGAC
TAATTTGTGGACTAAGACAACTAGCGAATGAAACT
ACACAAGCGCTACAACTATTcTTGAGAGCGACAAC
AGAACTAAGAACTTTTAGTATTCTAAATAGAAAAG
CGATTGATTTcTTGCTACAAAGATGGGGAGGAACA
TGTCATATTCTAGGACCAGATTGTTGTATTGAACC
ACATGATTGGACAAAgAATATTACAGACAAAATTG
ATCAAATTATTCATGATTTTGTTGATAAAACACTA
CCAGATCAAGGAGATAATGATAATTGGTGGACAGG
ATGGAGACAATGGATTCCAGCGGGAATTGGAGTAA
CAGGTGTAATTATTGCGGTTATTGCGCTATTTTGT
ATATGTAAATTTGTTTTTTAATAATTTTTATgTCG
ACCTGCAGTCAAACTCTAATGACCACATCTTTTTT
TAGAGATGAAAAATTTTCCACATCTCCTTTTGTAG
ACACGACTAAACATTTTGCAGAAAAAAGTTTATTA
GTGTTTAGATAATCGTATACTTCATCAGTGTAGAT
AGTAAATGTGAACAGATAAAAGGTATTCTTGCTCA
ATAGATTGGTAAATTCCATAGAATATATTAATCCT
TTCTTCTTGAGATCCCACATCATTTCAACCAGAGA
CGTTTTATCCAATGATTTACCTCGTACTATACCAC
ATACAAAACTAGATTTTGCAGTGACGTCGTATCTG
GTATTCCTACCAAACAAAATTTTACTTTTAGTTCT
TTTAGAAAATTCTAAGGTAGAATCTCTATTTGCCA
ATATGTCATCTATGGAATTACCACTAGCAAAAAAT
GATAGAAATATATATTGATACATCGCAGCTGGTTT
TGATCTACTATACTTTAAAAACGAATCAGATTCCA
TAATTGCCTGTATATCATCAGCTGAAAAACTATGT
```

```
TTTACACGTATTCCTTCGGCATTTCTTTTTAATGA

TATATCTTGTTTAGACAATGATAAAGTTATCATGT

CCATGAGAGACGCGTCTCCGTATCGTATAAATATT

TCATTAGATGTTAGACGCTTCATTAGGGGTATACT

TCTATAAGGTTTCTTAATCAGTCCATCATTGGTTG

CGTCAAGAACAAGCTTGTCTCCCTATAGTGAGTCG

TATTAGAGCTTGGCGTAATCATGGTCATAGCTGTT

TCCTGTGTGAAATTGTTATCCGCTCACAATTCCAC

ACAACATACGAGCCGGAAGCATAAAGTGTAAAGCC

TGGGGTGCCTAATGAGTGAGCTAACTCACATTAAT

TGCGTTGCGCTCACTGCCCGCTTTCGAGTCGGGAA

ACCTGTCGTGCCAGCTGCATTAATGAATCGGCCAA

CGCGCGGGGAGAGGCGGTTTGCGTATTGGGCGCTC

TTCCGCTTCCTCGCTCACTGACTCGCTGCGCTCGG

TCGTTCGGCTGCGGCGAGCGGTATCAGCTCACTCA

AAGGCGGTAATACGGTTATCCACAGAATCAGGGGA

TAACGCAGGAAAGAACATGTGAGCAAAAGGCCAGC

AAAAGGCCAGGAACCGTAAAAAGGCCGCGTTGCTG

GCGTTTTTCGATAGGCTCCGCCCCCCTGACGAGCA

TCACAAAAATCGACGCTCAAGTCAGAGGTGGCGAA

ACCCGACAGGACTATAAAGATACCAGGCGTTTCCC

CCTGGAAGCTCCCTCGTGCGCTCTCCTGTTCCGAC

CCTGCCGCTTACCGGATACCTGTCCGCCTTTCTCC

CTTCGGGAAGCGTGGCGCTTTCTCATAGCTCACGC

TGTAGGTATCTCAGTTCGGTGTAGGTCGTTCGCTC

CAAGCTGGGCTGTGTGCACGAACCCCCCGTTCAGC

CCGACCGCTGCGCCTTATCCGGTAACTATCGTCTT

GAGTCCAACCCGGTAAGACACGACTTATCGCCACT

GGCAGCAGCCACTGGTAACAGGATTAGCAGAGCGA

GGTATGTAGGCGGTGCTACAGAGTTCTTGAAGTGG

TGGCCTAACTACGGCTACACTAGAAGGACAGTATT

TGGTATCTGCGCTCTGCTGAAGCCAGTTACCTTCG

GAAAAAGAGTTGGTAGCTCTTGATCCGGCAAACAA

ACCACCGCTGGTAGCGGTGGTTTTTTTGTTTGCAA

GCAGCAGATTACGCGCAGAAAAAAAGGATCTCAAG

AAGATCCTTTGATCTTTTCTACGGGGTCTGACGCT

CAGTGGAACGAAAACTCACGTTAAGGGATTTTGGT

CATGAGATTATCAAAAAGGATCTTCACCTAGATCC

TTTTAAATTAAAAATGAAGTTTTAAATCAATCTAA

AGTATATATGAGTAAACTTGGTCTGACAGTTACCA

ATGCTTAATCAGTGAGGCACCTATCTCAGCGATCT

GTCTATTTCGTTCATCCATAGTTGCCTGACTCCCC

GTCGTGTAGATAACTACGATACGGGAGGGCTTACC

ATCTGGCCCCAGTGCTGCAATGATACCGCGAGACC

CACGCTCACCGGCTCCAGATTTATCAGCAATAAAC

CAGCCAGCCGGAAGGGCCGAGCGCAGAAGTGGTCC

TGCAACTTTATCCGCCTCCATCCAGTCTATTAATT

GTTGCCGGGAAGCTAGAGTAAGTAGTTCGCCAGTT

AATAGTTTGCGCAACGTTGTTGGCATTGCTACAGG

CATCGTGGTGTCACGCTCGTCGTTTGGTATGGCTT

CATTCAGCTCCGGTTCCCAACGATCAAGGCGAGTT

ACATGATCCCCCATGTTGTGCAAAAAAGCGGTTAG

CTCCTTCGGTCCTCCGATCGTTGTCAGAAGTAAGT

TGGCCGCAGTGTTATCACTCATGGTTATGGCAGCA

CTGCATAATTCTCTTACTGTCATGCCATCCGTAAG

ATGCTTTTCTGTGACTGGTGAGTACTCAACCAAGT

CATTCTGAGAATAGTGTATGCGGCGACCGAGTTGC

TCTTGCCCGGCGTCAATACGGGATAATACCGCGCC

ACATAGCAGAACTTTAAAAGTGCTCATCATTGGAA

AACGTTCTTCGGGGCGAAAACTCTCAAGGATCTTA

CCGCTGTTGAGATCCAGTTCGATGTAACCCACTCG

TGCACCCAACTGATCTTCAGCATCTTTTACTTTCA

CCAGCGTTTCTGGGTGAGCAAAAACAGGAAGGCAA

AATGCCGCAAAAAAGGGAATAAGGGCGACACGGAA

ATGTTGAATACTCATACTCTTCCTTTTTCAATATT

ATTGAAGCATTTATCAGGGTTATTGTCTCATGAGC

GGATACATATTTGAATGTATTTAGAAAAATAAACA

AATAGGGGTTCCGCGCACATTTCCCCGAAAAGTGC

CACCTGACGTCTAAGAAACCATTATTATCATGACA

TTAACCTATAAAAATAGGCGTATCACGAGGCCCTT

TCGTCTCGCGCGTTTCGGTGATGACGGTGAAAACC

TCTGACACATGCAGCTCCCGGAGACGGTCACAGCT

TGTCTGTAAGCGGATGCCGGGAGCAGACAAGCCCG

TCAGGGCGCGTCAGCGGGTGTTGGCGGGTGTCGGG

GCTGGCTTAACTATGCGGCATCAGAGCAGATTGTA
```

-continued

CTGAGAGTGCACCATATGCGGTGTGAAATACCGCA

CAGATGCGTAAGGAGAAAATACCGCATCAGGCGCC

ATTCGCCATTCAGGCTGCGCAACTGTTGGGAAGGG

CGATCGGTGCGGGCCTCTTCGCTATTACGCCAGCT

GGCGAAAGGGGGATGTGCTGCAAGGCGATTAAGTT

GGGTAACGCCAGGGTTTTCCCAGTCACGACGTTGT

AAAACGACGGCCAGTGAATTGGATTTAGGTGACAC

TATA

TABLE 7

Sudan Ebola VP40 mutation table

| Changes (Silent mutation) | Mutation position on VP40 |
|---|---|
| A to G | 111 |
| A to G | 312 |
| A to G | 663 |
| A to G | 675 |
| A to G | 822 |
| A to G | 837 |
| A to G | 978 |

*Shown as lower case in SEQ ID NO: 12

```
SEQ ID 12:
pGEO-SUDV2014 VP40 sequence optimized for insertion into MVA vector: (FIG. 7)
GAATTCGGAGTATACGAACCGGGAAAGAGAAGATGGTTAAAAATAAAGCGAGACTATTTGAACGAGGGTTCCATGGC

AGATTCTGCCGATTTAGTAGTACTAGGTGCTTACTATGGTAAAGGAGCAAAGGGTGGTATCATGGCAGTCTTTCTAA

TGGGTTGTTACGACGATGAATCCGGTAAATGGAAGACGGTTACCAAGTGTTCAGGACACGATGATAATACGTTAAGG

GAGTTGCAAGACCAATTAAAGATGATTAAAATTAACAAGGATCCCAAAAAAATTCCAGAGTGGTTAGTAGTTAATAA

AATCTATATTCCCGATTTTGTAGTAGAGGATCCAAAACAATCTCAGATATGGGAAATTTCAGGAGCAGAGTTTACAT

CTTCCAAGTCCCATACCGCAAATGGAATATCCATTAGATTTCCTAGATTTACTAGGATAAGAGAGGATAAAACGTGG

AAAGAATCTACTCATCTAAACGATTTAGTAAACTTGACTAAATCTTAATTTTTATGGCGCGCCTTTCATTTTGTTTT

TTTCTATGCTATAAATGGTGAGCAAGGGCGAGGAGCTGTTCACCGGGGTGGTGCCCATCCTGGTCGAGCTGGACGGC

GACGTAAACGGCCACAAGTTCAGCGTGTCCGGCGAGGGCGAGGGCGATGCCACCTACGGCAAGCTGACCCTGAAGTT

CATCTGCACCACCGGCAAGCTGCCCGTGCCCTGGCCCACCCTCGTGACCACCCTGACCTACGGCGTGCAGTGCTTCA

GCCGCTACCCCGACCACATGAAGCAGCACGACTTCTTCAAGTCCGCCATGCCCGAAGGCTACGTCCAGGAGCGCACC

ATCTTCTTCAAGGACGACGGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGTACAACTACAACAGCCACA

ACGTCTATATCATGGCCGACAAGCAGAAGAACGGCATCAAGGTGAACTTCAAGATCCGCCACAACATCGAGGACGGC

AGCGTGCAGCTCGCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGGAGTTCGTGACCG

CCGCCGGGATCACTCTCGGCATGCACGAGCTGTACAAGTAAGAGCTCCCCGATTTTGTAGTAGAGGATCCAAAACAA

TCTCAGATATGGGAAATTTCAGGAGCAGAGTTTACATCTTCCAAGTCCCATACCGCAAATGGAATATCCATTAGATT

TCCTAGATTTACTAGGATAAGAGAGGATAAAACGTGGAAAGAATCTACTCATCTAAACGATTTAGTAAACTTGACTA

AATCTTAATTTTTATCTCGAGGCCGCTGGTACCCAACCTAAAAATTGAAAATAAATACAAAGGTTCTTGAGGGTTGT

GTTAAATTGAAAGCGAGAAATAATCATAAATAAGCCCgggATGAAAAGAGTAACAGTACCAACAGCGCCACCAGCGT

ATGCGGATATAGGATATCCAATGTCTATGCTACCTATTAAATCTTCTAGAGCGGTATCTGGAATTCAACAAAAgCAA

GAAGTACTACCTGGAATGGATACACCATCTAATTCTATGAGACCAGTAGCGGATGATAATATTGATCATACTTCTCA

TACTCCAAATGGTGTAGCGTCTGCTTTTATTCTAGAAGCGACAGTAAATGTAATTTCTGGACCAAAAGTACTAATGA

ACAAATTCCAATTTGGCTACCACTAGGAATTGCGGATCAAAAgACATATTCTTTTGATTCTACAACAGCGGCGATT

ATGCTAGCGTCTTATACAATTACACATTTTGGAAAAGCGAATAATCCACTAGTTAGAGTAAATAGACTAGGACAAGG

AATACCAGATCATCCACTAAGACTACTAAGAATGGGAAATCAAGCTTTTCTACAAGAATTTGTTCTACCACCAGTAC

AACTACCACAATACTTTACATTTGATCTAACAGCGCTAAAACTAGTAACACAACCACTACCAGCGGCGACATGGACA

GATGAAACTCCATCTAATCTAAGTGGTGCTCTAAGACCAGGACTATCTTTTCATCCAAAACTAAGACCTGTACTACT

ACCAGGAAAgACTGGAAAgAAAGGACATGTATCTGATTTGACAGCGCCAGACAAAATTCAAACAATAGTAAATCTAA
```

-continued

```
TGCAAGACTTCAAAATTGTACCAATTGATCCAGCGAAATCTATTATTGGAATTGAAGTACCAGAACTACTAGTTCAT

AAATTGACTGGAAAgAAAATGTCTCAAAAgAATGGACAACCTATTATTCCAGTACTATTGCCTAAATATATTGGTCT

AGATCCTATTTCTCCTGGAGATCTAACAATGGTTATTACACCAGATTATGATGATTGTCATTCTCCAGCGTCTTGTT

CTTATCTATCTGAAAAgTAAtaagTCGACCTGCAGCTAATGTATTAGTTAAATATTAAAACTTACCACGTAAAACTT

AAAATTTAAAATGATATTTCATTGACAGATAGATCACACATTATGAACTTTCAAGGACTTGTGTTAACTGACAATTG

CAAAAATCAATGGGTCGTTGGACCATTAATAGGAAAAGGTGGATTTGGTAGTATTTATACTACTAATGACAATAATT

ATGTAGTAAAAATAGAGCCCAAAGCTAACGGATCATTATTTACCGAACAGGCATTTTATACTAGAGTACTTAAACCA

TCCGTTATCGAAGAATGGAAAAAATCTCACAATATAAAGCACGTAGGTCTTATCACGTGCAAGGCATTTGGTCTATA

CAAATCCATTAATGTGGAATATCGATTCTTGGTAATTAATAGATTAGGTGCAGATCTAGATGCGGTGATCAGAGCCA

ATAATAATAGATTACCAAAAAGGTCGGTGATGTTGATCGGAATCGAAATCTTAAATACCATACAATTTATGCACGAG

CAAGGATATTCTCACGGAGATATTAAAGCGAGTAATATAGTCTTGGATCAAATAGATAAGAATAAATTATATCTAGT

GGATTACGGATTGGTTTCTAAATTCATGTCAAGCTTGTCTCCCTATAGTGAGTCGTATTAGAGCTTGGCGTAATCAT

GGTCATAGCTGTTTCCTGTGTGAAATTGTTATCCGCTCACAATTCCACACAACATACGAGCCGGAAGCATAAAGTGT

AAAGCCTGGGGTGCCTAATGAGTGAGCTAACTCACATTAATTGCGTTGCGCTCACTGCCCGCTTTCGAGTCGGGAAA

CCTGTCGTGCCAGCTGCATTAATGAATCGGCCAACGCGCGGGGAGAGGCGGTTTGCGTATTGGGCGCTCTTCCGCTT

CCTCGCTCACTGACTCGCTGCGCTCGGTCGTTCGGCTGCGGCGAGCGGTATCAGCTCACTCAAAGGCGGTAATACGG

TTATCCACAGAATCAGGGGATAACGCAGGAAAGAACATGTGAGCAAAAGGCCAGCAAAAGGCCAGGAACCGTAAAAA

GGCCGCGTTGCTGGCGTTTTTCGATAGGCTCCGCCCCCCTGACGAGCATCACAAAAATCGACGCTCAAGTCAGAGGT

GGCGAAACCCGACAGGACTATAAAGATACCAGGCGTTTCCCCCTGGAAGCTCCCTCGTGCGCTCTCCTGTTCCGACC

CTGCCGCTTACCGGATACCTGTCCGCCTTTCTCCCTTCGGGAAGCGTGGCGCTTTCTCATAGCTCACGCTGTAGGTA

TCTCAGTTCGGTGTAGGTCGTTCGCTCCAAGCTGGGCTGTGTGCACGAACCCCCCGTTCAGCCCGACCGCTGCGCCT

TATCCGGTAACTATCGTCTTGAGTCCAACCCGGTAAGACACGACTTATCGCCACTGGCAGCAGCCACTGGTAACAGG

ATTAGCAGAGCGAGGTATGTAGGCGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGCAGAAAAAAAGGATCTCAAGAAGATCCT

TTGATCTTTTCTACGGGGTCTGACGCTCAGTGGAACGAAAACTCACGTTAAGGGATTTTGGTCATGAGATTATCAAA

AAGGATCTTCACCTAGATCCTTTTAAATTAAAAATGAAGTTTTAAATCAATCTAAAGTATATATGAGTAAACTTGGT

CTGACAGTTACCAATGCTTAATCAGTGAGGCACCTATCTCAGCGATCTGTCTATTTCGTTCATCCATAGTTGCCTGA

CTCCCCGTCGTGTAGATAACTACGATACGGGAGGGCTTACCATCTGGCCCCAGTGCTGCAATGATACCGCGAGACCC

ACGCTCACCGGCTCCAGATTTATCAGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTTCGCCAGTTAATAGTTTGCGCAAC

GTTGTTGGCATTGCTACAGGCATCGTGGTGTCACGCTCGTCGTTTGGTATGGCTTCATTCAGCTCCGGTTCCCAACG

ATCAAGGCGAGTTACATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCATGCCATCCGTAAGA

TGCTTTTCTGTGACTGGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAAAACGTTCTTCGGGGC

GAAAACTCTCAAGGATCTTACCGCTGTTGAGATCCAGTTCGATGTAACCCACTCGTGCACCCAACTGATCTTCAGCA

TCTTTTACTTTCACCAGCGTTTCTGGGTGAGCAAAAACAGGAAGGCAAAATGCCGCAAAAAAGGGAATAAGGGCGAC

ACGGAAATGTTGAATACTCATACTCTTCCTTTTTCAATATTATTGAAGCATTTATCAGGGTTATTGTCTCATGAGCG

GATACATATTTGAATGTATTTAGAAAAATAAACAAATAGGGGTTCCGCGCACATTTCCCCGAAAAGTGCCACCTGAC
```

-continued

```
GTCTAAGAAACCATTATTATCATGACATTAACCTATAAAAATAGGCGTATCACGAGGCCCTTTCGTCTCGCGCGTTT
CGGTGATGACGGTGAAAACCTCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCTGGCTTAACTATGCGGCATCAGAGCAG
ATTGTACTGAGAGTGCACCCATATGCGGTGTGAAATACCGCACAGATGCGTAAGGAGAAAATACCGCATCAGGCGCCA
TTCGCCATTCAGGCTGCGCAACTGTTGGGAAGGGCGATCGGTGCGGGCCTCTTCGCTATTACGCCAGCTGGCGAAAG
GGGGATGTGCTGCAAGGCGATTAAGTTGGGTAACGCCAGGGTTTTCCCAGTCACGACGTTGTAAAACGACGGCCAGT
GAATTGGATTTAGGTGACACTATA
```

TABLE 8

Sudan Ebola Glycoprotein mutation table

| Changes (Silent mutation) | Mutation position on GP |
| --- | --- |
| T to C | 57 |
| A to G | 87 |
| T to C | 93 |
| A to G | 252 |
| A to G | 342 |
| T to C | 477 |
| A to G | 882, 885 |
| A to G | 1035 |
| A to G | 1407 |
| A to G | 1491 |
| T to C | 1776 |
| A to G | 1851 |

*Shown as lower case in SEQ ID NO: 13

SEQ ID 13:
pGEO-SUDV2014 GP sequence optimized for insertion into MVA vector: (FIG. 8)

```
GAATTCCCTGGGACATACGTATATTTCTATGATCTGTCTTATATGAAGTCTATACAGCGAATAGATTCAGAATTT
CTACATAATTATATATTGTACGCTAATAAGTTTAATCTAACACTCCCCGAAGATTTGTTTATAATCCCTACAAAT
TTGGATATTCTATGGCGTACAAAGGAATATATAGACTCGTTCGATATTAGTACAGAAACATGGAATAAATTATTA
TCCAATTATTATATGAAGATGATAGAGTATGCTAAACTTTATGTACTAAGTCCTATTCTCGCTGAGGAGTTGGAT
AATTTTGAGAGGACGGGAGAATTAACTAGTATTGTACAAGAAGCCATTTTATCTCTAAATTTACGAATTAAGATT
TTAAATTTTAAACATAAAGATGATGATACGTATATACACTTTTGTAAAATATTATTCGGTGTCTATAACGGAACA
AACGCTACTATATATTATCATAGACCTCTAACGGGATATATGAATATGATTTCAGATACTATATTTGTTCCTGTA
GATAATAACTAAGGCGCGCCTTTCATTTTGTTTTTTTCTATGCTATAAATGGTGAGCAAGGGCGAGGAGCTGTTC
ACCGGGGTGGTGCCCATCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATGAAGCAGCACGACTTC
TTCAAGTCCGCCATGCCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCATGGCCGACAAGCAGAAG
AACGGCATCAAGGTGAACTTCAAGATCCGCCACAACATCGAGGACGGCAGCGTGCAGCTCGCCGACCACTACCAG
CAGAACACCCCCATCGGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGGATCACTCTCGGCATG
CACGAGCTGTACAAGTAAGAGCTCGAGGACGGGAGAATTAACTAGTATTGTACAAGAAGCCATTTTATCTCTAAA
TTTACGAATTAAGATTTTAAATTTTAAACATAAAGATGATGATACGTATATACACTTTTGTAAAATATTATTCGG
TGTCTATAACGGAACAAACGCTACTATATATTATCATAGACCTCTAACGGGATATATGAATATGATTTCAGATAC
TATATTTGTTCCTGTAGATAATAACTAACTCGAGGCCGCTGGTACCCAACCTAAAAATTGAAAATAAATACAAAG
GTTCTTGAGGGTTGTGTTAAATTGAAAGCGAGAAATAATCATAAATAAGCCCgggATGGGAGGACTATCTCTACT
ACAACTACCAAGAGATAAGTTTAGAAAATCTTCTTTcTTTGTTTGGGTTATAATTCTATTTCAAAgGCGTTcTC
```

-continued

```
TATGCCATTGGGAGTAGTAACAAATTCTACACTAGAAGTAACAGAAATTGATCAACTAGTATGTAAAGATCATCT

AGCGTCTACAGATCAATTGAAATCTGTTGGATTGAATCTAGAAGGATCTGGTGTATCTACAGATATTCCATCTGC

GACAAAgAGATGGGGTTTTAGAAGTGGTGTACCACCAAAAGTAGTATCTTATGAAGCGGGAGAATGGGCGGAAAA

TTGTTATAATCTAGAAATTAAgAAACCAGATGGATCTGAATGTTTGCCACCACCACCAGATGGTGTTAGAGGATT

TCCAAGATGTAGATATGTTCATAAAGCGCAAGGAACAGGACCATGTCCTGGAGATTATGCGTTTCATAAAGATGG

TGCATTcTTTCTATATGATAGATTGGCGTCTACTGTAATATATAGAGGTGTAAATTTTGCGGAAGGTGTAATTGC

TTTTCTAATTCTAGCGAAACCTAAAGAAACATTTCTACAATCTCCACCAATTAGAGAAGCGGTTAATTATACAGA

AAATACTTCATCTTATTATGCGACATCTTATCTAGAATATGAAATTGAAAATTTTGGAGCGCAACATTCTACAAC

TTTGTTCAAAATTGATAATAATACTTTTGTTAGACTAGATAGACCACATACACCACAATTTTTGTTTCAATTGAA

TGATACAATTCATCTACATCAACAACTATCTAATACAACTGGAAGATTGATTTGGACACTAGATGCGAATATTAA

TGCGGATATTGGAGAATGGGCTTTcTGGGAAAATAAgAAgAATCTATCTGAACAACTAAGAGGAGAAGAATTGTC

TTTTGAAGCGCTATCTCTAAATGAAACTGAAGATGATGATGCGGCGTCTAGTAGAATTACAAAAGGAAGAATTTC

TGATAGAGCGACAAGACAATATTCTGATCTAGTACCAAAgAATCCACCTGGAATGGTTCCATTGCATATTCCAGA

AGGAGAAACAACACTACCATCTCAAAATTCTACTGAAGGAAGAAGAGTATCTGTAAATACTCAAGAAACAATTAC

AGAAACAGCGGCGACAATTATTGGAACAAATGGAAATCATATGCAAATTTCTACTATTGGAATTAGACCATCTTC

TTCTCAAATTCCATCTTCTAGTCCAACAACAGCGCCATCTCCAGAAGCGCAAACACCAACAACACATACAAGTGG

ACCATCTGTAATGGCGACAGAAGAACCTACAACACCACCAGGATCTTCTCCAGGTCCAACTACAGAAGCGCCAAC

TCTAACTACACCAGAAAATATTACAACAGCTGTAAAgACAGTACTACCACAAGAATCTACTTCTAATGGACTAAT

TACATCTACAGTAACTGGAATTCTAGGATCTCTAGGACTAAGAAAgAGATCTAGAAGACAAACAAATACAAAAGC

GACTGGAAAATGTAATCCAAATCTACATTATTGGACAGCGCAAGAACAACATAATGCGGCGGGAATTGCTTGGAT

TCCATATTTTGGACCAGGTGCTGAAGGAATATATACTGAAGGTCTAATGCATAATCAAAATGCGCTAGTATGTGG

ACTAAGACAACTAGCGAATGAAACAACTCAAGCGCTACAACTATTTCTAAGAGCGACTACAGAACTAAGAACATA

TACAATTCTAAATAGAAAAGCTATTGATTTcTTGTTGAGAAGATGGGGAGGAACATGTAGAATATTGGGACCAGA

TTGTTGTATTGAACCACATGATTGGACAAAgAATATTACTGACAAAATTAATCAAATTATTCATGACTTTATTGA

TAATCCACTACCAAATCAAGATAATGATGATAATTGGTGGACAGGATGGAGACAATGGATTCCAGCGGGAATAGG

AATTACTGGAATTATTATTGCGATTATAGCGCTACTATGTGTATGTAAACTACTATGTTAATAAgTCGACCTGCA

GTCAAACTCTAATGACCACATCTTTTTTTAGAGATGAAAAATTTTCCACATCTCCTTTTGTAGACACGACTAAAC

ATTTTGCAGAAAAAAGTTTATTAGTGTTTAGATAATCGTATACTTCATCAGTGTAGATAGTAAATGTGAACAGAT

AAAAGGTATTCTTGCTCAATAGATTGGTAAATTCCATAGAATATATTAATCCTTTCTTCTTGAGATCCCACATCA

TTTCAACCAGAGACGTTTTATCCAATGATTTACCTCGTACTATACCACATACAAAACTAGATTTTGCAGTGACGT

CGTATCTGGTATTCCTACCAAACAAAATTTTACTTTTAGTTCTTTTAGAAAATTCTAAGGTAGAATCTCTATTTG

CCAATATGTCATCTATGGAATTACCACTAGCAAAAAATGATAGAAATATATATTGATACATCGCAGCTGGTTTTG

ATCTACTATACTTTAAAAACGAATCAGATTCCATAATTGCCTGTATATCATCAGCTGAAAAACTATGTTTTACAC

GTATTCCTTCGGCATTTCTTTTTAATGATATATCTTGTTTAGACAATGATAAAGTTATCATGTCCATGAGAGACG

CGTCTCCGTATCGTATAAATATTTCATTAGATGTTAGACGCTTCATTAGGGGTATACTTCTATAAGGTTTCTTAA

TCAGTCCATCATTGGTTGCGTCAAGAACAAGCTTGTCTCCCTATAGTGAGTCGTATTAGAGCTTGGCGTAATCAT
```

-continued

```
GGTCATAGCTGTTTCCTGTGTGAAATTGTTATCCGCTCACAATTCCACACAACATACGAGCCGGAAGCATAAAGT

GTAAAGCCTGGGGTGCCTAATGAGTGAGCTAACTCACATTAATTGCGTTGCGCTCACTGCCCGCTTTCGAGTCGG

GAAACCTGTCGTGCCAGCTGCATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGTATCAGCTCACTCAAAGGCGG

TAATACGGTTATCCACAGAATCAGGGGATAACGCAGGAAAGAACATGTGAGCAAAAGGCCAGCAAAAGGCCAGGA

ACCGTAAAAAGGCCGCGTTGCTGGCGTTTTTCGATAGGCTCCGCCCCCCTGACGAGCATCACAAAAATCGACGCT

CAAGTCAGAGGTGGCGAAACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGACACGACTTATCGCCACTGG

CAGCAGCCACTGGTAACAGGATTAGCAGAGCGAGGTATGTAGGCGGTGCTACAGAGTTCTTGAAGTGGTGGCCTA

ACTACGGCTACACTAGAAGGACAGTATTTGGTATCTGCGCTCTGCTGAAGCCAGTTACCTTCGGAAAAAGAGTTG

GTAGCTCTTGATCCGGCAAACAAACCACCGCTGGTAGCGGTGGTTTTTTTGTTTGCAAGCAGCAGATTACGCGCA

GAAAAAAGGATCTCAAGAAGATCCTTTGATCTTTTCTACGGGGTCTGACGCTCAGTGGAACGAAAACTCACGTT

AAGGGATTTTGGTCATGAGATTATCAAAAAGGATCTTCACCTAGATCCTTTTAAATTAAAAATGAAGTTTTAAAT

CAATCTAAAGTATATATGAGTAAACTTGGTCTGACAGTTACCAATGCTTAATCAGTGAGGCACCTATCTCAGCGA

TCTGTCTATTTCGTTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGTCTATTAATTGTTGCCGGGAAG

CTAGAGTAAGTAGTTCGCCAGTTAATAGTTTGCGCAACGTTGTTGGCATTGCTACAGGCATCGTGGTGTCACGCT

CGTCGTTTGGTATGGCTTCATTCAGCTCCGGTTCCCAACGATCAAGGCGAGTTACATGATCCCCCATGTTGTGCA

AAAAAGCGGTTAGCTCCTTCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAATACGGGATAATACCGCGCCAC

ATAGCAGAACTTTAAAAGTGCTCATCATTGGAAAACGTTCTTCGGGGCGAAAACTCTCAAGGATCTTACCGCTGT

TGAGATCCAGTTCGATGTAACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATATTTGAATGTATTT

AGAAAAATAAACAAATAGGGGTTCCGCGCACATTTCCCCGAAAAGTGCCACCTGACGTCTAAGAAACCATTATTA

TCATGACATTAACCTATAAAAATAGGCGTATCACGAGGCCCTTTCGTCTCGCGCGTTTCGGTGATGACGGTGAAA

ACCTCTGACACATGCAGCTCCCGGAGACGGTCACAGCTTGTCTGTAAGCGGATGCCGGGAGCAGACAAGCCCGTC

AGGGCGCGTCAGCGGGTGTTGGCGGGTGTCGGGCTGGCTTAACTATGCGGCATCAGAGCAGATTGTACTGAGAG

TGCACCATATGCGGTGTGAAATACCGCACAGATGCGTAAGGAGAAAATACCGCATCAGGCGCCATTCGCCATTCA

GGCTGCGCAACTGTTGGGAAGGGCGATCGGTGCGGGCCTCTTCGCTATTACGCCAGCTGGCGAAAGGGGGATGTG

CTGCAAGGCGATTAAGTTGGGTAACGCCAGGGTTTTCCCAGTCACGACGTTGTAAAACGACGGCCAGTGAATTGG

ATTTAGGTGACACTATA
```

Example 4: MVA Vaccine Incorporating Marburg Virus Sequences

In an exemplary embodiment, sequences from Marburg virus (MARV) are prepared and optimized in shuttle plasmids and then the viral sequences are incorporated into an MVA vector. Such MVA vectors may be used individually as part of an administration protocol to elicit an immune response to Marburg virus or as part of a multivalent vaccine composition having one or more MVA vectors expressing EBOV and Marburg antigens to elicit an immune response.

TABLE 9

Marburg VP40 mutation table

| Changes (Silent mutation) | Mutation position on VP40 |
| --- | --- |
| A to G | 357 |
| T to C | 465 |
| A to G | 519 |
| A to G | 630 |
| A to G | 654 |
| A to G | 717 |
| A to G | 729 |
| A to G | 792 |

*Shown as lower case in SEQ ID NO: 14

Exemplary Marburg VP40 and GP sequences are provided below.

```
SEQ ID 14:
pGEO-MARV2014 VP40 sequence optimized for insertion into MVA vector: (FIG. 9)
GAATTCGGAGTATACGAACCGGGAAAGAGAAGATGGTTAAAAATAAAGCGAGACTATTTGAACGAGGGTTCCATGGC

AGATTCTGCCGATTTAGTAGTACTAGGTGCTTACTATGGTAAAGGAGCAAAGGGTGGTATCATGGCAGTCTTTCTAA

TGGGTTGTTACGACGATGAATCCGGTAAATGGAAGACGGTTACCAAGTGTTCAGGACACGATGATAATACGTTAAGG

GAGTTGCAAGACCAATTAAAGATGATTAAAATTAACAAGGATCCCAAAAAAATTCCAGAGTGGTTAGTAGTTAATAA

AATCTATATTCCCGATTTTGTAGTAGAGGATCCAAAACAATCTCAGATATGGGAAATTTCAGGAGCAGAGTTTACAT

CTTCCAAGTCCCATACCGCAAATGGAATATCCATTAGATTTCCTAGATTTACTAGGATAAGAGAGGATAAAACGTGG

AAAGAATCTACTCATCTAAACGATTTAGTAAACTTGACTAAATCTTAATTTTTATGGCGCGCCTTTCATTTTGTTTT

TTTCTATGCTATAAATGGTGAGCAAGGGCGAGGAGCTGTTCACCGGGGTGGTGCCCATCCTGGTCGAGCTGGACGGC

GACGTAAACGGCCACAAGTTCAGCGTGTCCGGCGAGGGCGAGGGCGATGCCACCTACGGCAAGCTGACCCTGAAGTT

CATCTGCACCACCGGCAAGCTGCCCGTGCCCTGGCCCACCCTCGTGACCACCCTGACCTACGGCGTGCAGTGCTTCA

GCCGCTACCCCGACCACATGAAGCAGCACGACTTCTTCAAGTCCGCCATGCCCGAAGGCTACGTCCAGGAGCGCACC

ATCTTCTTCAAGGACGACGGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGTACAACTACAACAGCCACA

ACGTCTATATCATGGCCGACAAGCAGAAGAACGGCATCAAGGTGAACTTCAAGATCCGCCACAACATCGAGGACGGC

AGCGTGCAGCTCGCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGGAGTTCGTGACCG

CCGCCGGGATCACTCTCGGCATGCACGAGCTGTACAAGTAAGAGCTCCCCGATTTTGTAGTAGAGGATCCAAAACAA

TCTCAGATATGGGAAATTTCAGGAGCAGAGTTTACATCTTCCAAGTCCCATACCGCAAATGGAATATCCATTAGATT

TCCTAGATTTACTAGGATAAGAGAGGATAAAACGTGGAAAGAATCTACTCATCTAAACGATTTAGTAAACTTGACTA

AATCTTAATTTTTATCTCGAGGCCGCTGGTACCCAACCTAAAAATTGAAAATAAATACAAAGGTTCTTGAGGGTTGT

GTTAAATTGAAAGCGAGAAATAATCATAAATAAGCCCgggATGGCGTCTAGTTCTAATTATAATACTTATATGCAAT

ATCTAAATCCACCACCATATGCGGATCATGGTGCTAATCAACTAATTCCAGCGGATCAACTATCTAATCAACATGGA

ATTACACCAAATTATGTTGGAGATCTAAATCTAGATGATCAGTTTAAAGGAAATGTTTGTCATGCGTTTACACTAGA

AGCGATTATTGATATTTCTGCGTATAATGAAAGAACAGTAAAAGGTGTACCAGCTTGGCTACCACTAGGAATTATGT

CTAATTTTGAATATCCACTAGCGCATACAGTAGCGGCGCTATTGACAGGATCTTATACAATTACACAGTTTACACAT

AATGGACAAAAgTTTGTTAGAGTAAATAGACTAGGAACTGGAATACCAGCGCATCCACTAAGAATGCTAAGAGAAGG

AAATCAAGCTTTTATTCAAAATATGGTTATTCCAAGAAATTTcTCTACAAATCAGTTTACTTATAATCTAACTAATC
```

-continued

```
TAGTACTATCTGTACAAAAgCTACCAGATGATGCTTGGAGACCATCTAAAGATAAACTAATTGGAAATACAATGCAT

CCAGCGATTTCTATTCATCCAAATCTACCACCAATAGTACTACCAACTGTAAAgAAACAAGCGTATAGACAACATAA gAATCCAATAATGGACCACTATTGGCGATTTCTGGAATTCTACATCAACTAAGAGTAGAAAAgGTACCAGAAAAgA

CATCTTTGTTTAGAATTTCTCTACCAGCGGATATGTTTTCTGTAAAAGAAGGAATGATGAAgAAAAGAGGAGAATCT

TCTCCAGTAGTATATTTTCAAGCGCCAGAAAATTTTCCATTGAATGGTTTTAATAATAGACAAGTAGTACTAGCGTA

TGCGAATCCAACACTATCTGCGATATAAtaagTCGACCTGCAGCTAATGTATTAGTTAAATATTAAAACTTACCACG

TAAAACTTAAAATTTAAAATGATATTTCATTGACAGATAGATCACACATTATGAACTTTCAAGGACTTGTGTTAACT

GACAATTGCAAAAATCAATGGGTCGTTGGACCATTAATAGGAAAAGGTGGATTTGGTAGTATTTATACTACTAATGA

CAATAATTATGTAGTAAAAATAGAGCCCAAAGCTAACGGATCATTATTTACCGAACAGGCATTTTATACTAGAGTAC

TTAAACCATCCGTTATCGAAGAATGGAAAAAATCTCACAATATAAAGCACGTAGGTCTTATCACGTGCAAGGCATTT

GGTCTATACAAATCCATTAATGTGGAATATCGATTCTTGGTAATTAATAGATTAGGTGCAGATCTAGATGCGGTGAT

CAGAGCCAATAATAATAGATTACCAAAAAGGTCGGTGATGTTGATCGGAATCGAAATCTTAAATACCATACAATTTA

TGCACGAGCAAGGATATTCTCACGGAGATATTAAAGCGAGTAATATAGTCTTGGATCAAATAGATAAGAATAAATTA

TATCTAGTGGATTACGGATTGGTTTCTAAATTCATGTCAAGCTTGTCTCCCTATAGTGAGTCGTATTAGAGCTTGGC

GTAATCATGGTCATAGCTGTTTCCTGTGTGAAATTGTTATCCGCTCACAATTCCACACAACATACGAGCCGGAAGCA

TAAAGTGTAAAGCCTGGGGTGCCTAATGAGTGAGCTAACTCACATTAATTGCGTTGCGCTCACTGCCCGCTTTCGAG

TCGGGAAACCTGTCGTGCCAGCTGCATTAATGAATCGGCCAACGCGCGGGGAGAGGCGGTTTGCGTATTGGGCGCTC

TTCCGCTTCCTCGCTCACTGACTCGCTGCGCTCGGTCGTTCGGCTGCGGCGAGCGGTATCAGCTCACTCAAAGGCGG

TAATACGGTTATCCACAGAATCAGGGGATAACGCAGGAAAGAACATGTGAGCAAAAGGCCAGCAAAAGGCCAGGAAC

CGTAAAAAGGCCGCGTTGCTGGCGTTTTTCGATAGGCTCCGCCCCCTGACGAGCATCACAAAAATCGACGCTCAAG

TCAGAGGTGGCGAAACCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTTTCTCATAGCTCACGC

TGTAGGTATCTCAGTTCGGTGTAGGTCGTTCGCTCCAAGCTGGGCTGTGTGCACGAACCCCCCGTTCAGCCCGACCG

CTGCGCCTTATCCGGTAACTATCGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGTGGTGGCCTAACTACGGCTACACT

AGAAGGACAGTATTTGGTATCTGCGCTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACGCGCAGAAAAAAAGGATCTCAAG

AAGATCCTTTGATCTTTTCTACGGGGTCTGACGCTCAGTGGAACGAAAACTCACGTTAAGGGATTTTGGTCATGAGA

TTATCAAAAAGGATCTTCACCTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCTGTCTATTTCGTTCATCCATAG

TTGCCTGACTCCCCGTCGTGTAGATAACTACGATACGGGAGGGCTTACCATCTGGCCCCAGTGCTGCAATGATACCG

CGAGACCCACGCTCACCGGCTCCAGATTTATCAGCAATAAACCAGCCAGCCGGAAGGGCCGAGCGCAGAAGTGGTCC

TGCAACTTTATCCGCCTCCATCCAGTCTATTAATTGTTGCCGGGAAGCTAGAGTAAGTAGTTCGCCAGTTAATAGTT

TGCGCAACGTTGTTGGCATTGCTACAGGCATCGTGGTGTCACGCTCGTCGTTTGGTATGGCTTCATTCAGCTCCGGT

TCCCAACGATCAAGGCGAGTTACATGATCCCCCATGTTGTGCAAAAAAGCGGTTAGCTCCTTCGGTCCTCCGATCGT

TGTCAGAAGTAAGTTGGCCGCAGTGTTATCACTCATGGTTATGGCAGCACTGCATAATTCTCTTACTGTCATGCCAT

CCGTAAGATGCTTTTCTGTGACTGGTGAGTACTCAACCAAGTCATTCTGAGAATAGTGTATGCGGCGACCGAGTTGC

TCTTGCCCGGCGTCAATACGGGATAATACCGCGCCACATAGCAGAACTTTAAAAGTGCTCATCATTGGAAAACGTTC

TTCGGGGCGAAAACTCTCAAGGATCTTACCGCTGTTGAGATCCAGTTCGATGTAACCCACTCGTGCACCCAACTGAT

CTTCAGCATCTTTTACTTTCACCAGCGTTTCTGGGTGAGCAAAAACAGGAAGGCAAATGCCGCAAAAAAGGGAATA

AGGGCGACACGGAAATGTTGAATACTCATACTCTTCCTTTTTCAATATTATTGAAGCATTTATCAGGGTTATTGTCT
```

-continued

```
CATGAGCGGATACATATTTGAATGTATTTAGAAAAATAAACAAATAGGGGTTCCGCGCACATTTCCCCGAAAAGTGC
CACCTGACGTCTAAGAAACCATTATTATCATGACATTAACCTATAAAAATAGGCGTATCACGAGGCCCTTTCGTCTC
GCGCGTTTCGGTGATGACGGTGAAAACCTCTGACACATGCAGCTCCCGGAGACGGTCACAGCTTGTCTGTAAGCGGA
TGCCGGGAGCAGACAAGCCCGTCAGGGCGCGTCAGCGGGTGTTGGCGGGTGTCGGGCTGGCTTAACTATGCGGCAT
CAGAGCAGATTGTACTGAGAGTGCACCATATGCGGTGTGAAATACCGCACAGATGCGTAAGGAGAAAATACCGCATC
AGGCGCCATTCGCCATTCAGGCTGCGCAACTGTTGGGAAGGGCGATCGGTGCGGGCCTCTTCGCTATTACGCCAGCT
GGCGAAAGGGGGATGTGCTGCAAGGCGATTAAGTTGGGTAACGCCAGGGTTTTCCCAGTCACGACGTTGTAAAACGA
CGGCCAGTGAATTGGATTTAGGTGACACTATA
```

TABLE 10

Marburg Glycoprotein mutation table

| Changes (Silent mutation) | Mutation position on GP |
|---|---|
| T to C | 18 |
| T to C | 21 |
| A to G | 129 |
| A to G | 174 |
| A to G | 237 |
| T to C | 429 |
| T to C | 480 |
| A to G | 516 |
| A to G | 666 |
| A to G | 861 |
| A to G | 1125 |
| A to G | 1143 |
| A to G | 1182 |
| A to G | 666 |
| A to G | 861 |
| A to G | 1125 |
| A to G | 1143 |

TABLE 10-continued

Marburg Glycoprotein mutation table

| Changes (Silent mutation) | Mutation position on GP |
|---|---|
| A to G | 1182 |
| A to G | 1302 |
| A to G | 1395 |
| T to C | 1404 |
| A to G | 1527 |
| T to C | 1605 |
| T to C | 1608 |
| A to G | 1650 |
| A to G | 1656 |
| T to C | 1749 |
| A to G | 1884 |
| A to G | 1899 |
| T to C | 2028 |
| A to G | 2034 |

*Shown as lower case in SEQ ID NO: 15

SEQ ID 15:
pGEO-MARV2014 GP sequence optimized for insertion into MVA vector: (FIG. 10)

```
GAATTCCCTGGGACATACGTATATTTCTATGATCTGTCTTATATGAAGTCTATACAGCGAATAGATTCAGAATTTC
TACATAATTATATATTGTACGCTAATAAGTTTAATCTAACACTCCCCGAAGATTTGTTTATAATCCCTACAAATTT
GGATATTCTATGGCGTACAAAGGAATATATAGACTCGTTCGATATTAGTACAGAAACATGGAATAAATTATTATCC
AATTATTATATGAAGATGATAGAGTATGCTAAACTTTATGTACTAAGTCCTATTCTCGCTGAGGAGTTGGATAATT
TTGAGAGGACGGGAGAATTAACTAGTATTGTACAAGAAGCCATTTTATCTCTAAATTTACGAATTAAGATTTTAAA
TTTTAAACATAAAGATGATGATACGTATATACACTTTTGTAAAATATTATTCGGTGTCTATAACGGAACAAACGCT
ACTATATATTATCATAGACCTCTAACGGGATATATGAATATGATTTCAGATACTATATTTGTTCCTGTAGATAATA
ACTAAGGCGCGCCTTTCATTTTGTTTTTTTCTATGCTATAAATGGTGAGCAAGGGCGAGGAGCTGTTCACCGGGGT
GGTGCCCATCCTGGTCGAGCTGGACGGCGACGTAAACGGCCACAAGTTCAGCGTGTCCGGCGAGGGCGAGGGCGAT
GCCACCTACGGCAAGCTGACCCTGAAGTTCATCTGCACCACCGGCAAGCTGCCCGTGCCCTGGCCCACCCTCGTGA
CCACCCTGACCTACGGCGTGCAGTGCTTCAGCCGCTACCCCGACCACATGAAGCAGCACGACTTCTTCAAGTCCGC
CATGCCCGAAGGCTACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGACGGCAACATCCTGG
GGCACAAGCTGGAGTACAACTACAACAGCCACAACGTCTATATCATGGCCGACAAGCAGAAGAACGGCATCAAGGT
GAACTTCAAGATCCGCCACAACATCGAGGACGGCAGCGTGCAGCTCGCCGACCACTACCAGCAGAACACCCCCATC
GGCGACGGCCCCGTGCTGCTGCCCGACAACCACTACCTGAGCACCCAGTCCGCCCTGAGCAAAGACCCCAACGAGA
AGCGCGATCACATGGTCCTGCTGGAGTTCGTGACCGCCGCCGGGATCACTCTCGGCATGCACGAGCTGTACAAGTA
```

-continued

AGAGCTCGAGGACGGGAGAATTAACTAGTATTGTACAAGAAGCCATTTTATCTCTAAATTTACGAATTAAGATTTT
AAATTTTAAACATAAAGATGATGATACGTATATACACTTTTGTAAAATATTATTCGGTGTCTATAACGGAACAAAC
GCTACTATATATTATCATAGACCTCTAACGGGATATATGAATATGATTTCAGATACTATATTTGTTCCTGTAGATA
ATAACTAACTCGAGGCCGCTGGTACCCAACCTAAAAATTGAAAATAAATACAAAGGTTCTTGAGGGTTGTGTTAAA
TTGAAAGCGAGAAATAATCATAAATAAGCCCgggATGTGGACAACATGTTTcTTcATTTCTCTAATTCTAATTCAA
GGAATTAAAACACTACCAATTCTAGAAATTGCGTCTAATGATCAACCACAAAATGTAGATTCTGTATGTTCTGGAA
CACTACAAAgACTGAAGATGTACATTTGATGGGTTTTACACTATCTGGACAAAgGTAGCGGATTCTCCACTAGA
AGCGTCTAAAAGATGGGCGTTTAGAACAGGTGTACCACCAAAgAATGTTGAATATACAGAAGGAGAAGAAGCGAAA
ACTTGTTATAATATTTCTGTAACAGATCCATCTGGAAAATCTCTACTACTAGATCCACCAACTAATGTTAGAGATT
ATCCAAAATGTAAAACAATTCATCATATTCAAGGACAAAATCCACATGCGCAAGGAATTGCGCTACATCTATGGGG
AGCATTcTTTCTATATGATAGAATAGCGTCTACAACAATGTATAGAGGAAAAGTTTTcACTGAAGGAAATATTGCG
GCTATGATAGTAAATAAgACAGTTCACAAAATGATATTTTCTAGACAAGGACAAGGATATAGACATATGAATCTAA
CATCTACAAATAAATATTGGACATCTTCTAATGGAACACAAACAAATGATACAGGATGTTTTGGAACATTGCAAGA
ATATAATAGTACAAAgAATCAAACATGTGCGCCATCTAAAACTCCACCACCACCTCCAACAGCGCATCCAGAAATT
AAACCTACATCTACACCAACAGATGCGACAAGATTGAATACAACAAATCCAAATTCTGATGATGAAGATCTAACAA
CATCTGGATCTGGAAGTGGAGAACAAGAACCATATACAACAAGTGATGCGGTTACAAAgCAAGGACTATCTTCTAC
AATGCCACCAACACTATCTCCACAACCTGGAACTCCACAACAAGGTGGAAATAATACAAATCATTCTCAAGATGCG
GCGACAGAACTAGATAATACTAATACAACTGCGCAACCACCAATGCCATCTCATAATACTACAACTATTTCTACTA
ATAATACTTCTAAACATAATCTATCTACATTGTCTGAACCACCTCAAAATACTACTAATCCTAATACTCAATCTAT
GGCGACTGAAAATGAAAgACTTCTGCGCCTCCAAAgACAACTCTACCACCAACTGAATCTCCAACAACAGAAAAg
AGTACAAATAATACAAAATCTCCAACTACAATGGAACCTAATACAACTAATGGACACTTTACATCTCCATCTTCTA
CTCCTAATTCTACAACACAACATTTGATATACTTTAGAAGAAAgAGATCTATTTTGTGGAGAGAAGGAGATATGTT
TCCATTTCTAGATGGATTGATTAATGCGCCAATTGATTTTGATCCAGTACCAAATACAAAgACAATTTTcGATGAA
TCTTCTTCTTCTGGTGCTTCTGCGGAAGAAGATCAACATGCGTCTAGTAATATTAGTCTAACATTGTCTTATCTAC
CTCATACTTCTGAAAATACTGCGTATAGTGGAGAAAATGAgAATGATTGTGATGCGGAACTAAGAATTTGGAGTGT
ACAAGAAGATGATCTAGCGGCGGGATTGTCTTGGATTCCTTTcTTcGGACCTGGAATTGAAGGACTATATACAGCG
GGATTGATTAAgAATCAgAATAATCTAGTATGTAGACTAAGAAGATTGGCGAATCAAACAGCGAAATCTCTAGAAC
TACTACTAAGAGTAACAACTGAAGAAAGAACATTcTCTTTTGATTAATAGACATGCGATTGATTTTCTATTGACAAG
ATGGGGAGGAACATGTAAAGTACTAGGACCAGATTGTTGTATTGGAATAGAAGATCTATCTAGAAATATTTCAGAA
CAAATTGATCAAATTAAgAAAGATGAACAAAAgGAAGGAACTGGATGGGACTAGGTGGAAAATGGTGGACATCTG
ATTGGGGAGTACTAACAAATCTAGGAATTCTACTATTGCTATCTATTGCGGTACTAATTGCGTTGTCTTGTATATG
TAGAATTTTcACAAAgTATATTGGATAATAAgTCGACCTGCAGTCAAACTCTAATGACCACATCTTTTTTTAGAGA
TGAAAAATTTTCCACATCTCCTTTTGTAGACACGACTAAACATTTTGCAGAAAAAAGTTTATTAGTGTTTAGATAA
TCGTATACTTCATCAGTGTAGATAGTAAATGTGAACAGATAAAAGGTATTCTTGCTCAATAGATTGGTAAATTCCA
TAGAATATATTAATCCTTTCTTCTTGAGATCCCACATCATTTCAACCAGAGACGTTTTATCCAATGATTTACCTCG
TACTATACCACATACAAAACTAGATTTTGCAGTGACGTCGTATCTGGTATTCCTACCAAACAAAATTTTACTTTTA
GTTCTTTTAGAAAATTCTAAGGTAGAATCTCTATTTGCCAATATGTCATCTATGGAATTACCACTAGCAAAAAATG
ATAGAAATATATATTGATACATCGCAGCTGGTTTTGATCTACTATACTTTAAAAACGAATCAGATTCCATAATTGC
CTGTATATCATCAGCTGAAAAACTATGTTTTACACGTATTCCTTCGGCATTTCTTTTTAATGATATATCTTGTTTA
GACAATGATAAAGTTATCATGTCCATGAGAGACGCGTCTCCGTATCGTATAAATATTTCATTAGATGTTAGACGCT -continued

```
TCATTAGGGGTATACTTCTATAAGGTTTCTTAATCAGTCCATCATTGGTTGCGTCAAGAACAAGCTTGTCTCCCTA
TAGTGAGTCGTATTAGAGCTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGTGAGCTAACTCACATTAATTG
CGTTGCGCTCACTGCCCGCTTTCGAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTTTTCGATAGGCTCCGCCCCCC
TGACGAGCATCACAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTGAAGCCAGT
TACCTTCGGAAAAAGAGTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACGGGGTCTGACGCTCAGT
GGAACGAAAACTCACGTTAAGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTACCAATGCTTAATCAGTGAG
GCACCTATCTCAGCGATCTGTCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAACGTTGTTGGCATTGCTACAGGCATCG
TGGTGTCACGCTCGTCGTTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGTTGGCCGCAGTGTTATCA
CTCATGGTTATGGCAGCACTGCATAATTCTCTTACTGTCATGCCATCCGTAAGATGCTTTTCTGTGACTGGTGAGT
ACTCAACCAAGTCATTCTGAGAATAGTGTATGCGGCGACCGAGTTGCTCTTGCCCGGCGTCAATACGGGATAATAC
CGCGCCACATAGCAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATACATATTTGAATGT
ATTTAGAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGATGCCGGGAGCAGACAAGCCCGT
CAGGGCGCGTCAGCGGGTGTTGGCGGGTGTCGGGGCTGGCTTAACTATGCGGCATCAGAGCAGATTGTACTGAGAG
TGCACCATATGCGGTGTGAAATACCGCACAGATGCGTAAGGAGAAAATACCGCATCAGGCGCCATTCGCCATTCAG
GCTGCGCAACTGTTGGGAAGGGCGATCGGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTTGTAAAACGACGGCCAGTGAATTGGATT
TAGGTGACACTATA
```

Example 5: MVA Vaccine Incorporating Lassa Virus Sequences

In an exemplary embodiment, sequences from Lassa Virus (LARV) are prepared and optimized in shuttle plasmids and then the viral sequences are incorporated into an MVA vector. Such MVA vectors may be used individually as part of an administration protocol to elicit an immune response to Lassa Virus or as part of a multivalent vaccine composition having one or more MVA vectors expressing EBOV and Lassa Virus antigens to elicit an immune response. Original Lassa GP and Z Sequences are obtained from Genbank (GenBank: JN650517.1 and JN650518.1) and optimized as described herein for insertion into MVA vectors.

TABLE 11

Lassa Glycoprotein mutation table

| Changes (Silent mutation) | Mutation position on GP |
| --- | --- |
| T to C | 21 |
| T to C | 24 |
| T to C | 114 |
| A to G | 264 |
| T to C | 351 |
| A to G | 375 |
| A to G | 378 |
| A to G | 483 |
| T to C | 573 |
| A to G | 669 |
| T to C | 699 |
| T to C | 786 |
| A to G | 816 |
| A to G | 912 |
| A to G | 1056 |
| T to C | 1197 |
| A to G | 1251 |
| A to G | 1275 |
| T to C | 1308 |
| T to C | 1320 |
| A to G | 1353 |

*Shown as lower case in SEQ ID NO: 16

Exemplary Lassa Virus GP and Z sequences are provided below.

```
SEQ ID 16:
Optimized Lassa GP sequence (GVX-LAS.GP) for
insertion into MVA vector:
ATGGGACAAATAGTAACATTcTTcCAAGAAGTACCACATGTAATTGAAGA

AGTAATGAATATTGTACTAATTGCGCTATCTGTACTAGCGGTATTGAAAG

GATTGTATAATTTcGCGACATGTGGACTAGTAGGACTAGTTACATTTCTA

CTACTATGTGGAAGATCTTGTACAACTTCTTTGTATAAAGGAGTATATGA

ACTACAAACACTAGAATTGAATATGGAAACTCTAAATATGACAATGCCTC

TATCATGTACAAAgAATAATTCTCATCATTATATTATGGTTGGAAATGAA

ACAGGACTAGAACTAACACTAACAAATACTTCTATTATTAATCATAAATT cTGTAATCTATCTGATGCGCATAAgAAgAATCTATATGATCATGCGCTAA

TGTCTATTATTTCTACATTTCATCTATCTATTCCAAACTTTAATCAATAT

GAAGCTATGTCTTGTGACTTTAATGGTGGAAAgATTTCTGTACAATATAA

TCTAAGTCATTCTTATGCGGGAGATGCGGCGAATCATTGTGGAACAGTAG

CGAATGGTGTACTACAAACTTTcATGAGAATGGCGTGGGGAGGATCTTAT

ATTGCGCTAGATTCTGGAAGAGGAAATTGGGATTGTATTATGACATCTTA

TCAATATCTAATTATTCAgAATACAACATGGGAAGATCATTGTCAATTcT

CTAGACCATCTCCAATAGGATATCTAGGACTACTATCTCAAAGAACAAGA

GATATATATATTAGTAGAAGATTGCTAGGAACTTTcACATGGACACTATC

TGATTCTGAAGGAAAgGATACACCTGGAGGATATTGTCTAACAAGATGGA

TGCTAATTGAAGCGGAATTGAAATGTTTTGGAAATACTGCGGTAGCGAAA

TGTAATGAAAAgCATGATGAAGAATTTTGTGATATGCTAAGACTATTTGA

CTTTAATAAACAAGCGATTCAAAGATTGAAAGCGGAAGCGCAAATGAGTA

TTCAATTGATAAATAAAGCGGTTAATGCTTTGATTAATGATCAACTAATT

ATGAAgAATCATCTAAGAGATATTATGGGAATTCCATATTGTAATTATAG

TAAATATTGGTATCTAAATCATACAACAACTGGAAGAACATCTCTACCAA

AATGTTGGCTAGTATCTAATGGATCTTATCTAAATGAAACACATTTcTCT

GATGATATTGAACAACAAGCGGATAATATGATTACAGAAATGCTACAAAA gGAATATATGGAAAGACAAGGAAAgACACCACTAGGATTGGTAGATCTAT

TTGTTTTcTCTACATCTTTcTATCTAATTAGTATATTTCTACATCTAGTA

AAgATTCCAACACATAGACATATAGTAGGAAAATCTTGTCCAAAACCACA

TAGATTGAATCATATGGGAATATGTTCTTGTGGATTGTATAAACAACCAG

GTGTACCAGTTAAATGGAAAAGATAAtaa

SEQ ID 17:
Optimized Z sequence (GVX-LAS.Z) for insertion
into MVA vector:
ATGGGAAATAAACAAGCGAAAGCGCCAGAATCTAAAGATTCTCCAAGAGC

GAGTCTAATTCCAGATGCGACACATCTAGGACCACAATTTTGTAAATCTT

GTTGGTTTGAAAATAAAGGACTAGTAGAATGTAATAATCATTATCTATGT

CTAAATTGTCTAACACTACTACTATCTGTATCTAATAGATGTCCAATATG

CAAAATGCCACTACCAACAAAACTAAGACCATCTGCTGCTCCAACAGCGC

CACCAACAGGTGCTGCTGATTCTATTAGACCACCACCATATTCTCCATAA taa
```

Example 6: Immunogenic and Protective Potential of the MVA/Z-VLP Vaccine

To test for the immunogenic and protective potential of the MVA/Z-VLP vaccine, two rodent models for Ebola virus (EBOV) infection and disease were tested for vaccine-elicited immune responses and protection against an EBOV challenge. The guinea pig and Syrian Golden Hamster (SGH) models were chosen because of the extensive experience with these models and the availability of suitable challenge stocks at the NIH Rocky Mountain Laboratories (RML) where challenges can be conducted under BSL4 containment.

Animal Study

Hamsters and guinea pigs were acquired by BIOQUAL, Inc., and randomized into two groups per species: a six-animal MVA/Z-VLP group and a two-animal MVA control (parental MVA, with no vaccine insert) group. Animals in the MVA/Z-VLP and MVA control groups were immunized intramuscularly at BIOQUAL. Two groups of naïve animals were also acquired and housed at BIOQUAL but were not vaccinated. All animals (MVA/Z-VLP, MVA control, and naïve control) were shipped to RML for challenge of the guinea pigs with guinea pig-adapted and the hamsters with mouse-adapted EBOV. Challenge was intraperitoneal with 10 plaque forming units of the respective adapted EBOV strains.

Table 12 summarizes the trial groups and procedures.

TABLE 12

Trial Groups and Procedures
Trial Groups and Procedures

| Group | Species and no. of animals[1] | Vaccine[2] | Immunization and bleed schedule (week in study) | | | Sampling schedule (days post challenge)[3] | |
|---|---|---|---|---|---|---|---|
| | | | Imm. | Bleed for serum | Challenge | Weight | Bleed for serum |
| 1 | 6 guinea pigs[4] | MVA/Z-VLP | 0, 4 | 0, 4, 6 | 11 | 1-14 | 42 |
| 2 | 2 guinea pigs | Parental MVA | 0, 4 | 0, 4, 6 | 11 | 1-14 | 42 |
| 3 | 6 guinea pigs | none | N/A | 0, 4, 6 | 11 | 1-14 | 42 |
| 4 | 6 SGH | MVA/Z-VLP | 0, 4 | 0, 4, 6 | 11 | 1-14 | 42 |
| 5 | 2 SGH | Parental MVA | 0, 4 | 0, 4, 6 | 11 | 1-14 | 42 |
| 6 | 6 SGH | none | N/A | 0, 4, 6 | 11 | 1-14 | 42 |

[1]Young adult animals were used for vaccinations
[2]MVA/Z-VLP and parental MVA were used at a dose of 1 × 10$^8$ tissue culture infectious doses (TCID)50
[3]Animals were euthanized on day 42.
[4]One guinea pig died of unrelated causes before the 2$^{nd}$ vaccination Immune Responses Vaccine induced binding Ab was determined by an ELISA using a secreted EBOV glycoprotein produced by a recombinant baculovirus in insect cells Plates were coated with the secreted EBOV glycoprotein or a control baculovirus supernatant that expressed no EBOV antigens. After blocking with 5% dry milk in 2% normal goat serum, serial serum dilutions were added to duplicate wells coated with both the EBOV glycoprotein and control supernatant. Antibody binding was detected by peroxidase-labeled anti-guinea pig IgG or peroxidase-labeled anti-hamster IgG and tetramethylbenzidine substrate. Reactions were stopped with 1N hydrochloric acid. Each plate included a standard curve generated using anti-guinea pig IgG and guinea pig IgG or anti-hamster IgG and hamster IgG. Standard curves were fitted, and sample concentrations were interpolated as micrograms of antibody per milliliter of serum using SoftMax Pro v.5.4.5. Background was calculated as antibody raised in wells coated with control baculovirus supernatant and was subtracted from EBOV glycoprotein antibody titers to obtain final results. These data are shown in FIGS. 11A and 11B.

The results of the binding Ab assays showed a single inoculation of MVA/Z-VLP eliciting similar titers of binding Ab as a single inoculation of a chimeric VSV expressing GP. It was, a chimeric VSV vector (rVSV-ZEBOV), which achieved protection against Ebola in Guinea (Agnandj S. T., N Engl J Med (2015)).

Neutralizing Antibody

Neutralizing antibody titers were determined by focus reduction neutralization assay. Vero cells were seeded into 96-well plates at a density adequate to generate a confluent monolayer on the day of infection. Serum dilutions were prepared in PBS. For each dilution, 10 μL of diluted serum was mixed with 10 μL of medium containing 100 focus-forming units (PFU) of ZEBOV-GFP (total volume of 20 μL). After 30 min at 37° C., the media was removed from cells, the serum-virus mixture was added and the samples were incubated for 60 min at 37° C. Then the mixture was removed from the cells, 100 μL of 1.2% carboxymethylcellulose-MEM was added and the cells were incubated for 4 days at 37° C. The neutralizing antibody titer of the serum samples was considered positive at a dilution showing a >80% reduction in GFP-foci compared with the control without serum. These data are shown in FIGS. 12A and 12B.

The titers are comparable to those from other vaccines that have shown protective efficacy against EBOV in rodents and non-human primates. For example, neutralizing titers elicited by other EBOV vaccine candidates (including VSVΔG/ZEBOVGP, Adeno, and VLP) in rodents or non-human primates vary from 1:20 to 1:160 (Ye, L., et al. *Virology* 351, 260-270 (2006); Marzi, A., et al. *J Infect Dis* 204 Suppl 3, S1066-1074 (2011); Feldmann, H., et al. *PLoS Pathog* 3(2007), Warfield, K. L., et al. *J Infect Dis* 15, 8 (2007)).

Challenge Results

The guinea pigs and hamsters were challenged intraperitoneally with 10 pfu of either guinea pig-adapted or mouse-adapted EBOV, respectively. The animals were weighed daily for 14 days. On day 42 post challenge, a terminal serum sample will be taken from all the survivors. These data are down in FIG. 13A-13D.

All of the control guinea pigs (the two vaccinated with parental MVA and the 6 unvaccinated) succumbed to the lethal challenge. One of the two hamsters receiving parental MVA succumbed and four of the unvaccinated SGHs succumbed. Minimal weight loss (1-2%) occurred on days 5-7 for the vaccinated guinea pigs and no weight loss, but a leveling in weight gain, occurred on days 4-6 for the vaccinated SGHs. In contrast, all of the unvaccinated animals underwent major losses in weight.

The complete protection elicited in rodents by MVA/Z-VLP is comparable to that seen from other vaccines that have shown protective efficacy. For example, it has been shown that a VSV-based vaccine candidate (VSVDG/ZE-BOV) protects SGH and guinea pigs from lethal challenge with the Zaire strain of Ebola (Marzi, A., et al. *J Infect Dis* 204 Suppl 3, S1066-1074 (2011); Tsuda, Y., et al. *J Infect Dis* 204, 8, (2011)).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference in their entirety.

The invention claimed is:

1. A method of preventing an infection by a Marburg virus in a human subject at risk of exposure thereto, said method comprising administering to the human subject in need thereof a pharmaceutical composition in a prophylactically effective amount, wherein the pharmaceutical composition comprises:
   a) a recombinant modified vaccinia ankara (MVA) vector comprising:
      i) a first nucleic acid encoding a Marburg virus (MARV) glycoprotein, and
      ii) a second nucleic acid sequence encoding a Marburg virus (MARV) VP40 matrix protein;
      wherein both the first nucleic acid sequence and the second nucleic acid sequence are under the control of one or more promoters compatible with poxvirus expression systems;
      wherein the first nucleic acid is located between MVA genes I8R and G1L;
      wherein the second nucleic acid sequence is located between MVA genes A50R and B1R in a restructured and modified deletion site III; and
      wherein the MARV glycoprotein and the MARV VP40 matrix protein are capable of assembling into virus-like particles (VLPs) when expressed in a host cell; and
   b) a pharmaceutically acceptable carrier.

2. The method of claim 1, wherein the first nucleic acid sequence and the second nucleic acid sequence are optimized by one or more method selected from the group consisting of i) changing selected codons to other synonymous codons that are optimal for protein expression by MVA, ii) interrupting homopolymer stretches using silent mutations, and iii) interrupting transcription terminator motifs using silent mutations.

3. The method of claim 1, wherein the MARV glycoprotein and MARV VP40 matrix protein are derived from the same MARV strain.

4. The method of claim 1, wherein the first nucleic acid sequence comprises nucleic acids 1631-3676 of SEQ ID NO: 15, or a nucleic acid sequence at least 95% identical thereto.

5. The method of claim 1, wherein the first nucleic acid sequence comprises nucleic acids 1631-3676 of SEQ ID NO: 15.

6. The method of claim 1, wherein the second nucleic acid sequence comprises nucleic acids 1581-2492 of SEQ ID NO: 14, or a nucleic acid sequence at least 95% identical thereto.

7. The method of claim 1, wherein the second nucleic acid sequence comprises nucleic acids 1581-2492 of SEQ ID NO: 14.

8. The method of claim 1, wherein the first nucleic acid sequence comprises nucleic acids 1631-3676 of SEQ ID NO: 15, and the second nucleic acid sequence comprises nucleic acids 1581-2492 of SEQ ID NO: 14.

9. The method of claim 1, wherein the administration is repeated at least twice.

10. A method of preventing an infection by a Marburg virus in a human subject at risk of exposure thereto, said method comprising administering to the human subject in need thereof a pharmaceutical composition in a prophylactically effective amount, wherein the pharmaceutical composition comprises:
    a) a recombinant modified vaccinia ankara (MVA) vector comprising:
       i) a first nucleic acid sequence encoding a Marburg virus glycoprotein comprising nucleic acids 1631-3676 of SEQ ID NO: 15, or a nucleic acid sequence at least 95% identical thereto, and
       ii) a second nucleic acid sequence encoding a Marburg virus VP40 matrix protein comprising nucleic acids 1581-2492 of SEQ ID NO: 14, or a nucleic acid sequence at least 95% identical thereto;
       wherein both the first nucleic acid sequence and the second nucleic acid sequence are under the control of one or more promoters compatible with poxvirus expression systems;
       wherein the first nucleic acid is located between MVA genes I8R and G1L;
       wherein the second nucleic acid sequence is located between MVA genes A50R and B1R in a restructured and modified deletion site III; and
       wherein the Marburg virus glycoprotein and the Marburg virus VP40 matrix protein are capable of assembling into virus-like particles (VLPs) when expressed in a host cell; and
    b) a pharmaceutically acceptable carrier.

11. The method of claim 10, wherein the administration is repeated at least twice.

12. A method of inducing an immune response to a Marburg virus in a human subject at risk of exposure thereto, said method comprising administering to the human subject in need thereof a pharmaceutical composition in a prophylactically effective amount, wherein the pharmaceutical composition comprises:

a) at least one recombinant modified vaccinia ankara (MVA) vector comprising:
  i) a first nucleic acid encoding a Marburg virus (MARV) glycoprotein, and
  ii) a second nucleic acid sequence encoding a Marburg virus (MARV) VP40 matrix protein;
  wherein both the first nucleic acid sequence and the second nucleic acid sequence are under the control of one or more promoters compatible with poxvirus expression systems;
  wherein the first nucleic acid is located between MVA genes I8R and G1L;
  wherein the second nucleic acid sequence is located between MVA genes A50R and B1R in a restructured and modified deletion site III; and
  wherein the MARV glycoprotein and the MARV VP40 matrix protein are capable of assembling into virus-like particles (VLPs) when expressed in a host cell; and
b) a pharmaceutically acceptable carrier.

13. The method of claim 12, wherein the first nucleic acid sequence and the second nucleic acid sequence are optimized by one or more method selected from the group consisting of i) changing selected codons to other synonymous codons that are optimal for protein expression by MVA, ii) interrupting homopolymer stretches using silent mutations, and iii) interrupting transcription terminator motifs using silent mutations.

14. The method of claim 12, wherein the MARV glycoprotein and MARV VP40 matrix protein are derived from the same MARV strain.

15. The method of claim 12, wherein the first nucleic acid sequence comprises nucleic acids 1631-3676 of SEQ ID NO: 15, or a nucleic acid sequence at least 95% identical thereto.

16. The method of claim 12, wherein the first nucleic acid sequence comprises nucleic acids 1631-3676 of SEQ ID NO: 15.

17. The method of claim 12, wherein the second nucleic acid sequence comprises nucleic acids 1581-2492 of SEQ ID NO: 14, or a nucleic acid sequence at least 95% identical thereto.

18. The method of claim 12, wherein the second nucleic acid sequence comprises nucleic acids 1581-2492 of SEQ ID NO: 14.

19. The method of claim 12, wherein the first nucleic acid sequence comprises nucleic acids 1631-3676 of SEQ ID NO: 15, and the second nucleic acid sequence comprises nucleic acids 1581-2492 of SEQ ID NO:14.

20. The method of claim 12, wherein the administration is repeated at least twice.

21. A method of inducing an immune response to a Marburg virus in a human subject at risk of exposure thereto, said method comprising administering to the human subject in need thereof a pharmaceutical composition in a prophylactically effective amount, wherein the pharmaceutical composition comprises:
a) a recombinant modified vaccinia ankara (MVA) vector comprising:
  i) a first nucleic acid sequence encoding a Marburg virus glycoprotein comprising nucleic acids 1631-3676 of SEQ ID NO: 15, or a nucleic acid sequence at least 95% identical thereto, and
  ii) a second nucleic acid sequence encoding a Marburg virus VP40 matrix protein comprising nucleic acids 1581-2492 of SEQ ID NO: 14, or a nucleic acid sequence at least 95% identical thereto;
  wherein both the first nucleic acid sequence and the second nucleic acid sequence are under the control of one or more promoters compatible with poxvirus expression systems;
  wherein the first nucleic acid is located between MVA genes I8R and G1L;
  wherein the second nucleic acid sequence is located between MVA genes A50R and B1R in a restructured and modified deletion site III; and
  wherein the Marburg virus glycoprotein and the Marburg virus VP40 matrix protein are capable of assembling into virus-like particles (VLPs) when expressed in a host cell; and
b) a pharmaceutically acceptable carrier.

22. The method of claim 21, wherein the administration is repeated at least twice.

* * * * *